(12) United States Patent
Takahashi et al.

(10) Patent No.: US 11,103,389 B2
(45) Date of Patent: Aug. 31, 2021

(54) ABSORBENT ARTICLE HAVING STRETCHABLE REGION WITH HIGH PEELING STRENGTH AND METHOD FOR PRODUCING SAME

(71) Applicant: Daio Paper Corporation, Ehime (JP)

(72) Inventors: Aya Takahashi, Tochigi (JP); Yukina Furuhashi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 868 days.

(21) Appl. No.: 15/547,444

(22) PCT Filed: Jan. 29, 2016

(86) PCT No.: PCT/JP2016/052806
§ 371 (c)(1),
(2) Date: Jul. 28, 2017

(87) PCT Pub. No.: WO2016/121976
PCT Pub. Date: Aug. 4, 2016

(65) Prior Publication Data
US 2018/0008481 A1    Jan. 11, 2018

(30) Foreign Application Priority Data

Jan. 30, 2015 (JP) ................................. 2015-017498
Mar. 27, 2015 (JP) ................................. 2015-067325
(Continued)

(51) Int. Cl.
*A61F 13/496* (2006.01)
*A61F 13/15* (2006.01)
*A61F 13/49* (2006.01)

(52) U.S. Cl.
CPC ............ *A61F 13/496* (2013.01); *A61F 13/15* (2013.01); *A61F 13/4902* (2013.01); *A61F 13/49019* (2013.01)

(58) Field of Classification Search
None
See application file for complete search history.

(56) References Cited

U.S. PATENT DOCUMENTS 4,938,753 A * 7/1990 Van Gompel ..... A61F 13/49015
604/385.29
5,151,092 A * 9/1992 Buell ................ A61F 13/15593
604/385.3
(Continued)

FOREIGN PATENT DOCUMENTS

CN 1982046 A 6/2007
CN 101511579 8/2009
(Continued)

*Primary Examiner* — Michele M Kidwell
(74) *Attorney, Agent, or Firm* — Muncy, Geissler, Olds & Lowe, P.C.

(57) ABSTRACT

Both high air permeability and high peeling strength are achieved.

The above problem is solved by providing an underpants-type disposable diaper including a stretchable region (80) stretchable at least in one direction in an outer body (20), in which the stretchable region (80) is formed by stacking an elastic film (30) between a first sheet layer (20A) composed of a nonwoven fabric and a second sheet layer (20B) composed of a nonwoven fabric, and in a state in which the elastic film (30) is stretched in the stretching and contracting direction, the first sheet layer (20A) and the second sheet layer (20B) are joined via through holes (31) formed in the elastic film (30) at a large number of sheet bond portions (40) arranged at intervals in each of a stretching and contracting direction and a direction orthogonal thereto, and in the sheet bond portions (40), the first sheet layer (20A) and (Continued)

the second sheet layer (20B) are joined at least by a melted and solidified material (30*m*) of the elastic film (30) among the first sheet layer (20A) and the second sheet layer (20B).

11 Claims, 35 Drawing Sheets

(30) Foreign Application Priority Data

| | | |
|---|---|---|
| Mar. 30, 2015 | (JP) | 2015-070295 |
| Sep. 30, 2015 | (JP) | 2015-195459 |
| Nov. 10, 2015 | (JP) | JP2015-220312 |

(56) References Cited

U.S. PATENT DOCUMENTS

| | | | |
|---|---|---|---|
| 5,567,501 A * | 10/1996 | Srinivasan | D04H 1/558 428/137 |
| 5,567,507 A * | 10/1996 | Paff | B41M 5/502 428/32.13 |
| 6,572,595 B1 | 6/2003 | Klemp et al. | |
| 6,884,494 B1 * | 4/2005 | Curro | A47L 13/17 428/158 |
| 10,226,388 B2 * | 3/2019 | Nelson | A61F 13/4902 |
| 10,849,797 B2 * | 12/2020 | Sakai | A61F 13/49019 |
| 2002/0016122 A1 * | 2/2002 | Curro | B29C 55/18 442/381 |
| 2007/0123124 A1 | 5/2007 | Middlesworth et al. | |
| 2010/0051170 A1 * | 3/2010 | Nakakado | A61F 13/15739 156/73.1 |
| 2010/0168705 A1 | 7/2010 | Stabelfeldt et al. | |
| 2010/0215923 A1 | 8/2010 | Frost | |
| 2011/0319853 A1 | 12/2011 | Yamashita et al. | |
| 2013/0126070 A1 | 5/2013 | Siqueira et al. | |
| 2014/0130956 A1 | 5/2014 | Floberg et al. | |
| 2015/0297422 A1 * | 10/2015 | Nelson | A61F 13/51464 604/365 |
| 2019/0133846 A1 * | 5/2019 | Shirai | A61F 13/49 |

FOREIGN PATENT DOCUMENTS

| | | |
|---|---|---|
| CN | 103635167 | 3/2014 |
| CN | 104284644 B | 1/2015 |
| CN | 104302261 B | 1/2015 |
| EP | 2223796 A1 | 9/2010 |
| EP | 3202383 A1 | 9/2015 |
| EP | 3 299 161 | 3/2018 |
| JP | H 09285487 A | 11/1997 |
| JP | 10-029259 A | 2/1998 |
| JP | H 11216163 A | 8/1999 |
| JP | 2004-532758 A | 10/2004 |
| JP | 2006-198132 A | 8/2006 |
| JP | 2008-260131 A | 10/2008 |
| JP | 2008-295838 A | 12/2008 |
| JP | 4508885 B2 | 7/2010 |
| JP | 2010195044 A | 9/2010 |
| JP | 2010200974 A | 9/2010 |
| JP | 4934835 B2 | 5/2012 |
| JP | 2014150917 A | 8/2014 |
| JP | 2016140477 | 8/2016 |
| JP | 2016-185265 A | 10/2016 |
| JP | 6383712 B2 | 8/2018 |
| WO | WO 03000165 A | 1/2003 |
| WO | WO2008/126708 A1 | 10/2008 |
| WO | WO2011/048512 | 4/2011 |
| WO | WO 2012/036599 | 3/2012 |
| WO | WO2013/002691 A1 | 1/2013 |
| WO | WO-2013173289 A1 | 11/2013 |
| WO | WO-2013173293 A1 | 11/2013 |
| WO | WO2015/168032 A1 | 11/2015 |

* cited by examiner (a)

←Stretching and Contracting direction→

(b)

←Stretching and Contracting direction→

(c)

←Stretching and Contracting direction→

(a)

(b)

←Width direction(Stretching and Contracting direction)→

(a)

←Width direction(Stretching and Contracting direction)→

(b)

←Width direction(Stretching and Contracting direction)→

(a)

←Width direction(Stretching and Contracting direction)→

(b)

←Width direction(Stretching and Contracting direction)→

(a)

(b)

ABSORBENT ARTICLE HAVING STRETCHABLE REGION WITH HIGH PEELING STRENGTH AND METHOD FOR PRODUCING SAME

TECHNICAL FIELD

The present invention relates to an absorbent article having an elastic film stretchable structure formed by interposing an elastic film between sheet layers, and a method of manufacturing the same.

BACKGROUND ART

In absorbent articles, elastic characteristics are typically imparted to leg portions, waist portions, and the like to improve fitness to the surfaces of bodies. A typical approach to impart elastic characteristics is fixing of elongated elastically stretchable members, such as rubber threads, in a state stretched in the longitudinal direction. In order to impart elasticity over a certain range of width, rubber threads are disposed and fixed in the width direction at intervals in some embodiments. In addition, an approach to impart excellent surface fitting is fixing of elastic film in a state stretched in a direction of imparting elasticity (for example, see Patent Literature 1).

According to a stretchable structure using the elastic film (hereinafter also referred to as an elastic film stretchable structure), a stretchable region is composed of a first sheet layer, a second sheet layer, and an elastic film interposed therebetween, and the first sheet layer and the second sheet layer are joined via through holes formed in the elastic film at a large number of dot-like sheet bond portions arranged at intervals in a stretching and contracting direction and a direction orthogonal thereto while the elastic film is stretched in the stretching and contracting direction along the surfaces of the first sheet layer and the second sheet layer. In such an elastic film stretchable structure, in a natural length state, as the elastic film contracts between sheet bond portions, an interval between sheet bond portions is decreased, and a contraction wrinkle extending in the direction orthogonal to the stretching and contracting direction is formed between the sheet bond portions in the first sheet layer and the second sheet layer. On the contrary, in a stretched state, as the elastic film is stretched between the sheet bond portions, the interval between the sheet bond portions is increased and the contraction wrinkle in the first sheet layer and the second sheet layer is extended, and elastic stretching is allowed so that the first sheet layer and the second sheet layer can be completely spread. This elastic film stretchable structure has advantages as follows: surface fitness is excellent; the first sheet layer and the second sheet layer are not joined to the elastic film and joined each other but at an extremely low level, thus the elastic film stretchable structure has a satisfactory flexibility; and the through holes of the elastic film contribute to improvement in air permeability.

However, in a method described in Patent Literature 1, through holes of an elastic film are formed by extrusion, and a first sheet layer and a second sheet layer are directly joined by welding at positions of the through holes. Thus, there is a concern that since the peeling strength is low, peeling may occur when a strong force is applied. In addition, in Patent Literature 1, since the through holes of the elastic film are formed by the extrusion, an elastic film 30 is not left between a first sheet layer 20A and a second sheet layer 20B as illustrated in FIG. 8(b), and there is a concern that extrusion debris (not illustrated) may be movably left around the through holes 31.

In addition, as illustrated in FIG. 8(c), it can be assumed that the first sheet layer 20A and the second sheet layer 20B are joined through the elastic film 30 without forming the through holes in the elastic film 30. However, in this case, there is a problem that not only peeling strength is low, but also air permeability is extremely low due to the absence of the through holes.

Meanwhile, in the above-mentioned conventional elastic film stretchable structure, air permeability can hardly be expected where the through holes are not provided. Therefore, improvement of air permeability in the through holes is significantly important in improving whole air permeability. In an absorbent article, a decrease in air permeability causes discomfort due to stuffiness.

Regarding this point, as another embodiment, Patent Literature 1 proposes that the sheet bond portions be fractured to form vent holes by pulling the sheet bond portions in the direction orthogonal to the stretching and contracting direction after forming the sheet bond portions by welding. However, since an edge of a fractured portion corresponds to a sharp texture, the proposal may not be preferable for an absorbent article to be worn on a body by hand.

CITATION LIST

Patent Literature

Patent Literature 1: JP 2004-532758 A
Patent Literature 2: JP 09-285487 A
Patent Literature 3: JP 11-216163 A

SUMMARY OF INVENTION

Technical Problem

In this regard, a first problem is to achieve both high air permeability and high peeling strength.

In addition, a second problem is to improve air permeability without impairing a texture in an elastic film stretchable structure.

Solution to Problem

The invention solving the above first problem is described below.

Invention Described in Claim 1

An Absorbent Article Comprising
a stretchable region stretchable at least in one direction, wherein
the stretchable region is formed by stacking an elastic film between a first sheet layer composed of a nonwoven fabric and a second sheet layer composed of a nonwoven fabric, and in a state in which the elastic film is stretched in a stretching and contracting direction of the stretchable region, the first sheet layer and the second sheet layer are joined via through holes formed in the elastic film at a large number of sheet bond portions arranged at intervals in each of a stretching and contracting direction and a direction orthogonal thereto, and in the sheet bond portions, the first sheet layer and the second sheet layer are joined at least by a melted and solidified material of the elastic film among the first sheet layer and the second sheet layer.

Operational Advantage

In the stretchable region of the invention, when the elastic film is in the natural length state, the first sheet layer and the second sheet layer between the sheet bond portions stretch in a direction away from each other, and thus a contraction wrinkle extending in a direction intersecting the stretching and contracting direction is formed. When a gap is formed between the through holes of the elastic film and the sheet bond portions in this state, air permeability is imparted due to the gap even when a material of the elastic film is a non-porous film or a sheet. Further, even when any gap is not formed between the through holes of the elastic film and the sheet bond portions in this state, since the through holes of the elastic film stretch while the sheet bond portions do not stretch in a worn state of being stretched to some extent in a width direction, a gap is formed between the through holes of the sheet bond portions in the elastic film and the sheet bond portions. Thus, air permeability is imparted due to the gap even when a material of the elastic film is a non-porous film or a sheet. Therefore, the stretchable region of the invention has high air permeability. In addition, since the first sheet layer and the second sheet layer are joined at least by the melted and solidified material of the elastic film among the first sheet layer and the second sheet layer in the sheet bond portions, peeling strength is high as understood from Example described below. Therefore, according to the invention, it is possible to achieve both high air permeability and high peeling strength.

Invention Described in Claim 2

The absorbent article according to claim 1, wherein
fibers of the first sheet layer and the second sheet layer continuing from around the sheet bond portions are left in the sheet bond portions, and
the first sheet layer and the second sheet layer are joined by the melted and solidified material of the elastic film, which has infiltrated and solidified among the first sheet layer and the second sheet layer.

Operational Advantage

When such a structure is adopted, improved adhering of the melted and solidified material of the elastic film to the first sheet layer and the second sheet layer is obtained, and, in addition, strength of the first sheet layer and the second sheet layer rarely decreases. Thus, peeling strength is further enhanced.

Invention Described in Claim 3

The absorbent article according to claim 1 or 2, wherein
an area of each of the sheet bond portions in the stretchable region is in a range of 0.14 to 3.5 mm$^2$,
an area of an opening of each of the through holes in a natural length state is 1 to 1.5 times the area of each of the sheet bond portions, and
an area rate of the sheet bond portions in the stretchable region is in a range of 1.8 to 22.5%.

Operational Advantage

The area of each of the sheet bond portions, the area of the opening of each of the through holes, and the area rate of the sheet bond portions may be appropriately determined. In general, it is desirable to set the areas and the area rate within the above ranges.

Invention Described in Claim 4

The absorbent article according to any one of claims 1 to 3, wherein the absorbent article is an underpants-type disposable diaper having
an outer body included in a front body and a back body,
an inner body that includes an absorber and is fixed to an internal surface of the outer body and, wherein
both side portions of the front body of the outer body are respectively joined to both side portions of the back body of the outer body to define side seal portions, and an annular torso region, a waist opening, and a pair of right and left leg openings are thereby formed, and
the stretchable region is included in the outer body.

Operational Advantage

The outer body of the underpants-type disposable diaper having such a structure is required to have elasticity in a wide range and be excellent in air permeability, and thus is particularly suitable for the invention.

Invention Described in Claim 5

A method of manufacturing an absorbent article including a stretchable region stretchable at least in one direction, wherein
in forming the stretchable region, in a state in which an elastic film is interposed between a first sheet layer composed of a nonwoven fabric and a second sheet layer composed of a nonwoven fabric while the elastic film is stretched in a stretching and contracting direction of the stretchable region,
the first sheet layer and the second sheet layer are welded at a large number of positions arranged at intervals in each of the stretching and contracting direction and a direction orthogonal thereto, thereby
the elastic film is melted at the large number of positions to form through holes, and
the first sheet layer and the second sheet layer are joined at least by solidification of melted material of the elastic film at the positions of the through holes.

Operational Advantage

When welding is performed by heat sealing, ultrasonic sealing, etc. in an arrangement pattern of the sheet bond portions in a state in which the elastic film is interposed between the first sheet layer and the second sheet layer as described above, the through holes may be formed in the elastic film, as well as the first sheet layer and the second sheet layer may be joined by solidification of the melted material of the elastic film via the through holes, and thus manufacture may be simply and efficiently performed. Furthermore, both high air permeability and high peeling strength are achieved in the manufactured stretchable region similarly to that described in claim 1.

Invention Described in Claim 6

The method of manufacturing an absorbent article according to claim 5, wherein a melting point of the first sheet layer and a melting point of the second sheet layer are higher than a melting point of the elastic film, the elastic film is melted at the positions for welding, and a part of the first sheet layer and the second sheet layer is not melted or a whole of the first sheet layer and the second sheet layer is not melted.

Operational Advantage

It is possible to manufacture the stretchable region of the invention described in claim 2 while having the same advantage as that in the invention described in claim 5.

The invention solving the above second problem is described below.

Invention Described in Claim 7

An absorbent article having an absorber that absorbs excrement, the absorbent article comprising an elastic film stretchable structure in which an elastic film is stacked between a first sheet layer and a second sheet layer, and the first sheet layer and the second sheet layer are joined via through holes penetrating the elastic film at a large number of sheet bond portions arranged at intervals, wherein a region having the elastic film stretchable structure includes a stretchable region stretchable in at least one direction, the stretchable region is contracted in a stretching and contracting direction by a contraction force of the elastic film while it is possible that the stretchable region is stretched in the stretching and contracting direction, and in at least one of the first sheet layer and the second sheet layer of the stretchable region, a vent hole is formed by piercing to penetrate the sheet layer in a thickness direction at a portion other than the sheet bond portions.

Operational Advantage

In the invention, air permeability in the thickness direction may be improved by the through holes of the elastic film and the vent hole of at least one of the first sheet layer and the second sheet layer. Furthermore, since a vent hole is formed by piercing at least one of the first sheet layer and the second sheet layer at a portion other than the sheet bond portions, a texture is not impaired unlike a case in which the vent hole is formed by fracture of the sheet bond portions as in Patent Literature 1. Here, the vent hole of the present invention is formed by piercing, and thus passages, which are originally possessed by the material for air permeability, are not included. For example, in a case that the material of the first sheet layer and of the second sheet layer are composed of air permeable fiber materials such as nonwoven fabrics, intervals between fibers are not included in the above "vent hole" of the invention.

Invention Described in Claim 8

The absorbent article according to claim 7, wherein in a state in which the stretchable region is stretched, the vent hole is disposed with respect to the through holes such that a part or a whole of the vent hole overlaps each of the through holes.

Operational Advantage

Since the through hole formed in the elastic film is enlarged when the stretchable region is stretched at the time of use, air permeability via the through hole is particularly improved when the vent hole is disposed such that a part or a whole of the vent hole overlaps the enlarged through hole, which is preferable.

Invention Described in Claim 9

The absorbent article according to claim 7, wherein independently of a state in which the stretchable region is stretched or not, none of the vent hole overlaps the through holes.

Operational Advantage

When the stretchable region is stretched during use, the through holes formed in the elastic film are enlarged. Thus, when a part or a whole of the vent hole is disposed to overlap the enlarged through hole, there is a concern that a skin exposure may increase due to improvement of permeability, or leak prevention may deteriorate even though air permeability is improved. Therefore, a configuration described in this claim is also one of preferable modes.

Invention Described in Claim 10

The absorbent article according to any one of claims 7 to 9, wherein the first sheet layer is a nonwoven fabric and the second sheet layer is a nonwoven fabric, and the number of vent holes per unit area is smaller than the number of through holes per unit area.

Operational Advantage

The first sheet layer and the second sheet layer are layers that cover the elastic film, and are members that require durability such as rub resistance. In addition, when the first sheet layer is composed of a nonwoven fabric and the second sheet layer is composed of a nonwoven fabric, the number of vent holes may not be excessively increased since the material has air permeability. On the other hand, a considerable number of through holes of the elastic film are used to ensure air permeability and join uniformly the first sheet layer and the second sheet layer as one unit. Therefore, in a preferable mode, the number of vent holes is set to be smaller than the number of through holes.

Invention Described in Claim 11

The absorbent article according to any one of claims 7 to 10, wherein at least one vent hole is formed on each side of each of the sheet bond portions in the stretching and contracting direction.

Operational Advantage

When the stretchable region is stretched during use, the through holes formed in the elastic film are enlarged at both sides of the sheet bond portions in the stretching and contracting direction. Thus, it is preferable to form the vent hole at the position described in this claim in terms of improvement in air permeability compared with cases in which it is not.

Invention Described in Claim 9

The absorbent article according to claim 7, wherein an area of the vent hole is in a range of 0.34 to 3.5 $mm^2$, and an area rate of the vent hole is in a range of 4.4 to 19.1%.

Operational Advantage

The area of the vent hole is not particularly restricted. However, when the area is excessively small or an excessively small number of vent holes are present, an effect of improving air permeability becomes poor. When the size is excessively large or an excessively large number of vent holes are present, a decrease in strength or deterioration in appearance of the sheet layers is caused. Thus, the size is preferable set within the range described in this claim.

Invention Described in Claim 10

The absorbent article according to claim 7, wherein
a region having the elastic film stretchable structure includes a non-stretchable region provided at least at one side of the stretchable region in the stretching and contracting direction,
the non-stretchable region is a region in which an elongation at an elastic limit in the stretching and contracting direction is 130% or less, and
the vent hole is formed in the non-stretchable region and the vent hole is or is not formed in the stretchable region.

Operational Advantage

The area of the vent hole is not particularly restricted. However, when the area is excessively small or an excessively small number of vent holes are present, an effect of improving air permeability becomes poor. When the size is excessively large or an excessively large number of vent holes are present, a decrease in strength or deterioration in appearance of the sheet layers is caused. Thus, it is preferable to set the size within the range described in this claim.

Invention Described in Claim 11

The absorbent article according to claim 7, wherein
the absorbent article is an underpants-type disposable diaper having
an outer body included in a front body and a back body,
an inner body that includes an absorber and is fixed to the outer body, wherein
both side portions of the front body of the outer body are respectively joined to both side portions of the back body of the outer body to define side seal portions, and an annular torso region, a waist opening, and a pair of right and left leg openings are thereby formed, and
the elastic film stretchable structure is included in the torso region of the outer body in at least one of the front body and the back body such that the stretching and contracting direction thereof corresponds to a width direction.

Operational Advantage

The elastic film stretchable structure of the invention is excellent in air permeability, and thus is particularly suitable for the outer body of the underpants-type disposable diaper.

Advantageous Effects of Invention

As described above, according to the invention that solves the first problem, there is an advantage that both high air permeability and high peeling strength may be achieved, etc. In addition, according to the invention that solves the second problem, there is an advantage that air permeability may be improved without impairing a texture in an elastic film stretchable structure, etc.

DESCRIPTION OF EMBODIMENTS

Figure 1:
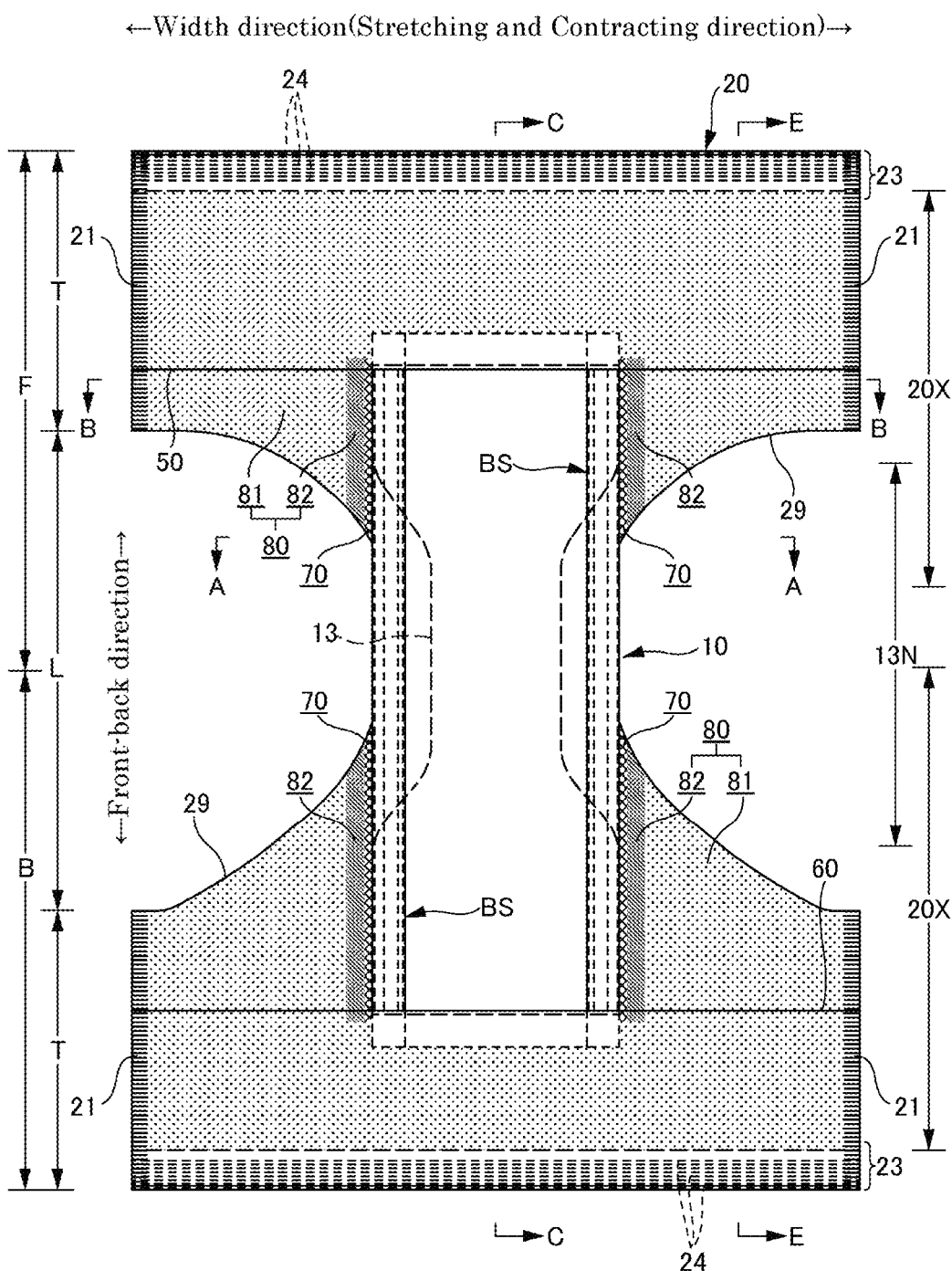
FIG. 1 is a plan view (internal surface side) of an underpants-type disposable diaper in a completely spread state.

Hereinafter, an embodiment of the invention will be described with reference to accompanying drawings. A dotted portion in a cross-sectional view indicates joining means such as a hot-melt adhesive.

With Regard to Common Matters

FIG. 1 to FIG. 7 illustrate an underpants-type disposable diaper. This underpants-type disposable diaper (hereinafter also simply referred to as a diaper) has an outer body 20 that includes a front body F and a back body B as one unit, an inner body 10 that is fixed to the internal surface of the outer body 20 as one unit. Further, in the inner body 10, an absorber 13 is interposed between a liquid pervious top sheet 11 and a liquid impervious sheet 12. In manufacturing, after a back surface of the inner body 10 is joined to the internal surface (upper surface) of the outer body 20 using joining means such as a hot-melt adhesive, the inner body 10 and the outer body 20 are folded at a center in a front-back direction (vertical direction) corresponding to a boundary between the front body F and the back body B, and both side portions thereof are joined to each other by heat sealing, a hot-melt adhesive, etc. to form a side seal portion 21, thereby obtaining an underpants-type disposable diaper in which a waist opening and a pair of right and left leg openings are formed.

Exemplary Structure of Inner Body

Figure 4:
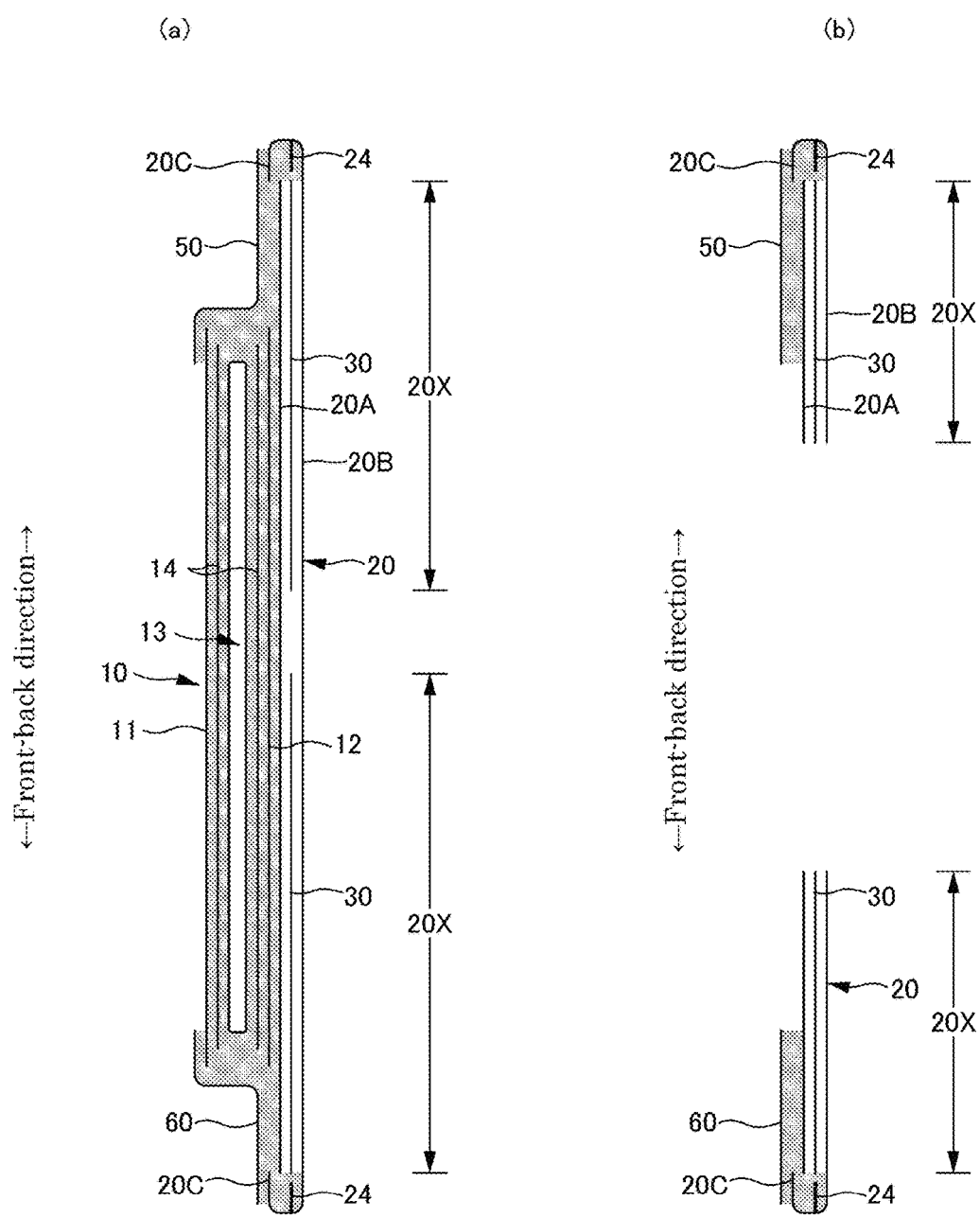
FIG. 4(a) is a C-C cross-sectional view of FIG. 1 and FIG. 31.
FIG. 4(b) is an E-E cross-sectional view of FIG. 1 and FIG. 31.
Figure 5:
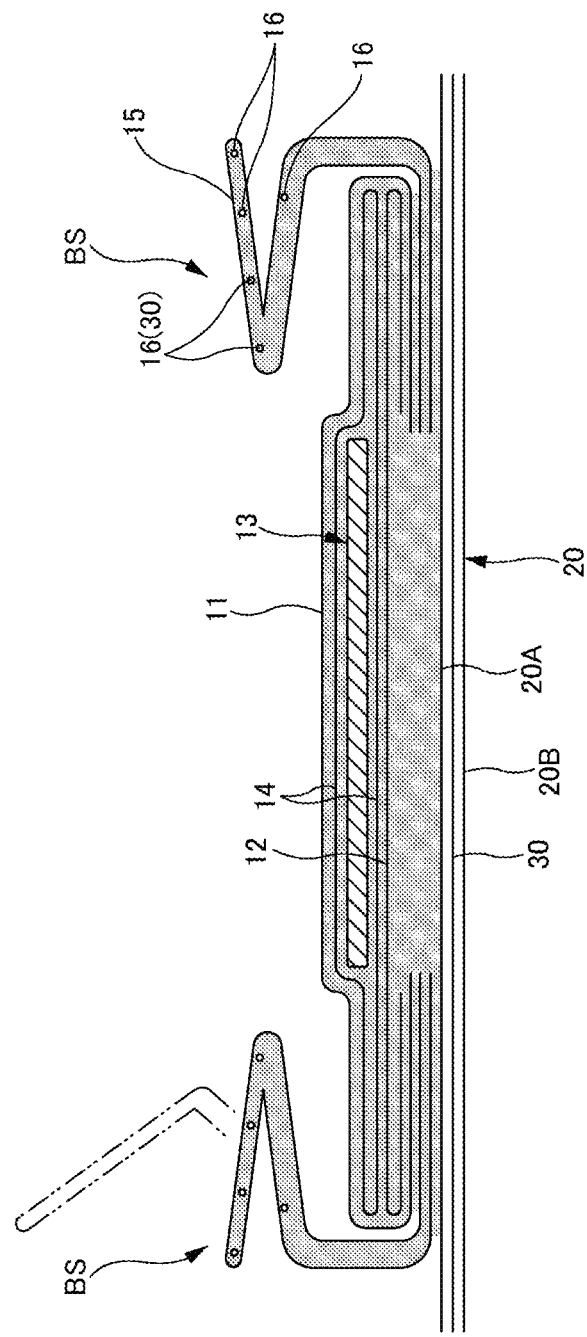
FIG. 5 is an A-A cross-sectional view of FIG. 1 and FIG. 20.
Figure 6:
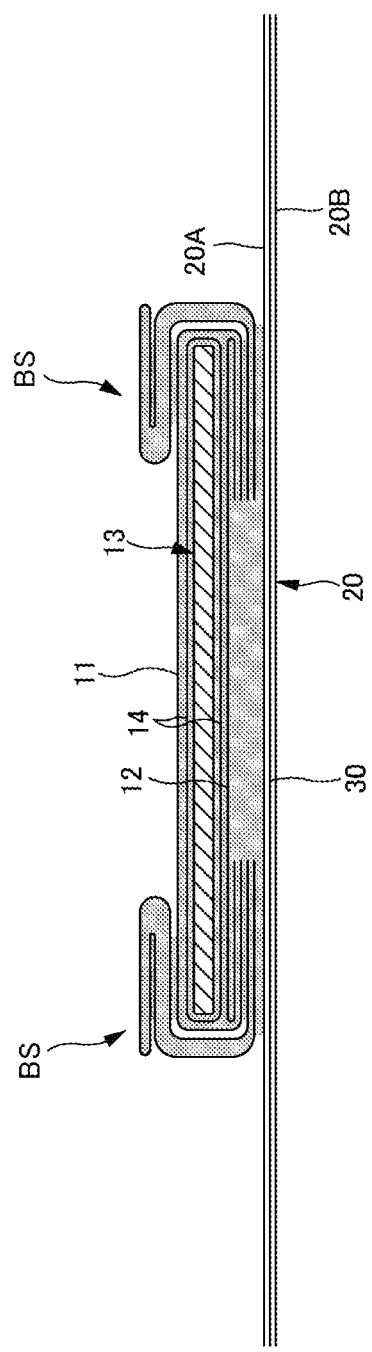
FIG. 6 is a B-B cross-sectional view of FIG. 1 and FIG. 20.

With reference to FIGS. 4 to 6, the inner body 10 includes a top sheet 11 composed of, for example, non-woven fabric, a liquid-impermeable sheet 12 composed of, for example, polyethylene, and an absorber 13 between the top sheet 11 and the liquid-impermeable sheet 12. The inner body 10 is configured to absorb and retain excretory fluid passing through the top sheet 11. The inner body 10 may have any planar shape and typically has a substantially rectangular shape as shown in the drawing.

The top sheet 11 that covers a front surface side (to come into contact with the skin) of the absorber 13 is preferably composed of perforated or imperforate nonwoven fabric or a porous plastic sheet. Examples of the raw fibers of the nonwoven fabric include synthetic fibers, such as olefin fibers, e.g., polyethylene and polypropylene, polyester fibers, and polyamide fibers; recycled fibers, such as rayon and cupra; and natural fibers, such as cotton. The nonwoven fabric can be produced by any process, for example, spun lacing, spun bonding, thermal bonding, melt blowing, or needle punching. Among these processes, preferred are spun lacing in view of flexibility and drape characteristics and thermal bonding in view of bulky soft products. A large number of through holes formed in the liquid-pervious front surface sheet 11 facilitates absorption of urine and achieves dry touch characteristics. The top sheet 11 extends around the side edges of the absorber 13 and extends to the back surface side of the absorber 13.

The liquid-impermeable sheet 12, covering the back surface side (not in contact with skin) of the absorber 13 is composed of a liquid-impervious plastic sheet, for example, polyethylene sheet or polypropylene sheet. Recently, permeable films have been preferably used in view of preventing stuffiness. This water-block permeable sheet is a microporous sheet prepared through melt-kneading an olefin resin, for example, polyethylene resin or polypropylene resin, and inorganic filler, forming a sheet with the kneaded materials, and then uniaxially or biaxially elongating the sheet.

The absorber 13 may be composed of a well-known basic component, such as an accumulated body of pulp fibers, an assembly of filaments, composed of, for example, cellulose acetate, or nonwoven fabric, and the absorber 13 may include as necessary high-absorbent polymer mixed or fixed to the basic component. The absorber 13 may be wrapped with a liquid-permeable and liquid-retainable package sheet 14, such as a crepe sheet, to retain the shape and polymers, as required.

The absorber 13 has a substantially hourglass shape having a narrow portion 13N with a width narrower than those of the front and back end portions of the absorber 13, at a crotch portion. Alternatively, the absorber 13 may have any other shape, for example, a rectangular shape, as appropriate. The size of the narrow portion 13N may be appropriately determined. The narrow portion 13N may have a length of approximately 20 to 50% of the entire length of the diaper along the front-back direction, and a width, at the narrowest region, of approximately 40 to 60% of the entire width of the absorber 13. If the inner body 10 has a substantially rectangular planar shape in the case of the absorber with such a narrower part 13N, the inner body 10 has portions free of the absorber 13 according to the narrower part 13N of the absorber 13.

Three-dimensional gathers BS, which are configured to fit around the legs, are formed on both side portions of the inner body 10. With reference to FIGS. 5 and 6, the three-dimensional gathers BS are each composed of a gather nonwoven fabric 15 folded into a duplicate sheet consisting of a fixed section fixed to the side portion of the back surface of the inner body, a main section extending from the fixed section around a side portion of the inner body to the side portion of the front surface of the inner body, lying down sections formed by fixing the front end portion and back end portion of the main section in a lying down state to the side portion of the front surface of the inner body, and a free section formed in an un-fixed state between the lying down sections.

Elongated gather elastic members 16 are disposed in the tip portion of the free sections of the duplicate sheet. As illustrated by the chain double-dashed line in FIG. 5, part of the nonwoven fabric protruding from a side edge of the absorber is erected by elastic stretching force of the gather elastic members 16 to form a three-dimensional gather BS in a completed product.

The liquid impervious sheet 12 is folded back to the back surface side together with the top sheet 11 at both sides of the absorber 13 in the width direction. The liquid-impervious back surface sheet 12 is preferably opaque to block transmission of brown color of stool and urine. Preferred examples of the opacifying agent compounded in the plastic film include colorant or filler, such as calcium carbonate, titanium oxide, zinc oxide, white carbon, clay, talc, and barium sulfate.

The gather elastic member 16 may be composed of commodity materials, for example, styrene rubber, olefin rubber, urethane rubber, ester rubber, polyurethanes, polyethylene, polystyrene, styrene-butadiene, silicones, and polyester. The gather elastic members 16 preferably have a fineness of 925 dtex or less and are disposed under a tension of 150% to 350% at an interval of 7.0 mm or less to be hidden from outside view. The gather elastic member 16 may have a string shape shown in the drawing or a tape shape with an appropriate width.

Like the top sheet 11, the gather nonwoven fabric 15 may be composed of raw fibers including synthetic fibers, such as olefin fibers of, for example, polyethylene fibers or polypropylene fibers; polyester fibers and amide fibers; recycled fibers of, for example, rayon and cupra; and natural fibers such as cotton. The gather nonwoven fabric may be prepared by any appropriate process, for example, spun bonding, thermal bonding, melt blowing, or needle punching. In particular, the basis weight should be reduced for production of a nonwoven fabric that can prevent stuffiness and has high air permeability. The gather nonwoven fabric 15 is preferably a water-repellent nonwoven fabric coated with a water repellent agent, for example, a silicone-based agent, a paraffin-metallic agent, or an alkyl chromic chloride agent to decrease permeability of urine and the like, to prevent diaper rash, and to enhance feeling to skin (dryness).

Figure 7:
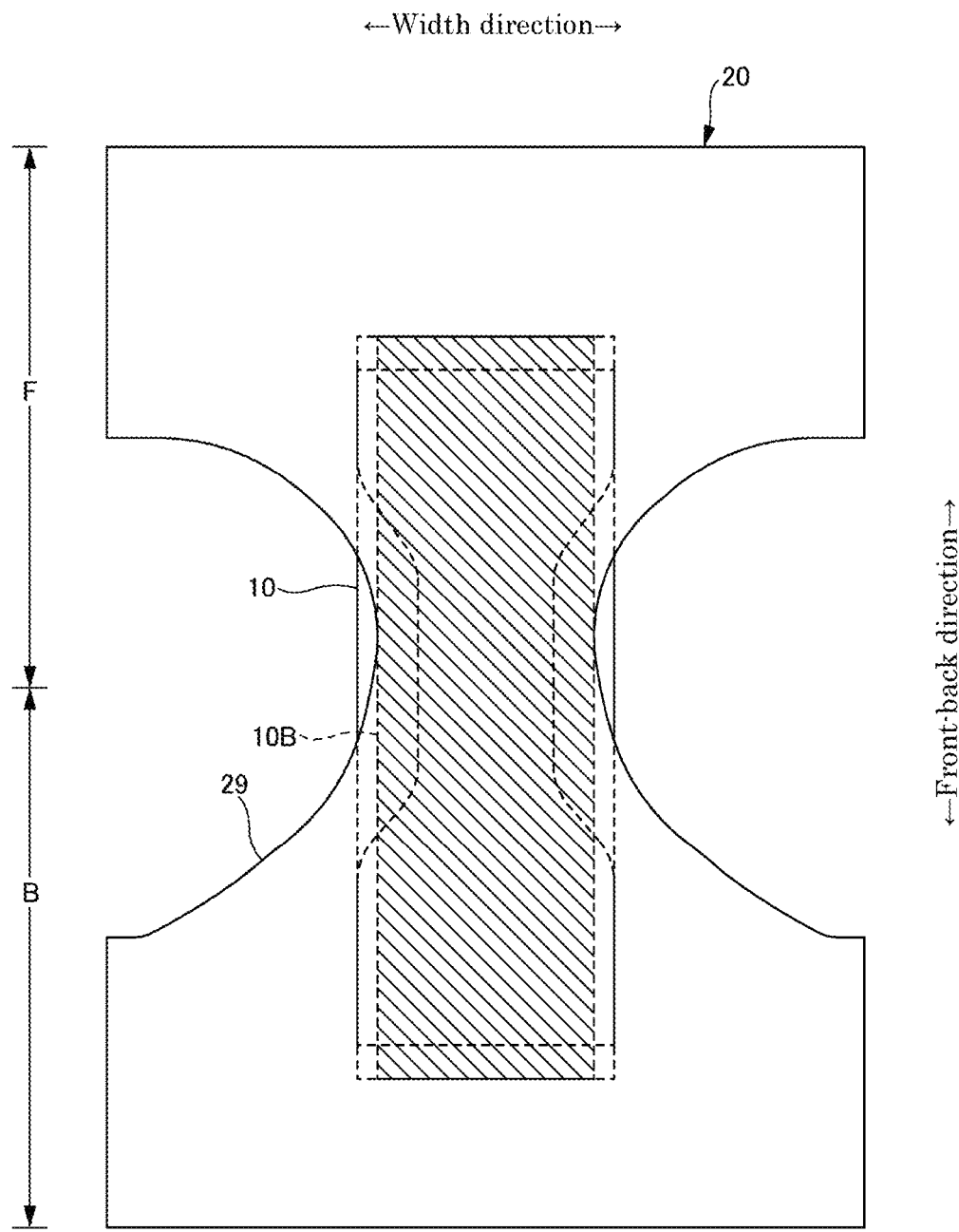
FIG. 7 is a plan view illustrating only a main part of the underpants-type disposable diaper in the completely spread state.
Figure 8:
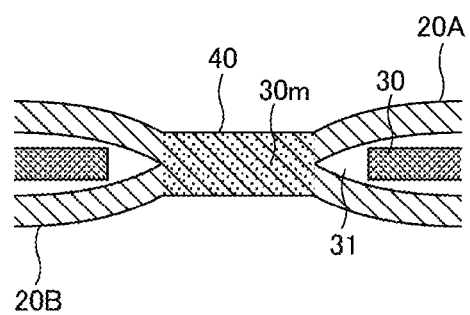
FIG. 8 is a cross-sectional view schematically illustrating a cross section of a main part of the outer body stretched to some extent in a width direction.
Figure 8:
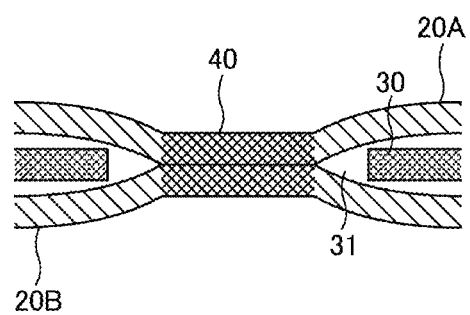
Figure 8:
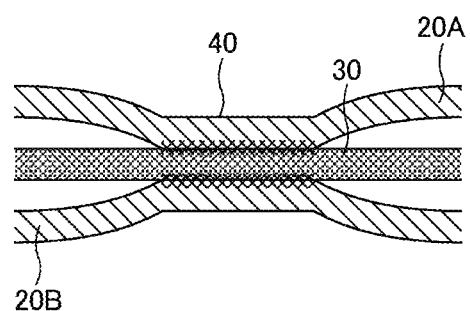

As illustrated in FIG. 7, the back surface of the inner body 10 is fixed to the internal surface of the outer body 20 by, for example, a hot-melt adhesive in an internal and external fixed region 10B (shaded area). The internal and external fixed region 10B extends over with a width range corresponding to a range from a side portion 17 free of the absorber at one side to another side portion 17 free of the absorber at the other side at the both front and back sides of the side portions 17. Side edges of the internal and external fixed region 10B are preferably positioned at lateral sides of the middle of the side portions 17 free of the absorber in the width direction. In particular, the internal and external fixed region 10B is preferably fixed to the substantially whole inner body 10 in the width direction and fixed to the substantially whole outer body 20 in the front-back direction.

Front and Back Cover Sheets

With reference to FIG. 1 and FIG. 4, front and back cover sheets 50, 60 may be provided to cover the front and back end portions of the inner body 10 attached to the internal surface of the outer body 20 to prevent leakage from the front and rear edges of the inner body 10. In more detail, the front cover sheet 50 extends over the entire width of the front body F on the internal surface of the front body F from the internal surface of the folded part 20C at the waist-side end of the front body F to a position overlapping with the front end portion of the inner body 10. The back cover sheet 60 extends on the internal surface of the back body Ba over the entire width, and extends over the entire width of the back body B from the internal surface of the folded part 20C at the waist-side end of the back body B to a position overlapping with the back end portion of the inner body 10, in the embodiment illustrated in the drawings. Minor non-bonded regions are provided over the entire width (or only at the central portion) at side edge portions of the front and back cover sheets 50 and 60 at the crotch portion-side. The front and back cover sheets 50 and 60 having such non-bonded regions can prevent leakage of the adhesive and function as barriers against leakage when slightly suspended from the top sheet.

As shown in the embodiment illustrated in the drawings, the front and back cover sheets 50, 60 as separate components advantageously enlarge the range of choice of material, but disadvantageously needs additional materials and manufacturing processes. Thus, the folded part 20C formed by folding back the outer body 20 toward the inner surface side of the diaper are respectively extended to portions overlapping with the inner body 10, so as to have the same function as that of the cover sheets 50, 60.

With Regard to Mode for Solve First Problem

First, a mode for solving the first problem will be described with reference to FIG. 1 to FIG. 19. In the outer body 20, as illustrated in FIG. 4 to FIG. 6, the elastic film 30 and elongated elastic members 24 along the width direction are arranged between the first sheet layer 20A and the second sheet layer 20B, and elasticity in the width direction is imparted. A planar shape of the outer body 20 corresponds to a pseudo-hourglass shape as a whole due to a concave line around leg 29 formed to form a leg opening at each of intermediate both side portions. The outer body 20 may be divided into two front and back parts, and the both parts may be separated from each other in the front-back direction by the crotch portion.

More specifically, in the outer body 20 of the illustrated mode, the waist portion elastic members 24 are provided in the waist end portion region in the torso region T defined as a vertical direction range of the side seal portion 21 in which the front body F and the back body B are joined. The waist portion elastic members 24 of the illustrated mode correspond to elongated elastic members such as a plurality of rubber threads disposed at intervals in the vertical direction, and apply a stretching force to tighten around the waist of the body. The waist portion elastic members 24 are not disposed closely substantially in a bundle, and three or more, preferably five or more members are disposed at intervals of about 3 to 8 mm to form a predetermined stretchable zone. A stretch rate of the waist portion elastic member 24 in fixing may be appropriately determined. However, the stretch rate may be set to about 230 to 320% in the case of normal adult use. One or a plurality of belt shaped elastic members may be used as the waist portion elastic member 24.

The rubber thread is used as the waist portion elastic member 24 in an illustrated example. However, for example, a tape shaped elastic member may be used, and an elastic film described below may be extended to the waist end portion region instead of using the tape shaped elastic member. The waist portion elastic member 24 in the illustrated mode is interposed in the folded part 20C formed by folding back a component of the second sheet layer 20B to the internal surface side at a waist opening edge. However, the waist portion elastic member 24 may be interposed between a component of the first sheet layer 20A and the component of the second sheet layer 20B.

The first sheet layer 20A and the second sheet layer 20B may be composed of any sheet members, preferably nonwoven fabrics in view of air permeability and flexibility. The nonwoven fabric may be composed of any raw fiber. Examples of the raw fiber include synthetic fibers, such as olefin fibers, e.g., polyethylene fibers and polypropylene fibers, polyester fibers, and polyamide fibers; recycled fibers, such as rayon and cupra; natural fibers, such as cotton; and blend or conjugate fibers composed of two or more of these fibers. The nonwoven fabric may be prepared by any process. Examples of such a process include well-known processes, such as spun lacing, spun bonding, thermal bonding, melt blowing, needle punching, air-through processes, and point bonding. The nonwoven fabric preferably has a basis weight of approximately 10 to approximately 25 g/m². The first sheet layer 20A and the second sheet layer 20B may be composed of a pair of facing layers prepared by folding back a single sheet that is partially or entirely folded back.

Figure 2:
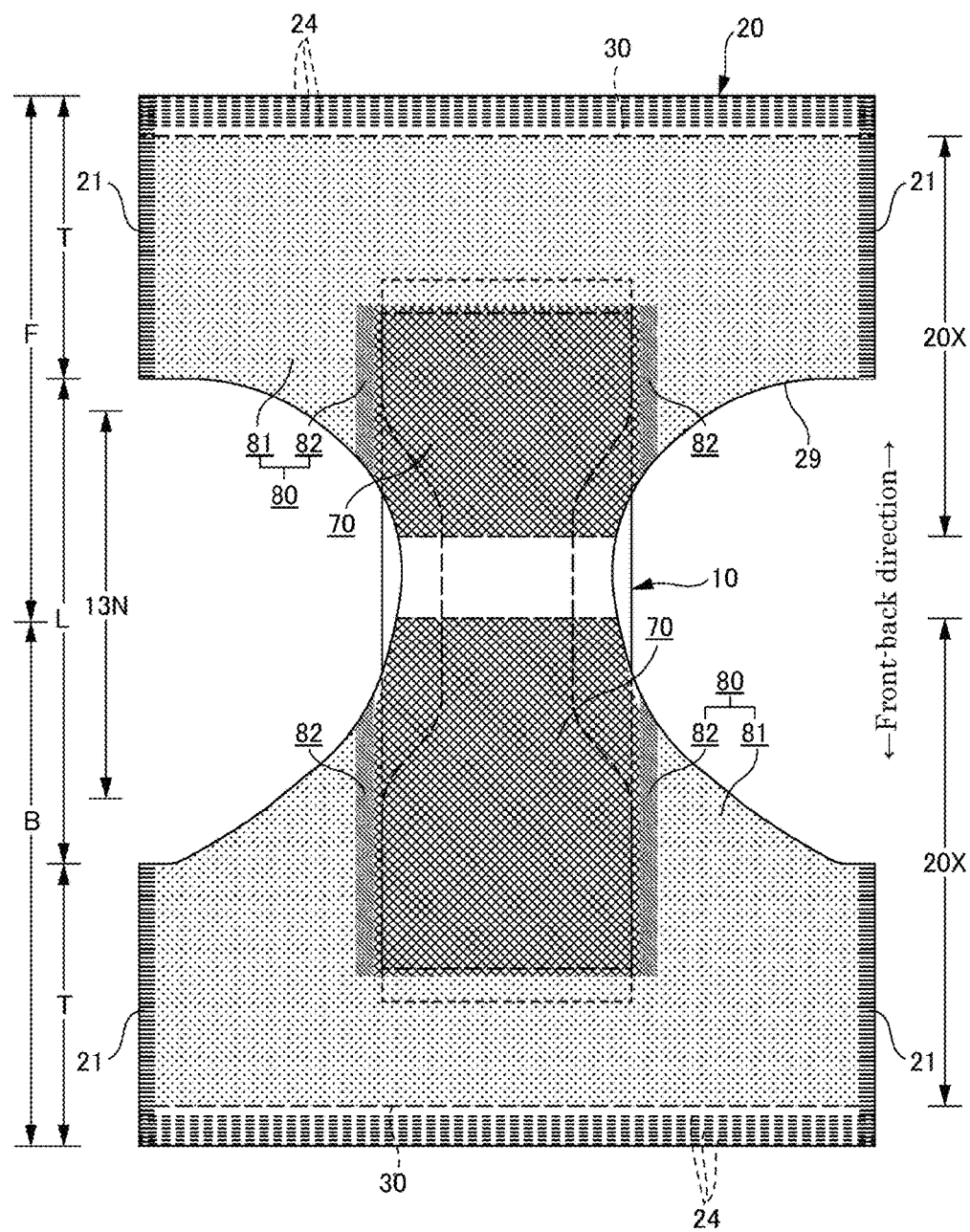
FIG. 2 is a plan view (external surface side) of the underpants-type disposable diaper in the completely spread state.
Figure 3:
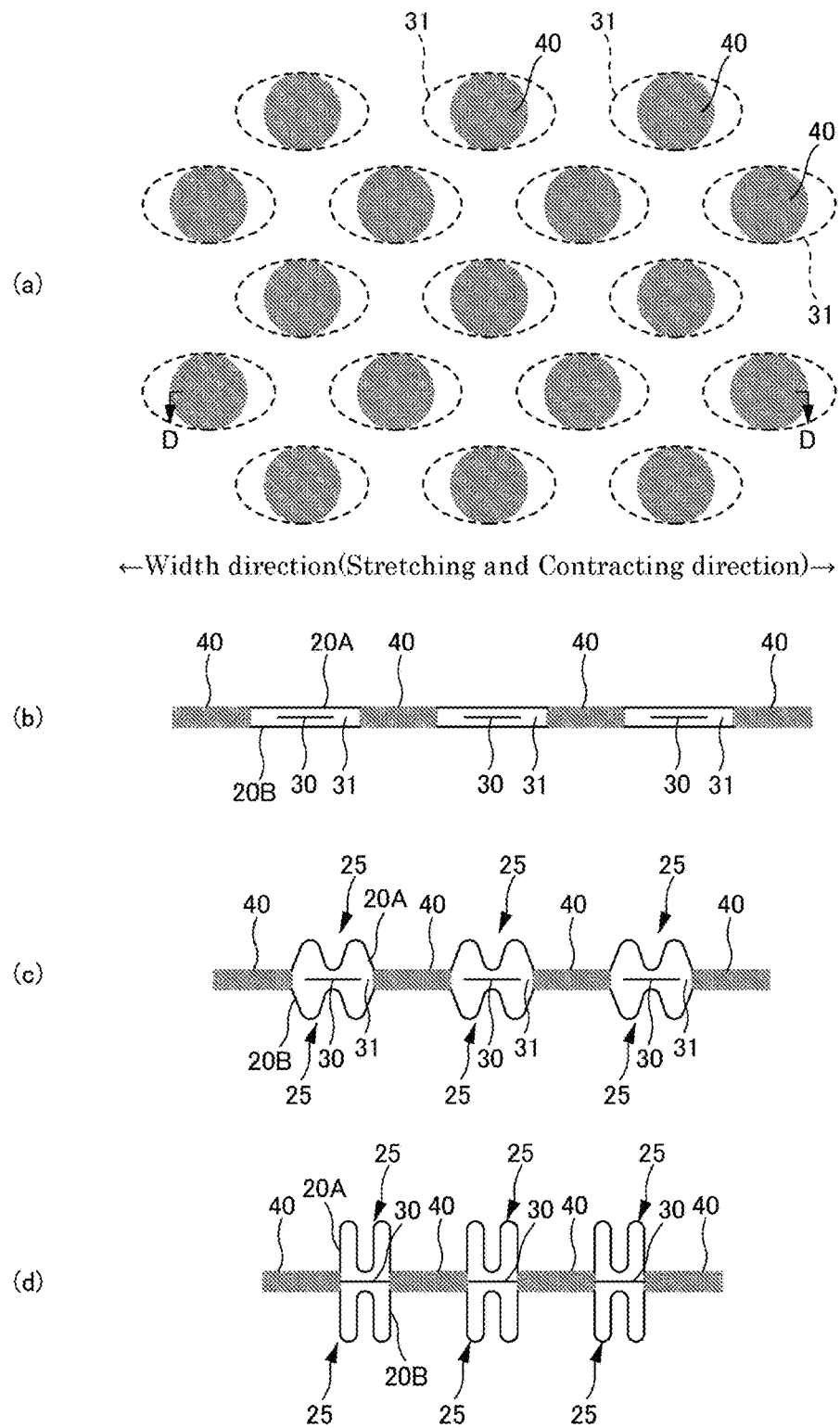
FIG. 3(a) is a plan view of a main part of an outer body.
FIG. 3(b) is a D-D cross-sectional view of FIG. 3(a)
FIG. 3(c) is a cross-sectional view in a worn state.
FIG. 3(d) is a cross-sectional view in a natural length state.

In this embodiment, as shown in FIG. 2, the elastic film stretchable structures 20X are formed in the torso region T of the front body F, the torso region T of the back body B, and an intermediate region L therebetween in the outer body 20. That is, in the stretchable structures 20X of the outer body 20, the non-stretchable region 70 is formed in the intermediate portion in the width direction, which includes parts of the outer body 20 overlapping with the absorber 13 (the non-stretchable region 70 may entirely or partly overlap with the absorber 13 and preferably should contain the substantially entire fixed portion 10B of the inner body) as well as the stretchable regions 80 extend to the side seal portions 21 in the width direction. The elastic film 30 is, as shown in FIG. 3, stacked between the first sheet layer 20A and the second sheet layer 20B over the entire stretchable regions 80 and the non-stretchable region 70, and the first sheet layer 20A and second sheet layer 20B are joined at a large number of sheet bond portions 40 arrayed in the stretching and contracting direction and the perpendicular direction thereto at predetermined intervals via the through holes 31 formed in the elastic film 30 while the elastic film 30 is being stretched in the width direction. In this case, it is desirable that the first sheet layer 20A is not and the second sheet layer 20B is not joined to the elastic film 30 (except for a melted and solidified material described below). However, joining is allowed.

Basically, as the area rate of the sheet bond portions 40 increases in the elastic film stretchable structure 20X, portions contracted by the elastic film 30, of the first sheet layer 20A and the second sheet layer 20B decrease, and the elongation at the elastic limit is likely to decrease. Accordingly, the area rate of the openings of the through holes 31 in the elastic film 30 increases, and thus the proportion of the elastic film 30 continuing in the stretching and contracting direction decreases in a direction orthogonal to the stretching and contracting direction. Accordingly, the contraction force to be generated in stretching decreases, and the risk of rupture of the elastic film 30 increases. In view of such characteristics, the area rate of the sheet bond portions 40 in the non-stretchable region 70 is determined to be larger than that in the stretchable regions 80, such that the elongation at the elastic limit in the stretching and contracting direction is 130% or less (preferably 120% or less, more preferably 100%). In contrast, the area rate of the sheet bond portions 40 in the stretchable regions 80 is determined to be smaller than that in the non-stretchable region 70, such that the elongation at the elastic limit in the stretching and contracting direction is 200% or higher (preferably 265 to 295%).

In the stretchable region 80, as illustrated in FIG. 3(d), when the elastic film 30 is in the natural length state, the first sheet layer 20A and the second sheet layer 20B between the sheet bond portions stretch in a direction away from each other, and thus a contraction wrinkles 25 extending in a direction intersecting the stretching and contracting direction is formed. In a worn state in which the elastic film 30 is stretched to an extent in the width direction, as illustrated in FIG. 3(c), the contraction wrinkles 25 are still remain although the contraction wrinkles 25 are stretched. In addition, as in the illustrated mode, in a case that the first sheet layer 20A is not and the second sheet layer 20B is not joined to the elastic film 30 in a portion other than between the first sheet layer 20A and the second sheet layer 20B in the sheet bond portions 40 in the non-stretchable region 70, as understood from FIG. 3(c) assuming the worn state and FIGS. 3(a) and 3(b) assuming a completely spread state of the first sheet layer 20A and the second sheet layer 20B, a gap is formed between the through hole 31 of each of the sheet bond portions in the elastic film 30 and each of the sheet bond portions 40 in these states, and thus air permeability is imparted due to the gap even when a material of the elastic film 30 is a non-porous film or a non-porous sheet. States of the contraction wrinkles 25 in the worn state and the natural length state are shown in sample photographs of FIGS. 12 to 14.

Figure 12:
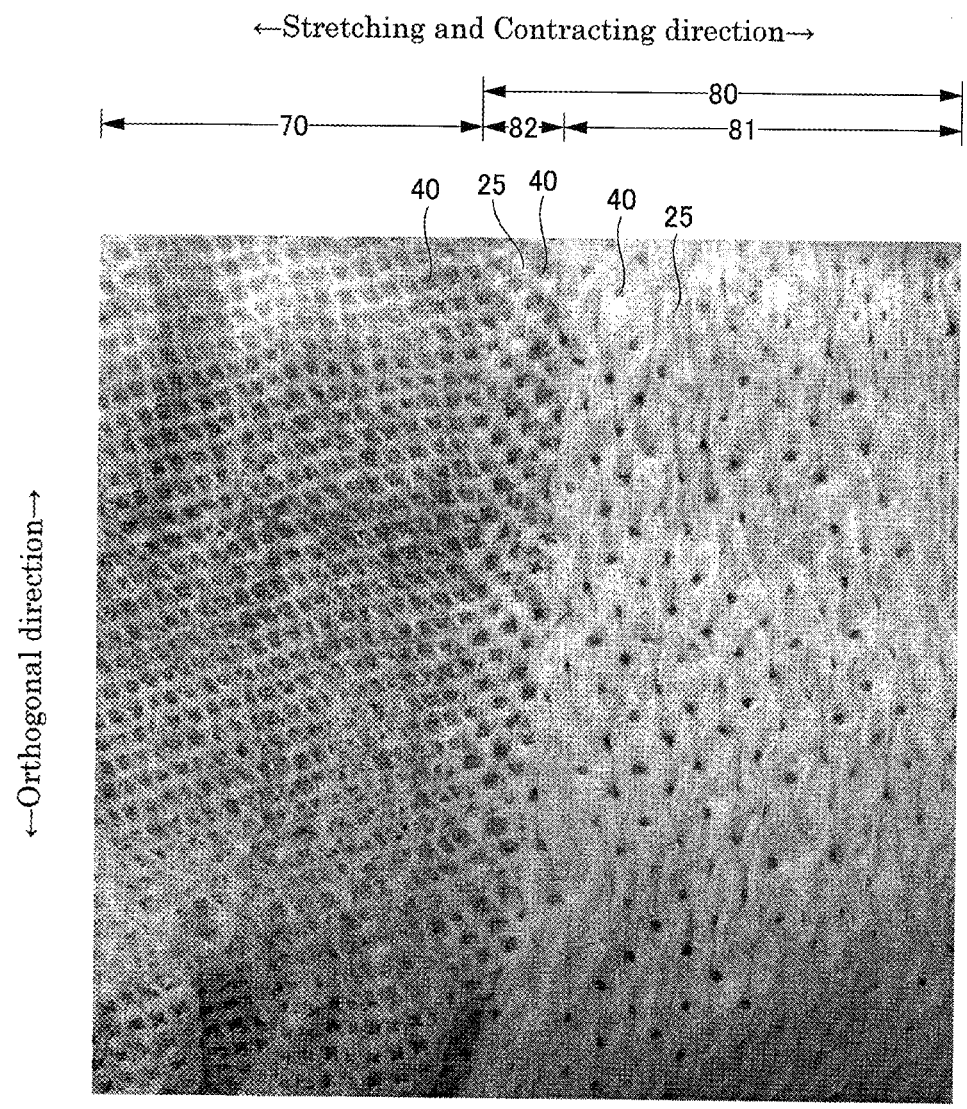
FIG. 12 is a photograph in a natural length state of a sample of an embodiment.
Figure 13:
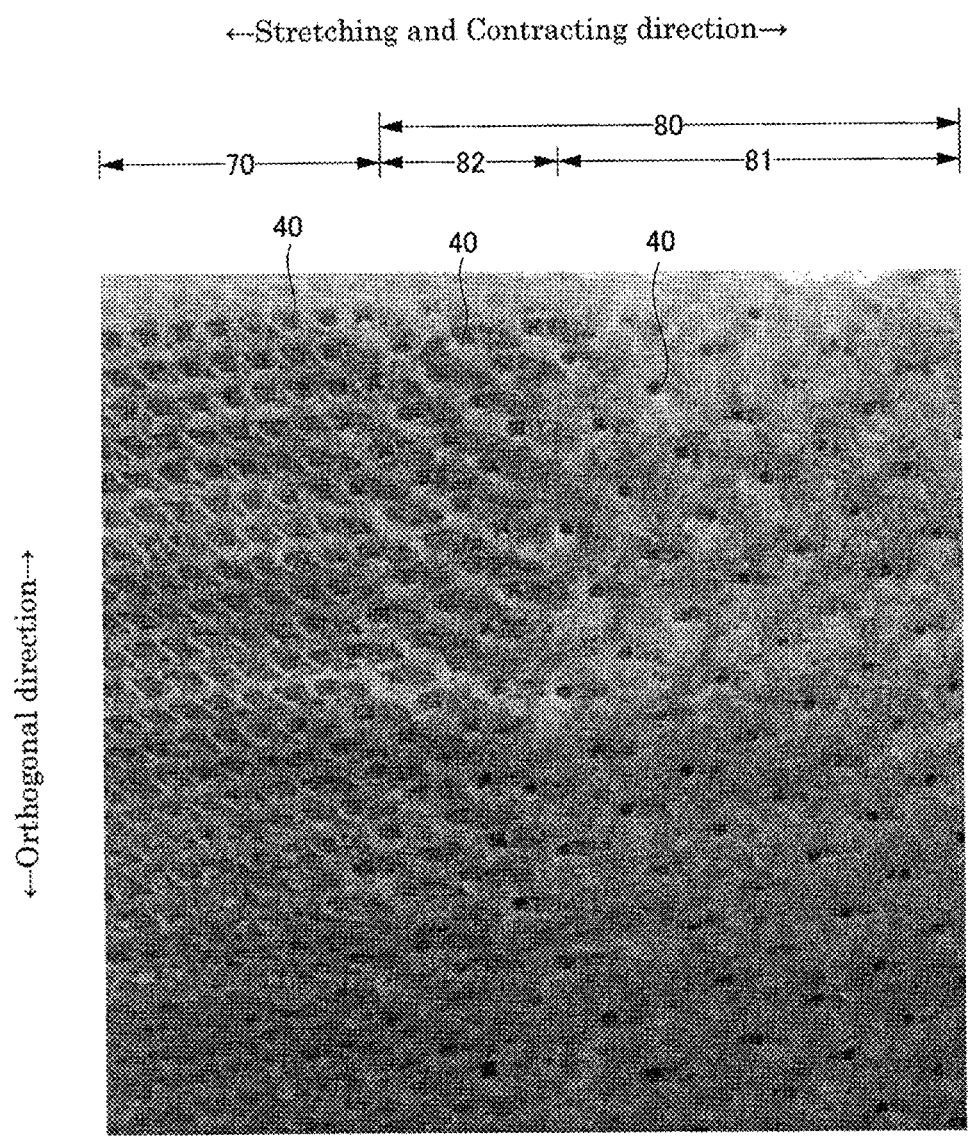
FIG. 13 is a photograph in a stretched state of a sample of an embodiment.
Figure 14:
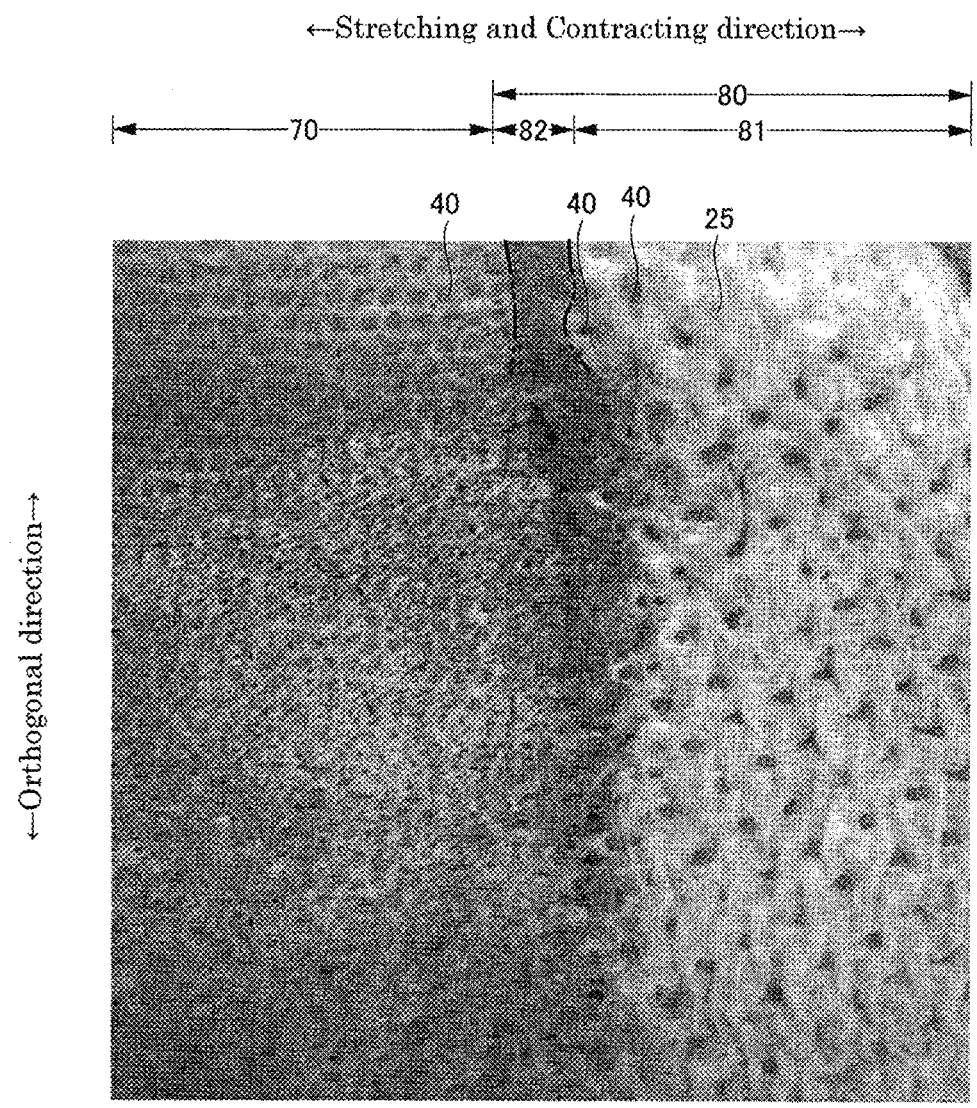
FIG. 14 is a photograph illustrating a natural length state after an elastic film is fractured.

In the non-stretchable region 70, as understood from the sample photographs of FIGS. 12 to 14, a raised portion or an extremely fine wrinkle is formed between the sheet bond portions 40. However, since the area rate of the sheet bond portions 40 is significantly high, elasticity is substantially eliminated.

With reference to FIGS. 2 and 9(a), ends of the stretchable regions 80 adjacent to the non-stretchable regions 70 are set to buffer stretchable sections 82 each having a smaller area rate of the sheet bond portions 40 than that of the remaining sections or main stretchable sections 81 of the stretchable regions 80. When stretched, the buffer stretchable sections 82 are assumed to cause the following variations: In the case where the buffer stretchable sections 82 and the main stretchable sections 81 are stretched from the natural length state by gradually increasing stress, there are the first phase and the second phase. In the first phase, while both of the buffer stretchable sections 82 and the main stretchable sections 81 are stretched, the buffer stretchable sections 82 are stretched to the elastic limit into a completely spread state (illustrated in FIG. 3(b)) earlier than the main stretchable sections 81 and the main stretchable sections 81 are in an incompletely spread state (illustrated in FIG. 3(c)). The main stretchable sections 81 go through the first phase and then the second phase where the main stretchable sections 81 are stretched to the elastic limit into a completely spread state (illustrated in FIG. 3(b)). In the first phase, the buffer stretchable sections 82 having a low elongation at elastic limit are stretched; therefore, a small tension is applied to boundaries between the buffer stretchable sections 82 and the non-stretchable regions 70 of the elastic film 30. Ruptures of the elastic film 30 at the boundaries between the buffer stretchable sections 82 and the non-stretchable regions 70 are thereby prevented. In the second phase, until the main stretchable sections are in a completely spread state, tension corresponding to the elongation of the main stretchable sections 81 is applied to the main stretchable sections 81, the buffer stretchable sections 82, and the non-stretchable regions 70; however, since the buffer stretchable sections 82 cannot be stretched any more after the first phase, and tension applied to the non-stretchable regions 70 and the buffer stretchable sections 82 is entirely supported by the first sheet layer 20A and the second sheet layer 20B. As a result, the tension applied to the boundaries between the buffer stretchable sections 82 and the non-stretchable regions 70 of the elastic film 30 does not exceed the elongation at elastic limit in the first phase. Ruptures of the elastic film 30 along the boundaries between the buffer stretchable sections 82 and the non-stretchable regions 70 are thereby prevented, as in the first phase.

Figure 9:
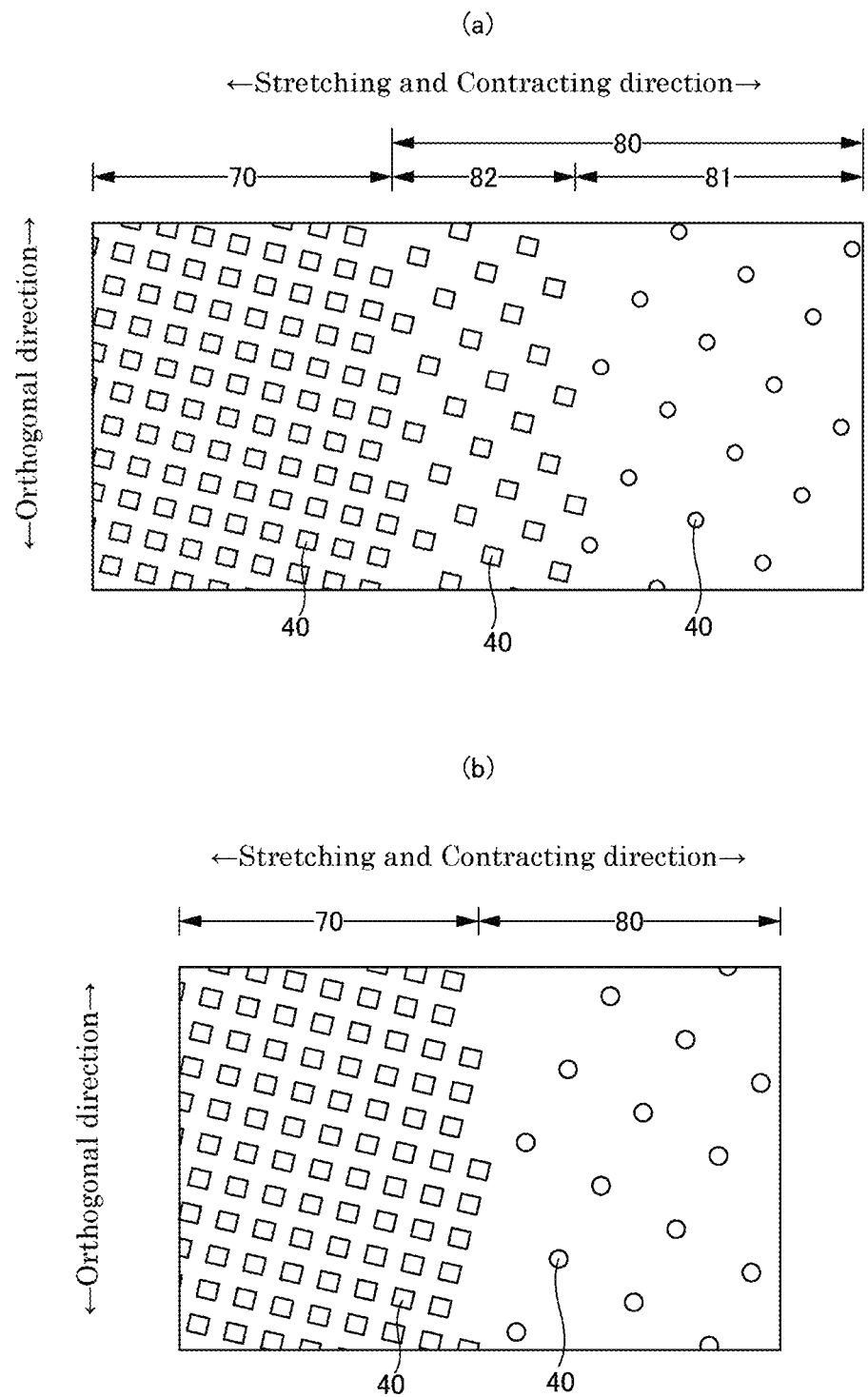
FIG. 9 is a schematic plan view of a main part of the outer body in the completely spread state.

In contrast, if buffer stretchable sections 82 are not provided as illustrated in FIG. 9(*b*), the stretchable region 80 has a high elongation at an elastic limit, and tension applied to the boundary between the stretchable region 80 and the non-stretchable region 70 of the elastic film 30 increases until the boundary between the stretchable region 80 and the non-stretchable region 70 of the elastic film 30 is stretched to the elongation at elastic limit into a completely spread state. The elastic film 30 is thereby likely to rupture along the boundary between the stretchable region 80 and the non-stretchable region 70 (the edges of the ruptured elastic film is indicated by the chain double-dashed lines), as illustrated in FIG. 14.

In view of the principle described above, it is preferred that the elongation at elastic limit of the buffer stretchable section 82 be smaller than a tensile elongation in the stretching and contracting direction of the elastic film 30 having a width equal to an interval between two adjacent through holes 31 formed in the elastic film 30 and arrayed in the direction orthogonal to the stretching and contracting direction and in the non-stretchable region 70, to certainly prevent the rupture of the elastic film 30 at the boundary between the stretchable region 80 and the non-stretchable region 70.

A shape of each of the sheet bond portions 40 and of each of the through holes 31 in the natural length state may be set to an arbitrary shape such as a perfect circle, an ellipse, a polygon such as a rectangle (including a linear shape or a rounded corner), a star shape, a cloud shape, etc. A size of each of the sheet bond portions 40 may be appropriately determined. At an excessively large size, the hardness of the sheet bond portions 40 significantly affects the touch, whereas at an excessively small size, the bonded area is too small to certainly bond the layers. Each of the sheet bond portions 40 preferably has an area of approximately 0.14 to 3.5 mm$^2$, in usual cases. Each of the through holes 31 should have an opening area larger than that of the corresponding sheet bond portion 40 such that the sheet bond portion 40 is formed within the through hole 31. The through hole 31 preferably has an opening area of approximately 1 to 1.5 times the area of the sheet bond portion 40.

In general, the area and the area rate of each of the sheet bond portions 40 in each region are preferably set as below.

Non-Stretchable Region 70

Area of each of sheet bond portions 40: 0.14 to 3.5 mm$^2$ (particularly 0.25 to 1.0 mm$^2$)

Area rate of sheet bond portions 40: 16 to 45% (particularly 25 to 45%)

Main Stretchable Section 81

Area of each of sheet bond portions 40: 0.14 to 3.5 mm$^2$ (particularly 0.14 to 1.0 mm$^2$)

Area rate of sheet bond portions 40: 1.8 to 19.1% (particularly 1.8 to 10.6%)

Buffer Stretchable Section 82

Area of each of sheet bond portions 40: 0.14 to 3.5 mm$^2$ (particularly 0.25 to 1.0 mm$^2$)

Area rate of sheet bond portions 40: 8 to 22.5% (particularly 12.5 to 22.5%)

Figure 10:
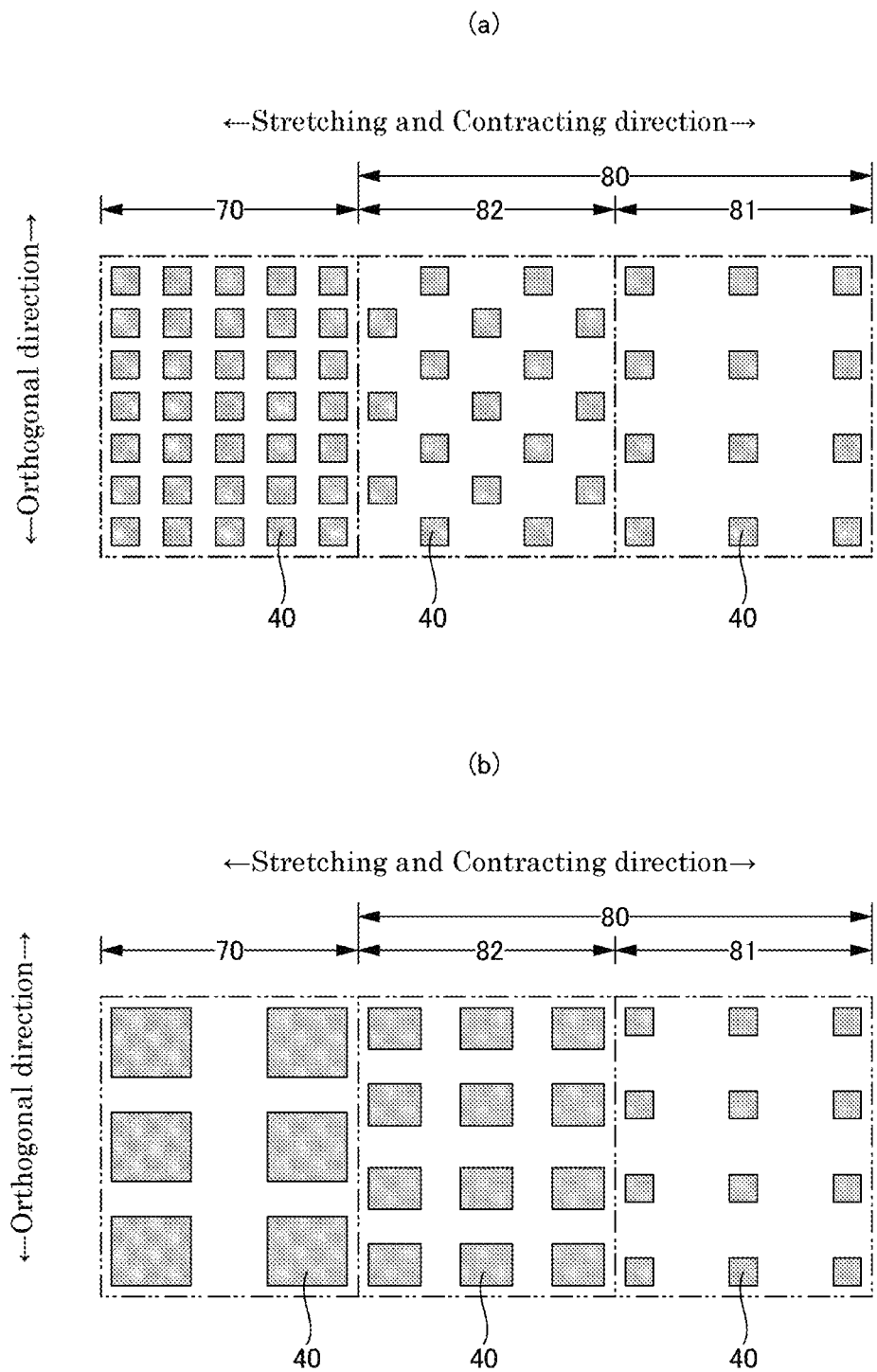
FIG. 10 is an enlarged plan view of a main part illustrating a pattern of sheet bond portions.

To produce three fields (i.e., the non-stretchable region 70, the main stretchable section 81, and the buffer stretchable section 82) having different area rates, the number of the sheet bond portions 40 per unit area may be varied, as illustrated in FIG. 10(*a*), or the area of each of the sheet bond portions 40 may be varied, as illustrated in FIG. 10(*b*). In the former case, the areas of the sheet bond portions 40 may be the same between two or more fields of the non-stretchable region 70, the main stretchable section 81, and the buffer stretchable section 82, or may be different among all the fields. In the latter case, the number of the sheet bond portions 40 per unit area may the same between two or more fields of the non-stretchable region 70, the main stretchable section 81, and the buffer stretchable section 82, or may be different among all the fields.

The planar geometries of the sheet bond portions 40 and the through holes 31 may be appropriately determined. Preferred is regularly repeated geometry, such as an oblique lattice illustrated in FIG. 19(*a*), hexagonal lattice (also referred to as staggered lattice) illustrated in FIG. 19(*b*), square lattice illustrated in FIG. 19(*c*), rectangular lattice illustrated in FIG. 19(*d*), or parallel tope lattice illustrated in FIG. 19(*e*) (where two groups of a large number of diagonally parallel arrays intersect each other, as shown in the drawings) (including arrays tilted by less than 90 degrees to the stretching and contracting direction). Alternatively, the sheet bond portions 40 may be arrayed in regularly repeated groups (the geometry of each group may be regular or irregular, in other words, may be in a pattern or characteristic letters, for example). The geometries of the sheet bond portions 40 and the through holes 31 may be the same or different among the main stretchable section 81, the buffer stretchable section 82, and the non-stretchable region 70.

Figure 11:
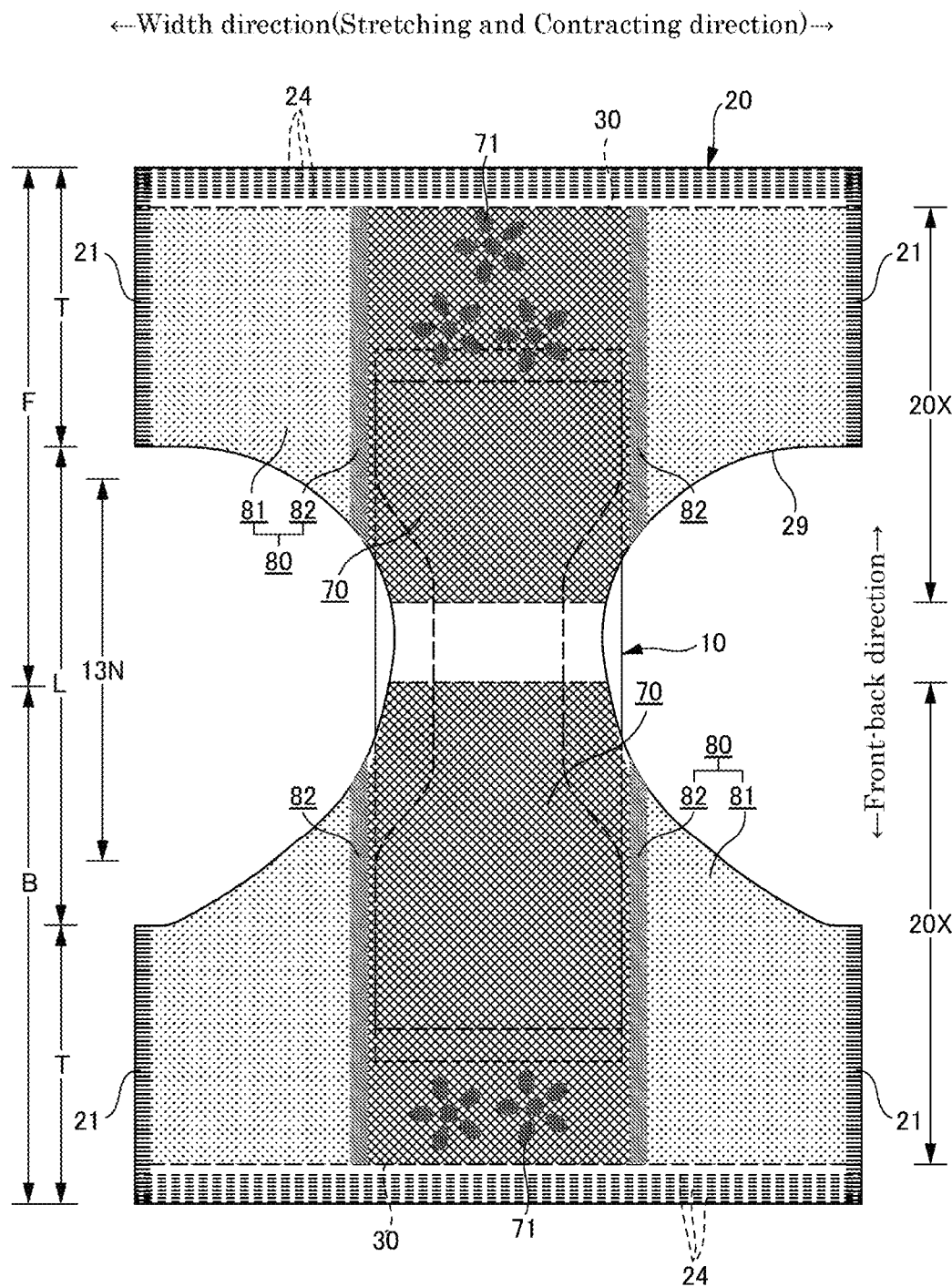
FIG. 11 is a plan view (external surface side) of an underpants-type disposable diaper in a completely spread state.

As illustrated in FIG. 11, in addition to the portion overlapping the absorber 13, for example, it is possible to provide the non-stretchable region 70 in which the sheet bond portions 40 are disposed in a shape of an indication 71. In this case, the buffer stretchable section may be provided in the stretchable region 80 continuing from the non-stretchable region 70. The indication 71 may correspond to an indication known in a field of the absorbent article, for example, a pattern for decoration (including a tiny picture or a character), a function indicator such as a usage method, usage assistance, a size, etc., or a mark indication such as a manufacturer, a product name, a characteristic function, etc. In an illustrated mode, the applied indication 71 is a flower pattern corresponding to a plant pattern. However, it is possible to use various types of patterns such as an abstract pattern, an animal pattern, and a natural phenomenon pattern.

The elastic film 30 may be composed of any resin film having elasticity. For example, it is possible to use a film obtained by processing a blend of one or two or more types of thermoplastic elastomers such as a styrene type elastomer, an olefin type elastomer, a polyester type elastomer, a polyamide type elastomer, a polyurethane type elastomer, etc. in a film shape using extrusion molding such as a T-die method, an inflation method, etc. In addition, it is possible to use a film in which a large number of holes or slits are formed for ventilation in addition to a nonporous film. In particular, it is preferable when the elastic film 30 has a tensile strength in the stretching and contracting direction of 8 to 25 N/35 mm, tensile strength in the direction orthogonal to the stretching and contracting direction of 5 to 20 N/35 mm, tensile elongation in the stretching and contracting direction of 450 to 1,050%, and tensile elongation in the direction orthogonal to the stretching and contracting direction of 450 to 1,400%. The thickness of the elastic film 30 is not particularly restricted. However, the thickness is preferably in a range of about 20 to 40 μm. In addition, the basis weight of the elastic film 30 is not particularly restricted. However, the basis weight is preferably in a range of about 30 to 45 g/m$^2$, and particularly preferably in a range of about 30 to 35 g/m$^2$.

Characteristically, as illustrated in FIG. 8(a), the first sheet layer 20A and the second sheet layer 20B in the sheet bond portions 40 are joined at least by a melted and solidified material 30m of the elastic film 30 among the first sheet layer 20A and the second sheet layer 20B. When the first sheet layer 20A and the second sheet layer 20B are joined using the melted and solidified material 30m of the elastic film 30 as an adhesive in this way, a peeling strength becomes high, and it is possible to achieve both high air permeability and high peeling strength as understood from Example below.

Figure 15:
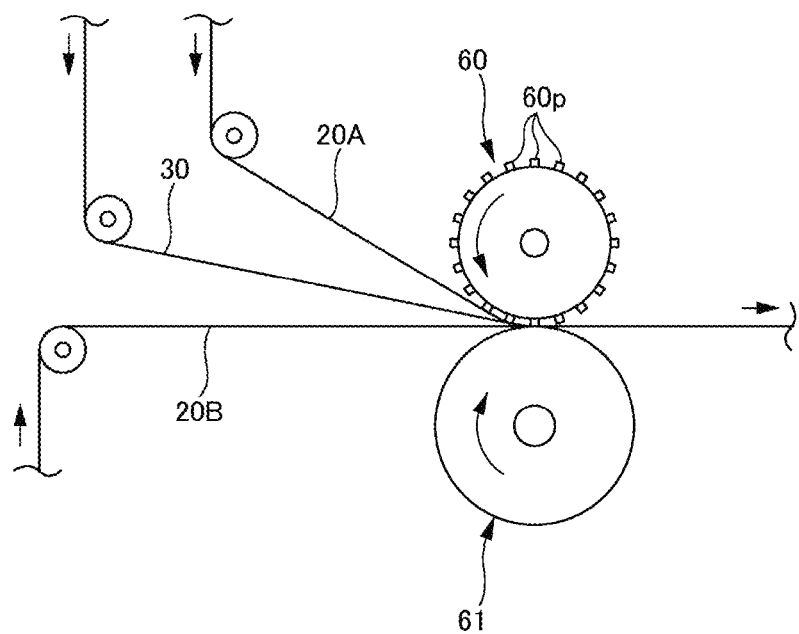
FIG. 15 is a schematic view of a welding process.
Figure 16:
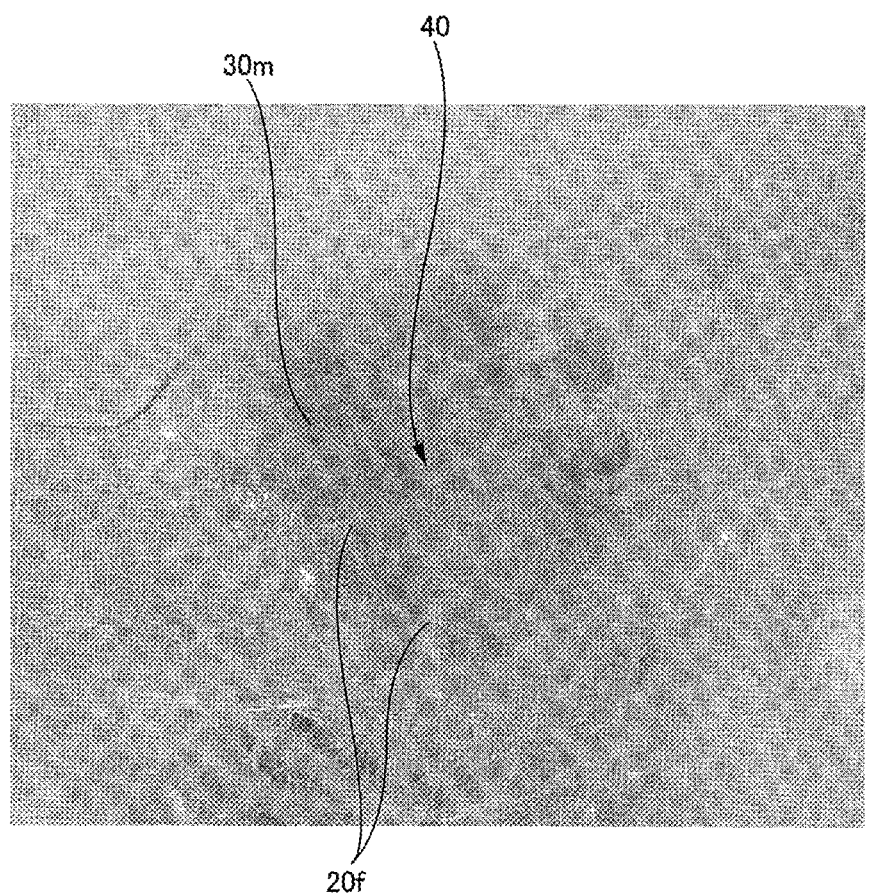
FIG. 16 is an enlarged photograph of a sheet bond portion.
Figure 17:
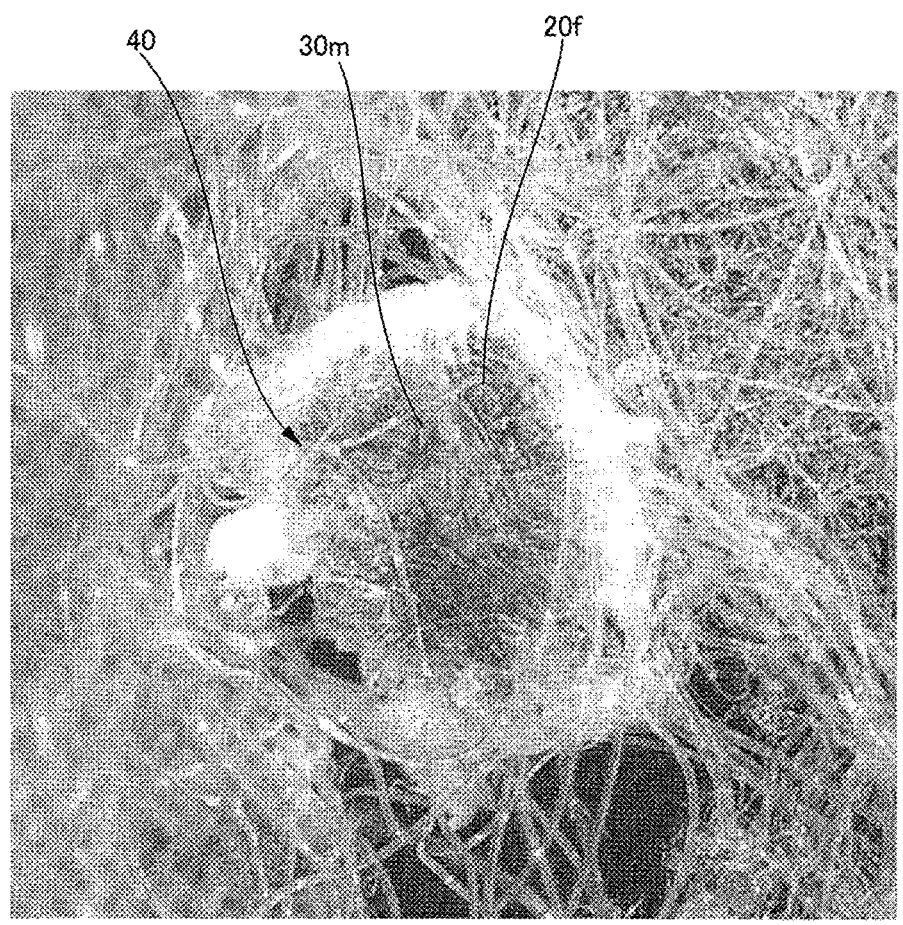
FIG. 17 is an enlarged photograph of a sheet bond portion in a state in which a first sheet layer and a second sheet layer are peeled.

In such a joining structure, for example, as illustrated in FIG. 15, when welding is performed in a predetermined pattern of the sheet bond portions 40 in a state in which the elastic film 30 is interposed between the first sheet layer 20A and the second sheet layer 20B while being stretched in the stretching and contracting direction, the elastic film 30 may be melted at a large number of positions to form the through holes 31, and manufacture may be simply and efficiently performed using a method of joining the first sheet layer 20A and the second sheet layer 20B by at least solidification of the melted material of the elastic film 30 at positions of the through holes 31. In this case, in the natural length state, the shape/area of each of the sheet bond portions 40 are substantially equal to the shape/area of each of the through holes 31. FIG. 15 illustrates an example using a heat sealing device. A material to be processed, while in the material, the elastic film 30 is interposed between the first sheet layer 20A and the second sheet layer 20B, is fed between a seal roll 60 having a large number of pressing protrusions 60p arranged in the above pattern of the sheet bond portions 40 on an outer surface thereof and an anvil roll 61 which is disposed to face the seal roll 60 and has a smooth surface, and the pressing protrusions 60p are heated. In this way, the elastic film 30 is melted only where pressed in the thickness direction between the pressing protrusions 60p and an outer surface of the anvil roll 61 to form the through holes 31, and the first sheet layer 20A and the second sheet layer 20B are joined at least by the solidification of the melted material of the elastic film 30 at the positions of the through holes 31. However, another device such as ultrasonic sealing may be used as long as the elastic film 30 is melted in a desired pattern to form the through holes 31, and the first sheet layer 20A and the second sheet layer 20B are joined at least by solidification of the melted material of the elastic film 30 at the positions of the through holes 31.

It is possible to appropriately determine a relation of a melting point of the elastic film 30, melting points of the first sheet layer 20A and the second sheet layer 20B, and a processing temperature at a welding position. However, rather than to set the melting points of the first sheet layer 20A and the second sheet layer 20B to be lower than or equal to the melting point of the elastic film 30, melt and combine the whole of the first sheet layer 20A and the second sheet layer 20B and the whole elastic film 30 at the welding positions, and form the sheet bond portions 40, it is preferable to set the melting points of the first sheet layer 20A and the second sheet layer 20B to be higher than the melting point of the elastic film 30, melt the elastic film 30 at the welding position, and not to melt a part of the first sheet layer 20A and the second sheet layer 20B or not to melt a whole of the first sheet layer 20A and the second sheet layer 20B. In other words, as understood from FIG. 16 and FIG. 17, a latter case corresponds to a structure in which fibers 20f of the first sheet layer 20A and the second sheet layer 20B continuing from around the sheet bond portions 40 are left, and the first sheet layer 20A and the second sheet layer 20B are joined by the melted and solidified material 30m of the elastic film 30, which has infiltrated and solidified among the first sheet layer 20A and the second sheet layer 20B. Further, improved adhering of the melted and solidified material of the elastic film to the first sheet layer and the second sheet layer is obtained, and strength of the first sheet layer 20A and the second sheet layer 20B rarely decreases. Thus, peeling strength is further enhanced. This situation in which "a part of the first sheet layer 20A and the second sheet layer 20B is not melted" includes a mode in which for all fibers of the sheet bond portions, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

From this point of view, the melting point of the elastic film 30 is preferably about 80 to 145° C., the melting points of the first sheet layer 20A and the second sheet layer 20B are preferably about 85 to 190° C., particularly, 150 to 190° C., and a difference between the melting points of the first sheet layer 20A and the second sheet layer 20B and the melting point of the elastic film 30 is preferably about 60 to 80° C.

In the illustrated example, the elastic film stretchable structure 20X is applied to a stretchable structure, which is provided in the outer body 20 excluding the waist end portion region. However, appropriate changes are allowed. For example, the waist end portion region may be included to which the elastic film stretchable structure 20X is applied as in modes illustrated in FIG. 20 to FIG. 22 described below, or it is possible to adopt a mode in which the elastic film stretchable structure 20X is not provided in the intermediate region L between the torso region T of the front body F and the torso region T of the back body B. In addition, the above-described stretchable structure 20X may be applied to another elastic portion such as a three-dimensional gather, a plane gather, etc. generally used for a waist, a fastening tape, and an absorbent article of a tape-type disposable diaper in addition to the underpants-type disposable diaper. In addition, even though the non-stretchable region is included in the present embodiment, it is possible to adopt a mode in which the whole elastic film stretchable structure is used as the stretchable region and the non-stretchable region is not included. Furthermore, even though the stretching and contracting direction is regarded as the width direction in the illustrated example, the stretching and contracting direction may be set to the front-back direction or set to both the width direction and the front-back direction.

Peeling Test

Figure 18:
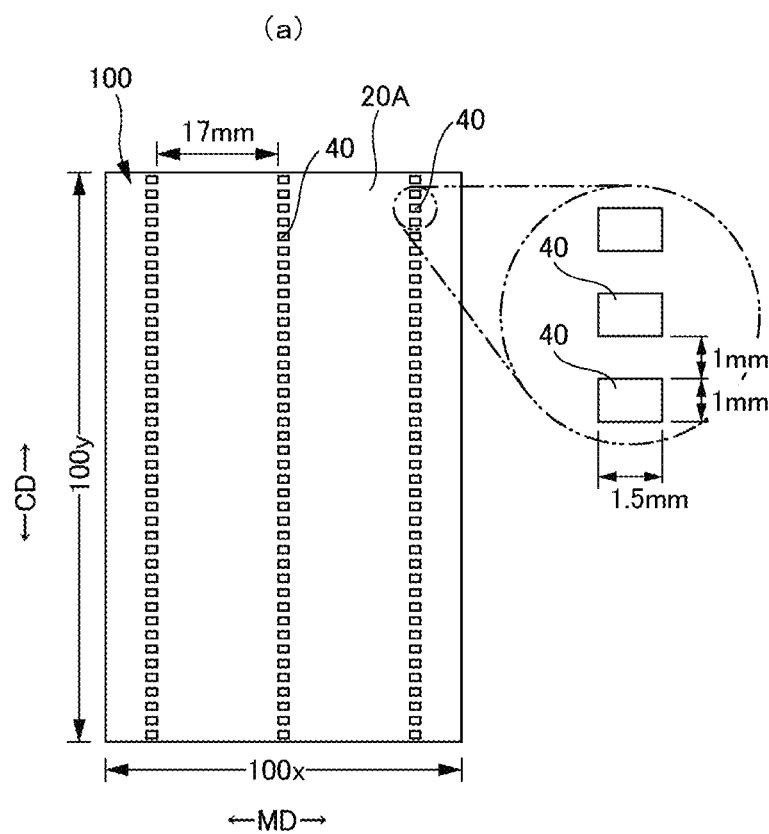
FIG. 18 is an overview explanatory diagram of a peeling test.
Figure 18:
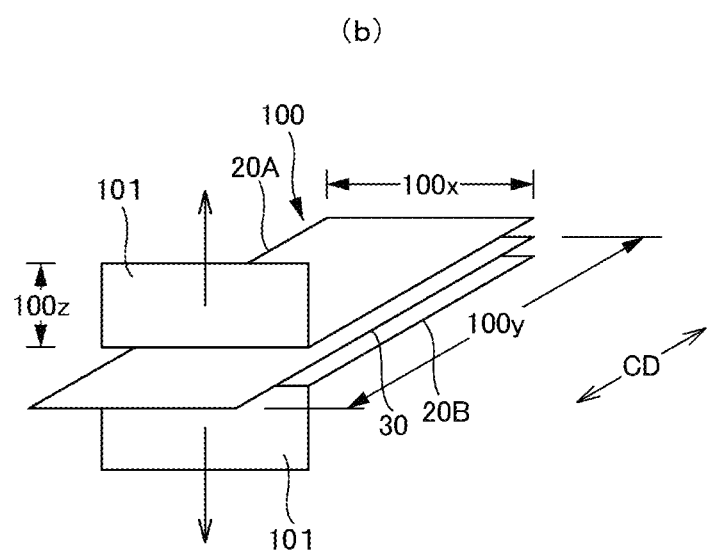
Figure 19:
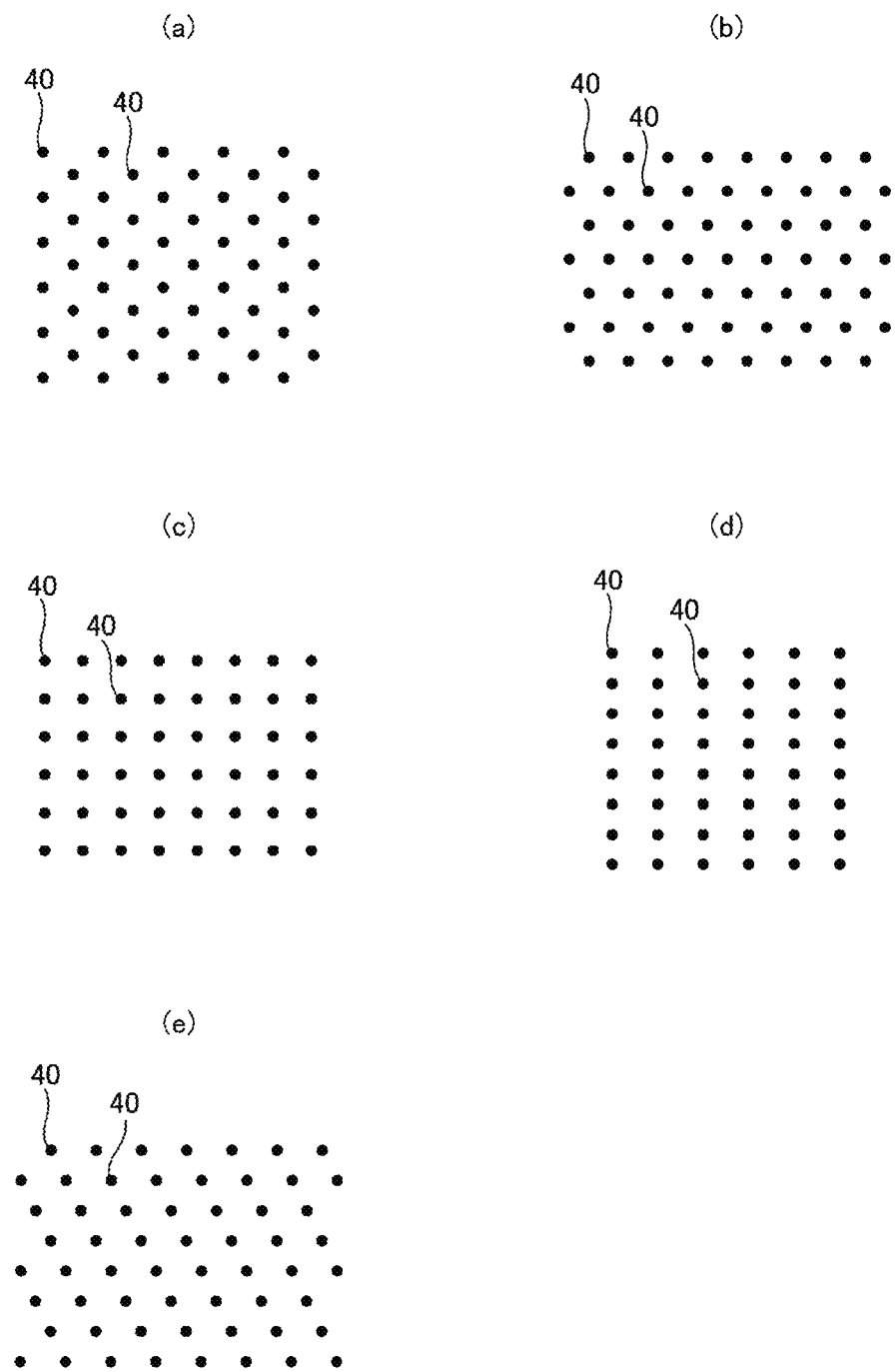
FIG. 19 is a plan view illustrating various arrangement examples of the sheet bond portions.

The first sheet layer and second sheet layer used were spun bond nonwoven fabric having a basis weight of 17 g/m² made of PE/PP conjugate fiber (core: polypropylene (melting point, 165° C.), sheath: polyethylene (melting point, 130° C.)). The elastic film used had a basis weight of 35 g/m², thickness of 35 μm, and a melting point in the range of 110 to 120° C. The elastic film in a natural length state (the natural state or stretched state does not affect the relative comparison of the peel strength) was disposed between the first and second sheet layers in the same machine direction (MD). With reference to FIG. 18($a$), rectangular sheet bond portions 40 having long sides in the MD (short side: 1.0 mm, long side: 1.5 mm) are formed at an interval of 1 mm in the cross direction (CD) perpendicular to the MD and an interval of 17 mm in the MD with a stapler-type ultrasonic sealing machine (HARURU SUH-30 available from SUZUKI). A sample 100 provided with the elastic film having a CD length 100$y$ of 80 mm and a MD length 100$x$ of 50 mm was thereby produced (inventive example). The same operator carried out ultrasonic sealing for a pressuring time of about three seconds under the same pressure also for obtaining a similar joining state to that in the photograph illustrated in FIG. 16. The MD of the nonwoven fabric represents the direction of the orientation of the nonwoven fabric (the fibers of the nonwoven fabric are oriented in the MD), and can be determined, for example, by a method of testing the orientation of fiber by a zero-distance tensile strength in accordance with a TAPPI standard T481 or a simplified testing methods that determines the direction of the orientation from the ratio of the tensile strengths of the front-back direction to the width direction.

A sample was prepared in the same way as in the inventive example except a double layered structure free from the elastic film was used (comparative example). The structure of the sample free from the elastic film is regarded as the structure shown in Patent Literature 1 in which the first sheet layer is joined to second sheet layer without an elastic film, in terms of peel strength.

With reference to FIG. 18($b$), the first and second sheet layers were each manually peeled by a length 101$z$, 30 mm, from one end in the CD, each of the samples 100 has the laminated stretchable structures, the released portions 101 were clamped with chucks for a tensile tester, and peeling of the remaining 50 mm of the first and second sheet layers was re-started from the above mentioned 30 mm position at a chuck interval of 50 mm and a speed of testing of 300 mm/min in the stretching and contracting direction. The observed maximum tensile stress was defined as peel strength. The testing machine was a universal TENSILON tester RTC-1210A available from ORIENTEC.

The results demonstrate that the inventive sample has a significantly high peel strength of 10.2N, whereas the comparative sample has a peel strength of 2.7N.

With Regard to Mode for Solve Second Problem

Figure 22:
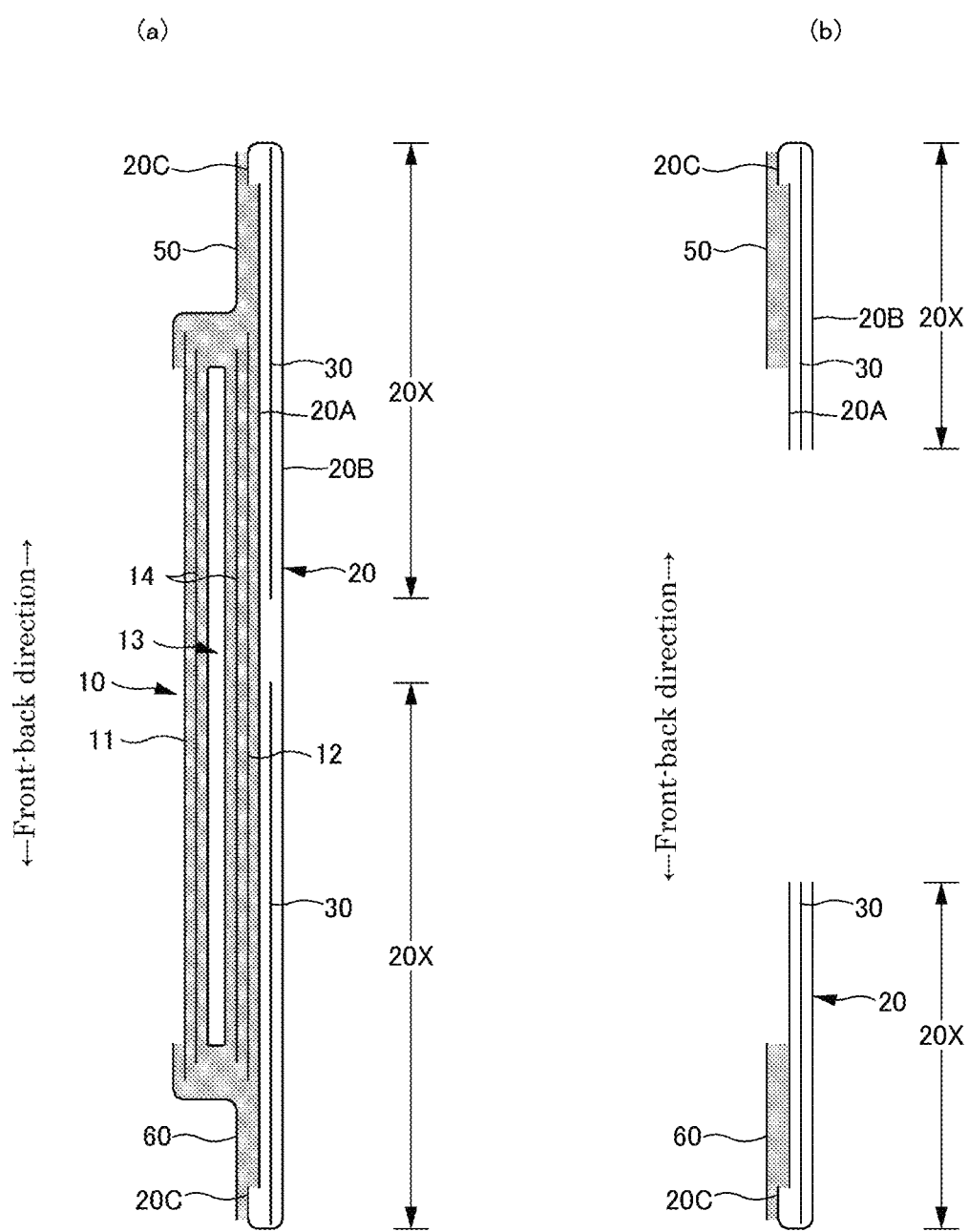
FIG. 22(a) is a C-C cross-sectional view of FIG. 20.
FIG. 22(b) is an E-E cross-sectional view of FIG. 1.
Figure 23:
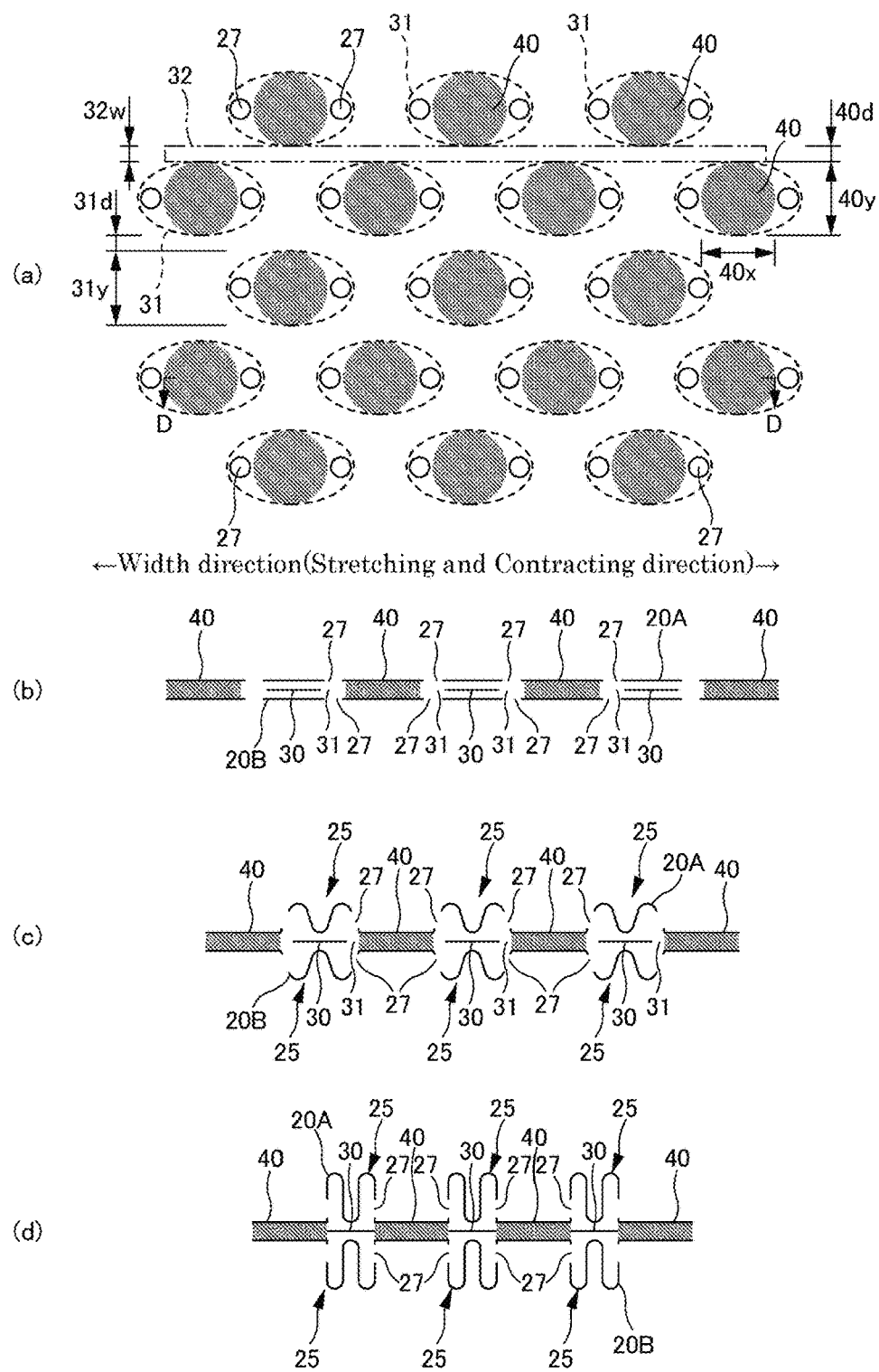
FIG. 23(a) is a plan view of a main part of the stretchable region.
FIG. 23(b) is a D-D cross-sectional view of FIG. 23(a)
FIG. 23(c) is a cross-sectional view in the worn state.
FIG. 23(d) is a cross-sectional view in the natural length state.

Now, a mode for solving the second problem will be described with reference to FIG. 3 to FIG. 7 and FIG. 19 to FIG. 30. As long as the outer body 20 is extended to a lateral side of the side edge of the absorber 13, in the crotch portion, aside edge of the outer body 20 may be positioned closer to a central side than a side edge of the inner body 10 in the width direction as in the illustrated mode, or may be positioned closer to an outer side than that in the width direction. The outer body 20 has torso regions T each defined by a front-back direction range corresponding to a range of the side seal portion 21, and an intermediate region L corresponding to a front-back direction range between the torso region T of the front body F and the torso region T of the back body B. Further, in the outer body 20 of the illustrated mode, except for the middle of the intermediate region L in the front-back direction, an elastic film 30 is stacked between a first sheet layer 20A and a second sheet layer 20B as illustrated in FIG. 22, and the first sheet layer 20A and the second sheet layer 20B have an elastic film stretchable structure 20X with a stretching and contracting direction in the width direction, and they are joined via through holes 31 penetrating the elastic film 30 at a large number of sheet bond portions 40 arranged at intervals as illustrated in FIG. 23. A planar shape of the outer body 20 is formed by a concave leg line 29 such that each of both side edges of the intermediate region L in the width direction forms a leg opening, and corresponds to a pseudo-hourglass shape as a whole. The outer body 20 may be divided into two front and back parts, and the both parts may be separated from each other in the front-back direction in the crotch portion.

Figure 20:
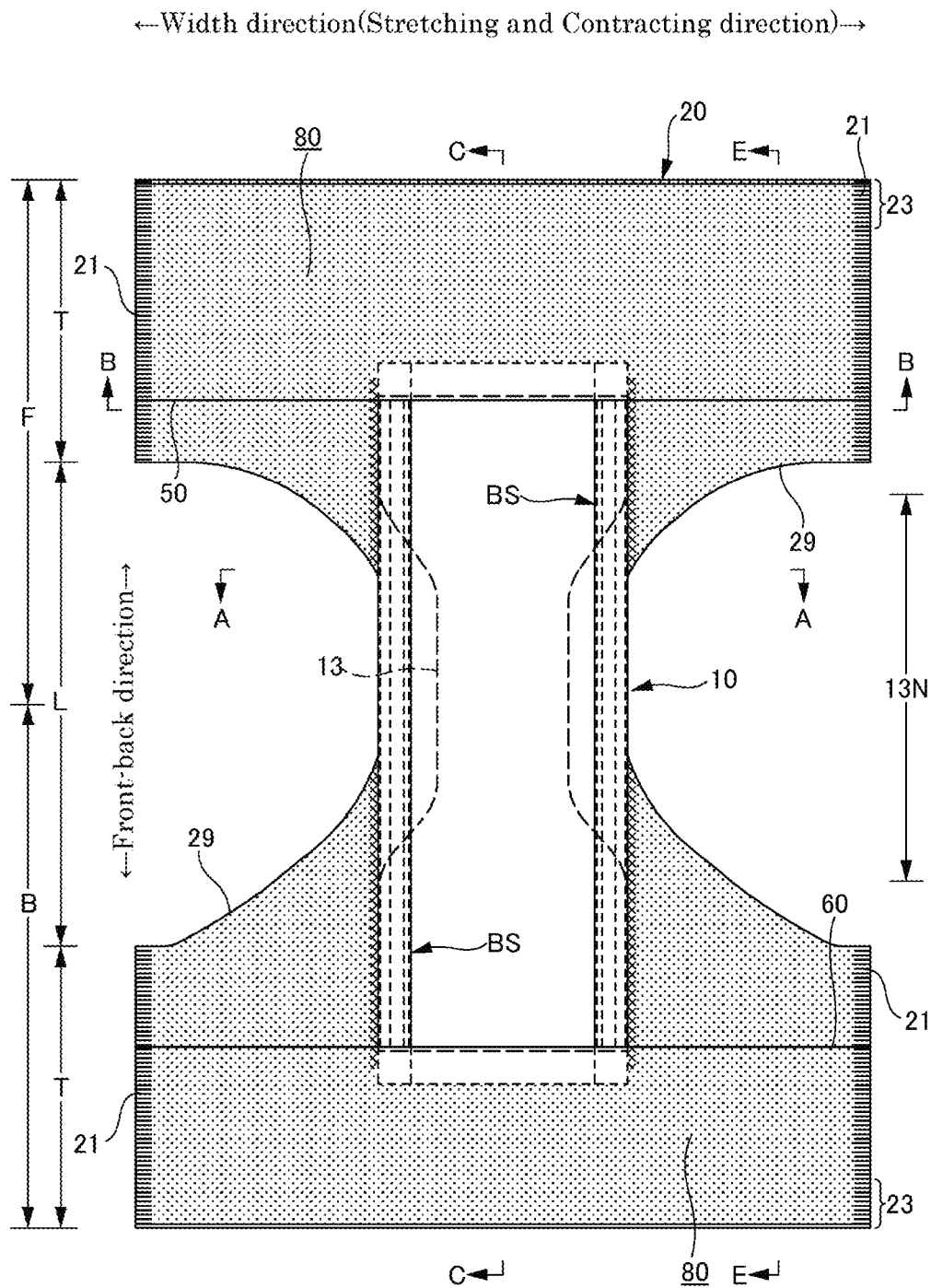
FIG. 20 is a plan view (internal surface side) of an underpants-type disposable diaper in a spread state.
Figure 21:
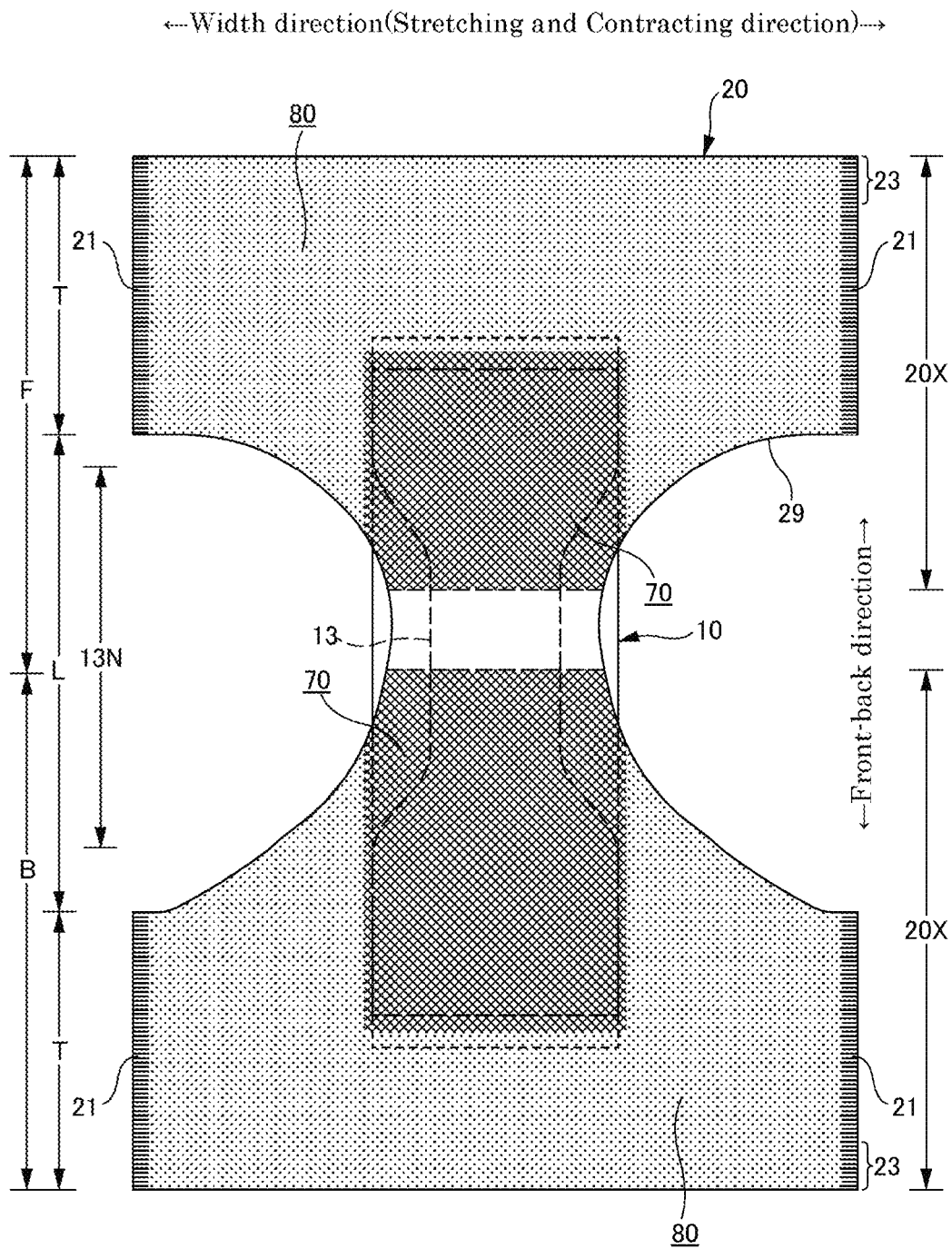
FIG. 21 is a plan view (external surface side) of the underpants-type disposable diaper in the spread state.

The modes illustrated in FIG. 20 and FIG. 21 correspond to a mode in which the elastic film stretchable structure 20X extends to the waist end portion region 23. However, when the elastic film stretchable structure 20X is used in the waist end portion region 23, tightening of the waist end portion region 23 is insufficient. It is possible to provide a stretchable structure according to a conventional elongated waist portion elastic member 24 as necessary without providing the elastic film stretchable structure 20X in the waist end portion region 23 as the modes illustrated in FIG. 31 and FIGS. 1 to 4. The waist portion elastic members 24 correspond to elongated elastic members such as a plurality of rubber threads disposed at intervals in the front-back direction, and apply a stretching force to tighten around the waist of the body. The waist portion elastic members 24 are not disposed substantially in a bundle with a close spacing, and three or more, preferably five or more members are disposed at intervals of about 3 to 8 mm to form a predetermined stretchable zone. A stretch rate of the waist portion elastic member 24 in fixing may be appropriately determined. However, the stretch rate may be set to about 230 to 320% in the case of normal adult use. Rubber threads are used as the waist portion elastic member 24 in an illustrated example. However, for example, another elongated elastic member such as flat rubber may be used.

As another mode, although not illustrated, the elastic film stretchable structure 20X may not be provided in the intermediate region L between the torso region T of the front body F and the torso region T of the back body B, the stretchable structure 20X may be continuously provided in the front-back direction from the inside of the torso region T of the front body F to the inside of the torso region T of the back body B through the intermediate region L, or the elastic film stretchable structure 20X may be provided only in any one of the front body F and the back body B.

A shape of each of the sheet bond portions 40 and the through holes 31 in a natural length state may be appropriately determined. However, it is possible to adopt an arbitrary shape such as a perfect circle (see FIG. 23 and FIG. 24), an ellipse, a polygon such as a triangle, a rectangle (see FIG. 25 to FIG. 28), a rhombus (see FIG. 29(b)), etc., a convex lens shape (see FIG. 29(a)), a concave lens shape (see FIG. 30(a)), a star shape, a cloud shape, etc. The dimensions of each of the sheet bond portions are not particularly restricted. However, a maximum length 40x is preferably set to 0.5 to 3.0 mm, particularly 0.7 to 1.1 mm, and a maximum width is preferably set to 0.1 to 3.0 mm, particularly 0.1 to 1.1 mm in a case of a shape which is long in a direction orthogonal to the stretching and contracting direction.

A size of each of the sheet bond portions 40 may be appropriately determined. However, when the size is excessively large, an influence of hardness of the sheet bond portions 40 on a sense of touch increases. When the size is excessively small, a joining area is small, and materials may not be sufficiently attached to each other. Thus, in general, an area of each of the sheet bond portions 40 is preferably set to about 0.14 to 3.5 mm$^2$. An area of an opening of each of the through holes 31 may be greater than or equal to that of the sheet bond portions since the sheet bond portions are formed via the through holes 31. However, the area is preferably set to about 1 to 1.5 times the area of each of the sheet bond portions. The area of the opening of each of the through holes 31 refers to a value in a natural length state and in a state of being integrated with the first sheet layer 20A and the second sheet layer 20B rather than a state of the elastic film 30 alone, and refers to a minimum value in a case in which the area of the opening of each of the through holes 31 is not uniform in a thickness direction such as a case in which the area is different between a front and a back of the elastic film 30.

The planar geometries of the sheet bond portions 40 and the through holes 31 may be appropriately determined as stated before. Preferred is regularly repeated geometry, such as an oblique lattice illustrated in FIG. 19(a), hexagonal lattice (also referred to as staggered lattice) illustrated in FIG. 19(b), square lattice illustrated in FIG. 19(c), rectangular lattice illustrated in FIG. 19(d), or parallel tope lattice illustrated in FIG. 19(e) (where two groups of a large number of diagonally parallel arrays intersect each other, as shown in the drawings) (including arrays tilted by less than 90 degrees to the stretching and contracting direction). Alternatively, the sheet bond portions 40 may be arrayed in regularly repeated groups (the geometry of each group may be regular or irregular, in other words, may be in a pattern or characteristic letters, for example).

In the sheet bond portions 40, the first sheet layer 20A and the second sheet layer 20B are joined via the through holes 31 formed in the elastic film 30. In this case, it is preferable that the first sheet layer 20A is not and the second sheet layer 20B is not joined to the elastic film 30 in a portion other than at least between the first sheet layer 20A and the second sheet layer 20B in the sheet bond portions 40.

Joining means for the first sheet layer 20A and the second sheet layer 20B in the sheet bond portions 40 is not particularly restricted. For example, the first sheet layer 20A and the second sheet layer 20B in the sheet bond portions 40 may be joined using a hot-melt adhesive or joining means based on material welding such as heat sealing, ultrasonic sealing, etc.

Figure 32:
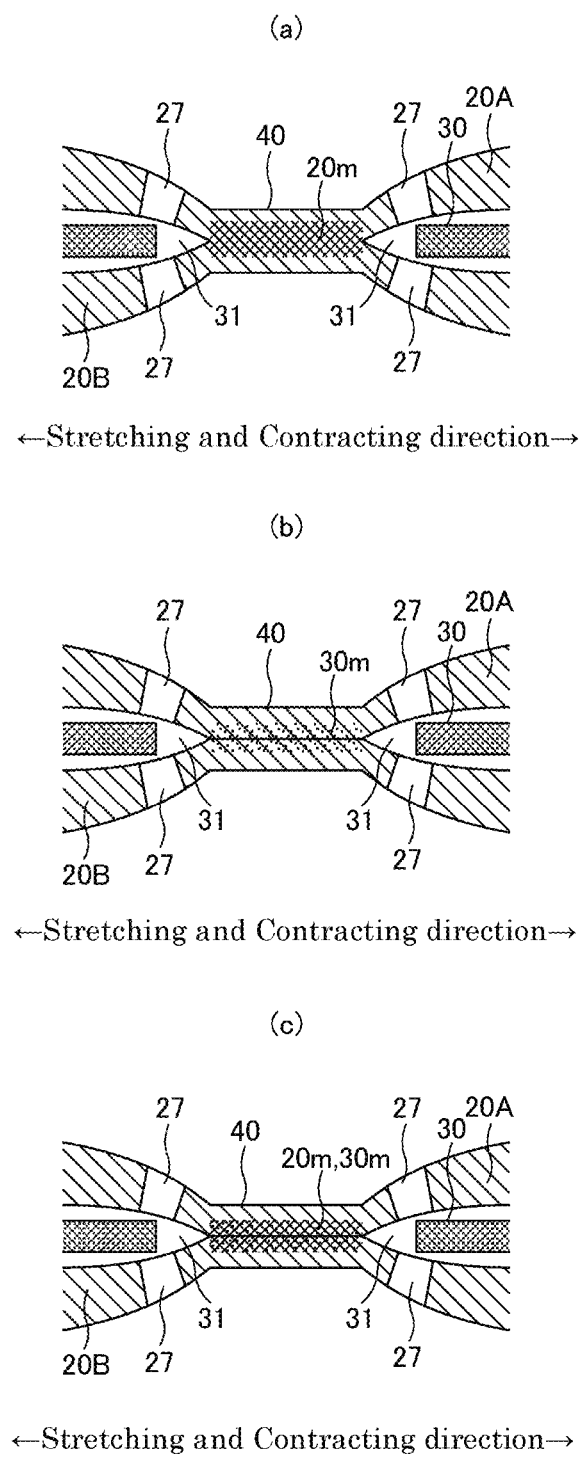
FIG. 32 is a cross-sectional view schematically illustrating a cross section of a main part of an outer body stretched to some extent.
Figure 34:
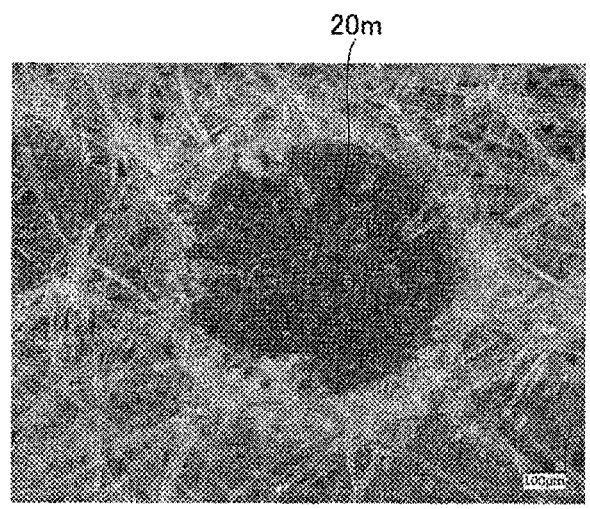
FIG. 34(a) is a plan photograph of a sheet bond portion formed in a first welding mode.
FIG. 34(b) is a plan photograph of the sheet bond portion formed in a third welding mode.
Figure 34:
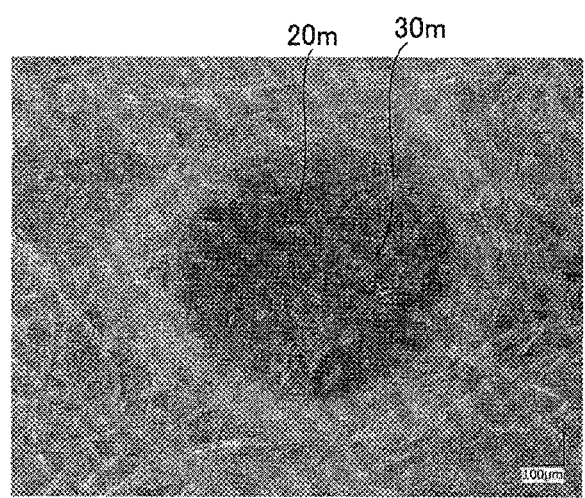

As a mode in which the sheet bond portions 40 are formed by material welding, it is possible to adopt any one of a first welding mode (see FIG. 32(a)) in which the first sheet layer 20A and the second sheet layer 20B are joined only by a melted and solidified material 20m corresponding to a most part or a part of at least one of the first sheet layer 20A and the second sheet layer 20B in the sheet bond portions 40; a second welding mode (see FIG. 32(b)) in which the first sheet layer 20A and the second sheet layer 20B are joined only by a melted and solidified material 30m corresponding to a whole, a most part, or a part of the elastic film 30 in the sheet bond portions 40; and a third welding mode (see FIG. 32(c)) obtained by combining these welding modes, and it is preferable to adopt the second and third welding modes. A particularly preferable mode is a mode in which the first sheet layer 20A and the second sheet layer 20B are joined by the melted and solidified material 20m corresponding to a part of the first sheet layer 20A and the second sheet layer 20B and the melted and solidified material 30m corresponding to a whole or a most part of the elastic film 30 in the sheet bond portions 40. The melted and solidified material 30m of the elastic film 30 appearing in white is seen in the melted and solidified material 20m with the fibers of the first sheet layer 20A or the second sheet layer 20B appearing in black in the third welding mode illustrated in FIG. 34(b), however, the melted and solidified material of the elastic film is not seen in the melted and solidified material 20m with the fibers of the first sheet layer 20A or the second sheet layer 20B in the first welding mode illustrated in FIG. 34(a) (a while part corresponds to scattered reflection of boundary of the melted and solidified material 20m with the fibers and the melted and solidified material 20m with the fibers).

In a case in which the first sheet layer 20A and the second sheet layer 20B are joined using the melted and solidified material 20m corresponding to a most part or a part of at least one of the first sheet layer 20A and the second sheet layer 20B as an adhesive as in a first adhesive mode or a third adhesive mode, it is preferable that a part of the first sheet layer 20A and the second sheet layer 20B is not melted in order not to harden the sheet bond portions 40. This situation in which "a part of the first sheet layer 20A and the second sheet layer 20B is not melted" includes, in a case that the first sheet layer 20A is composed of a nonwoven fabric and the second sheet layer 20B is composed of a nonwoven fabric, a mode in which for all fibers of the sheet bond portions 40, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

Peeling strength becomes high when the first sheet layer 20A and the second sheet layer 20B are bonded using the melted and solidified material 30m of the elastic film 30 as an adhesive as in the second welding mode and the third welding mode. In the second welding mode, under the condition that a melting point of at least one of the first sheet layer 20A and the second sheet layer 20B is higher than a melting point of the elastic film 30 and a heating temperature at the time of forming the sheet bond portions 40, the elastic film 30 may be interposed between the first sheet layer 20A and the second sheet layer 20B, apart corresponding to the sheet bond portions 40 may be pressed and heated, and only the elastic film 30 may be melted, thereby performing manufacture. Meanwhile, in the third welding mode, under the condition that a melting point of at least one of the first sheet layer 20A and the second sheet layer 20B is higher than the melting point of the elastic film 30, the elastic film 30 may be interposed between the first sheet layer 20A and the second sheet layer 20B, the part corresponding to the sheet bond portions 40 may be pressed and heated, and at least one of the first sheet layer 20A and the second sheet layer 20B and the elastic film 30 may be melted, thereby performing manufacture. From this point of view, the melting point of the elastic film 30 is preferably about 80 to 145° C., melting points of the first sheet layer 20A and the second sheet layer 20B are preferably about 85 to 190° C., particularly, 150 to 190° C., and a difference between the melting points of the first sheet layer 20A and the second sheet layer 20B and the melting point of the elastic film 30 is preferably about 60 to 90° C. In addition, the heating temperature is preferably set to 100 to 150° C.

Figure 33:
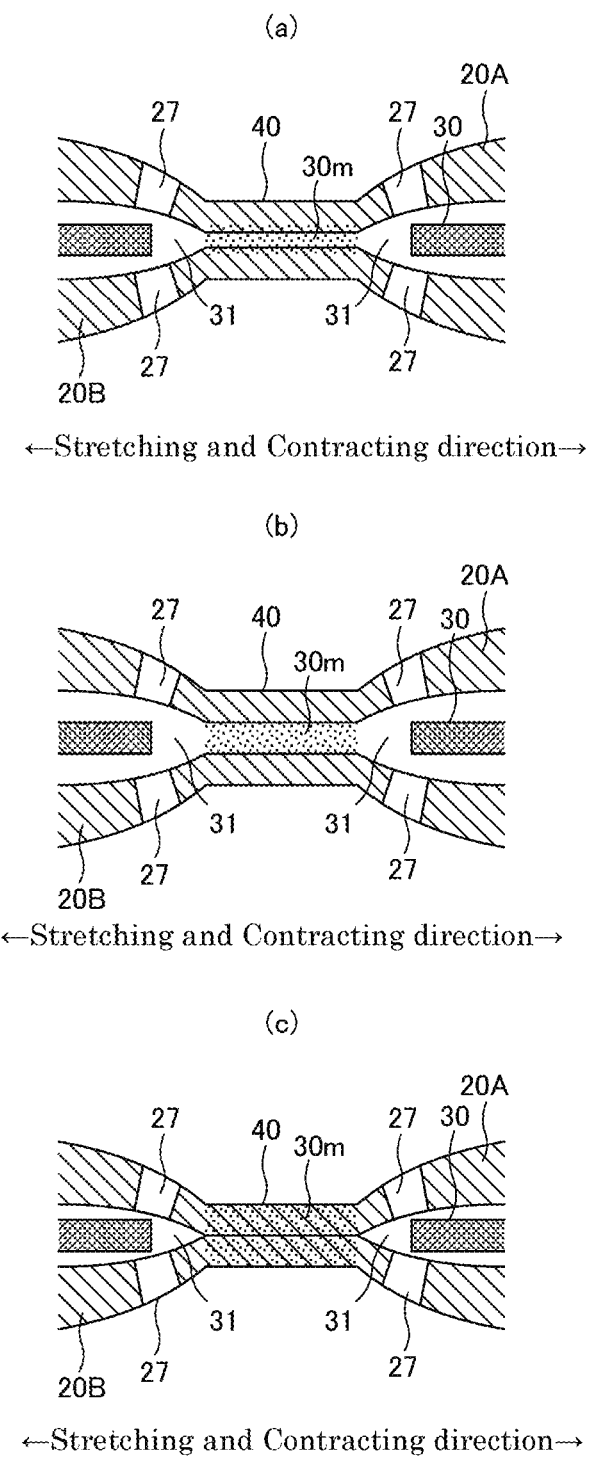
FIG. 33 is a cross-sectional view schematically illustrating a cross section of a main part of an outer body stretched to some extent.

In the second welding mode and the third welding mode, when the first sheet layer 20A and the second sheet layer 20B are nonwoven fabric, the melted and solidified material 30m of the elastic film 30 may infiltrate among fibers over the whole thickness direction of the first sheet layer 20A and the second sheet layer 20B of the sheet bond portions 40 as illustrated in FIG. 33(c). However, flexibility of the sheet bond portions 40 becomes high in a mode in which the melted and solidified material 30m infiltrates among fibers in the thickness direction halfway as illustrated in FIGS. 32(b), 32(c), and FIG. 33(a), or a mode in which the melted and solidified material 30m hardly infiltrate among the fibers of the first sheet layer 20A and the second sheet layer 20B as illustrated in FIG. 33(b).

Figure 35:
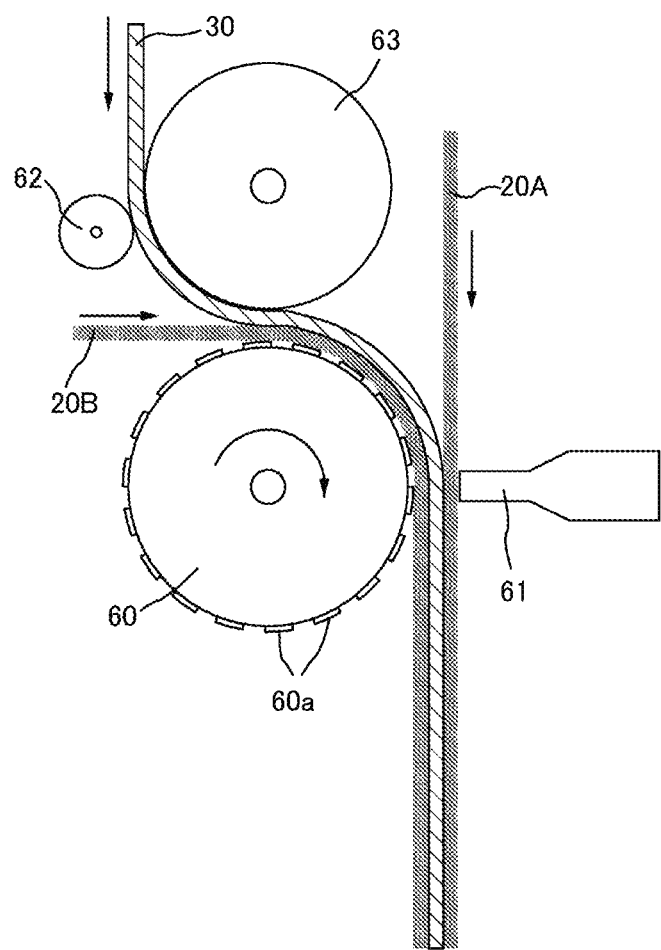
FIG. 35 is a schematic view of an ultrasonic sealing device.

FIG. 35 illustrates an example of an ultrasonic sealing device suitable for forming the second welding mode and the third welding mode. In this ultrasonic sealing device, to form bond portions 40, the first sheet layer 20A, the elastic film 30, and the second sheet layer 20B are fed between an ultrasonic horn 61 and an anvil roll 60 having a pattern of protrusions 60a of the sheet bond portions 40 on an external surface. In this instance, for example, when a feed speed transferring the elastic film 30 at an upstream side by a feed drive roll 63 and a nip roll 62 is controlled to be lower than a feed speed for transferring after the anvil roll 60 and the ultrasonic horn 61, the elastic film 30 is stretched to a predetermined stretch rate in an MD (machine direction, flow direction) on a path from a nip position by the feed drive roll 63 and the nip roll 62 to a sealing position by the anvil roll 60 and the ultrasonic horn 61. A stretch rate of the elastic film 30 may be determined by controlling a speed difference between the anvil roll 60 and the feed drive roll 63, and may be set to, for example, about 300% to 500%. Reference symbol 62 denotes the nip roll. The first sheet layer 20A, the elastic film 30, and the second sheet layer 20B fed between the anvil roll 60 and the ultrasonic horn 61 are, in a stacked state in this order, heated by ultrasonic vibration energy of the ultrasonic horn 61 while being pressed between the protrusions 60a and the ultrasonic horn 61. Further, the through holes 31 are formed in the elastic film 30 by melting only the elastic film 30 or melting the elastic film 30 and at least one of the first sheet layer 20A and the second sheet layer 20B. At the same time, the first sheet layer 20A and the second sheet layer 20B are joined via the through holes 31. Therefore, in this case, an area rate of the sheet bond portions 40 may be selected by selecting a size, a shape, a separation interval, an arrangement pattern in a roll length direction and a roll circumferential direction, etc. of the protrusions 60a of the anvil roll 60.

Although the reason for formation of the through holes 31 is not necessarily clear, it is considered that openings are formed by melting the elastic film 30 at corresponding sites to the protrusions 60a of the anvil roll 60 so as to be removed from the surroundings. In this instance, a portion between each pair of adjacent through holes 31 arranged in the stretching and contracting direction in the elastic film 30 is cut from portions at both sides in the stretching and contracting direction by the through holes 31 as illustrated in FIG. 23(a), FIG. 25(a), and FIG. 27(a), and support at both sides in a contraction direction is lost. Thus, in a range in which continuity in a direction orthogonal to the contraction direction can be maintained, the closer to the central side of a direction orthogonal to the stretching and contracting direction, the more elastic film 30 contracts to match with the central side in the stretching and contracting direction so that the through holes 31 are enlarged in the stretching and contracting direction. When the sheet bond portions 40 are formed in a pattern with a section being left in which the elastic film 30 linearly continues along the stretching and contracting direction, as in the stretchable region 80 explained after, the elastic film 30 contracts to the natural length state for example by cutting for obtaining individual products, an enlarged portion of each through hole 31 contracts in the stretching and contracting direction so that a gap cannot be formed between each through hole 31 and each sheet bond portion 40 as illustrated in FIG. 23(a) and FIG. 25(a). On the other hand, when the sheet bond portions 40 are formed in a pattern without such a section in which the elastic film 30 linearly continues along the stretching and contracting direction, as in the non-stretchable region 70 explained after, even if the elastic film 30 is cut for obtaining the individual products, contraction is not substantially performed, as illustrated in FIG. 27(a). Thus, a large gap is left between each through hole 31 and each sheet bond portion 40.

The first sheet layer 20A and the second sheet layer 20B may be composed of any sheet members, preferably nonwoven fabrics in view of air permeability and flexibility. The nonwoven fabric may be composed of any raw fiber. Examples of the raw fiber include synthetic fibers, such as olefin fibers, e.g., polyethylene fibers and polypropylene fibers, polyester fibers, and polyamide fibers; recycled fibers, such as rayon and cupra; natural fibers, such as cotton; and blend or conjugate fibers composed of two or more of these fibers. The nonwoven fabric may be prepared by any process. Examples of such a process include well-known processes, such as spun lacing, spun bonding, thermal bonding, melt blowing, needle punching, air-through processes, and point bonding. The nonwoven fabric preferably has a basis weight of approximately 12 to approximately 20 g/m$^2$. The first sheet layer 20A and the second sheet layer 20B may be composed of a pair of facing layers prepared by folding back a single sheet that is partially or entirely folded back. For example, as in the illustrated mode, in the waist end portion region 23, a component located outer side may be used as the second sheet layer 20B, the folded part 20C formed by folding back to the internal surface side at the waist opening edge thereof may be used as the first sheet layer 20A, and the elastic film 30 may be interposed therebetween, and in the rest part, a component located inner side may be used as the first sheet layer 20A, another component located outer side may be used as the second sheet layer 20B, and the elastic film 30 may be interposed therebetween. The component of the first sheet layer 20A and the component of the second sheet layer 20B may be separately provided across the whole part in the front-back direction, and the elastic film 30 may be interposed between the component of the first sheet layer 20A and the component of the second sheet layer 20B without folding back the component members.

The elastic film 30 may be composed of any thermoplastic resin film having elasticity. For example, it is possible to use a film in which a large number of holes or slits are formed for ventilation in addition to a nonporous film. In particular, it is preferable when the elastic film 30 has a tensile strength in the width direction (the stretching and contracting direction, the MD) of 8 to 25 N/35 mm, tensile strength in the front-back direction (the direction orthogonal to the stretching and contracting direction, the CD) of 5 to 20 N/35 mm, tensile elongation in the width direction of 450 to 1,050%, and tensile elongation in the front-back direction of 450 to 1,400%. The thickness of the elastic film 30 is not particularly restricted. However, the thickness is preferably in a range of about 20 to 40 µm.

Stretchable Region and Non-Stretchable Region

A region having the elastic film stretchable structure 20X in the outer body 20 includes the non-stretchable region 70 and the stretchable region 80 stretchable in the width direction provided at least at one side of the non-stretchable region 70 in the width direction. Arrangement of the stretchable region 80 and the non-stretchable region 70 may be appropriately determined. In the case of the outer body 20 of the underpants-type disposable diaper as in the present embodiment, a portion overlapping the absorber 13 is a region that may not be stretched or contracted. Thus, a part or a whole of the portion overlapping the absorber 13 (desirably including substantially the whole internal and external fixed region 10B) is preferably set to the non-stretchable region 70 as in the illustrated mode. The non-stretchable region 70 may be provided from a region overlapping the absorber 13 to a region not overlapping the absorber 13 positioned in the width direction or the front-back direction thereof, and the non-stretchable region 70 may be provided only in the region not overlapping the absorber 13.

Stretchable Region

The stretchable region 80 has a section 32 in which the elastic film 30 linearly continues along the width direction, contracts in the width direction due to a contraction force of the elastic film 30, and is stretchable in the width direction. More specifically, the whole elastic film stretchable structure 20X including both the stretchable region 80 and the non-stretchable region 70 is formed by joining the first sheet layer 20A and the second sheet layer 20B via the through holes 31 of the elastic film 30 to form a large number of sheet bond portions 40 at intervals in the width direction and the front-back direction orthogonal thereto (the direction orthogonal to the stretching and contracting direction) while the elastic film 30 is stretched in the width direction. Further, in the stretchable region 80, the through holes 31 may be disposed to have the section in which the elastic film 30 linearly continues along the width direction, thereby imparting elasticity.

In the stretchable region 80, as illustrated in FIG. 23(d) and FIG. 25(d), when the elastic film 30 is in the natural length state, the first sheet layer 20A and the second sheet layer 20B between the sheet bond portions 40 stretch in a direction away from each other, and thus a contraction wrinkle 25 extending in the front-back direction is formed. In a worn state in which the elastic film 30 is stretched to an extent in the width direction, as illustrated in FIG. 23(c) and FIG. 25(c), the contraction wrinkles 25 are still remain although the contraction wrinkles 25 are stretched. In addition, as in the illustrated mode, when the first sheet layer 20A is not and the second sheet layer 20B is not joined to the elastic film 30 in a portion other than at least between the first sheet layer 20A and the second sheet layer 20B in the sheet bond portions 40, as understood from FIG. 23(c) and FIG. 25(d) assuming the worn state and FIGS. 23(a) and 23(b) and FIGS. 25(a) and 25(b) assuming a spread state of the first sheet layer 20A and the second sheet layer 20B, a gap is formed between each through hole 31 of the elastic film 30 and the sheet bond portions 40 and in these states, and air permeability is imparted due to the gap even when a material of the elastic film 30 corresponds to a non-porous film or a sheet. In addition, when the elastic film 30 is in the natural length state illustrated in FIG. 23(d) and FIG. 25(d), the through holes 31 are narrowed by contraction of the elastic film 30, and a gap is hardly formed between each through hole 31 and the sheet bond portions 40. States of the contraction wrinkle 25 in the worn state and the natural length state are shown in reference sample photographs of FIG. 24 and FIG. 26 (sample in which a vent hole 27 is not formed).

An elongation at an elastic limit of the stretchable region 80 in the width direction is desirably set to 200% or more (preferably 265% to 295%). The elongation at the elastic limit of the stretchable region 80 is substantially determined by the stretch rate of the elastic film 30 in the manufacturing. However, the elongation at the elastic limit decreases due to a factor that inhibits contraction in the width direction based thereon. A main inhibition factor corresponds to a ratio of the length 40x of the sheet bond portions 40 to a unit length in the width direction. As this ratio increases, the elongation at the elastic limit decreases. In general, since the length 40x of each of the sheet bond portions 40 correlates with the area rate of the sheet bond portions 40, the elongation at the elastic limit of the stretchable region 80 may be adjusted by the area rate of the sheet bond portions 40.

Stretching stress of the stretchable region 80 may be adjusted mainly by a sum of widths 32w of sections 32 in each of which the elastic film 30 linearly continues along the width direction. The width 32w of the section 32 in which the elastic film 30 linearly continues along the width direction is equal to an interval 31d of the through holes 31 coming into contact with both side edges of the continuing portion 32 in the front-back direction. The interval 31d of the through holes 31 is equal to an interval 40d of the sheet bond portions 40 coming into contact with the both side edges of the continuing sections in the front-back direction when the length 31y of the through hole 31 in the front-back direction is equal to the length 40y of the sheet bond portion 40 in the front-back direction (when a scheme of simultaneously forming the through holes 31 and the sheet bond portions 40 described above is adopted). Therefore, in this case, the stretching stress of the stretchable region 80 may be adjusted by a ratio of the length 40y of each of the sheet bond portions 40 to a unit length in the front-back direction. In general, since the length 40y of each of the sheet bond portions 40 correlates with the area rate of the sheet bond portions 40, the stretching stress of the stretchable region 80 may be adjusted by the area rate of the sheet bond portions 40. Stretching stress in stretching to an elastic limit of 50% may be estimated as the stretching stress of the stretchable region 80.

The area rate of the sheet bond portions 40 and the area of each of the sheet bond portions 40 in the stretchable region 80 may be appropriately determined. However, in general, the area rate and the areas are preferably set within the following ranges.

Area of each of sheet bond portions 40: 0.14 to 3.5 mm$^2$ (particularly 0.14 to 1.0 mm$^2$)

Area rate of sheet bond portions 40: 1.8 to 19.1% (particularly 1.8 to 10.6%)

Figure 31:
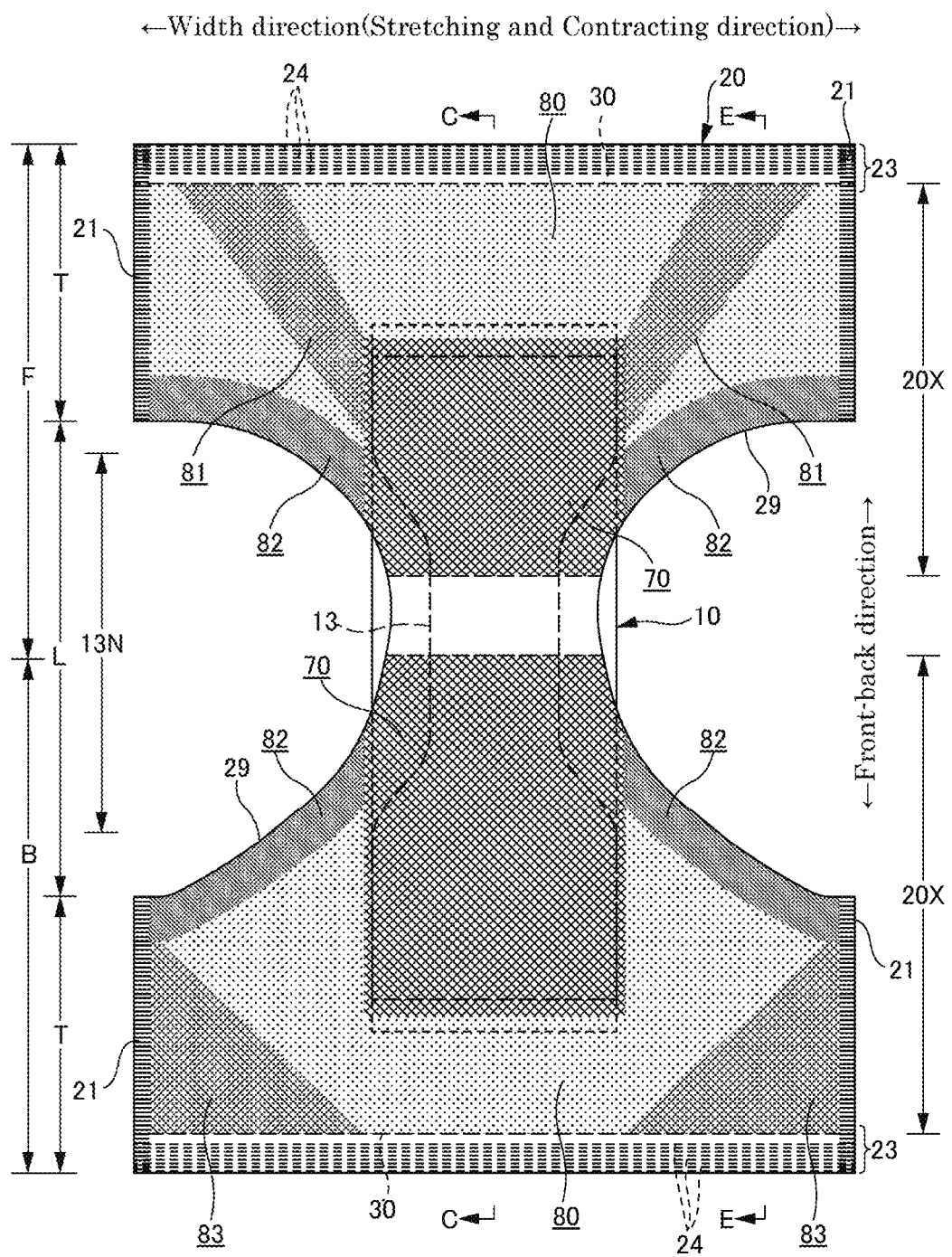
FIG. 31 is a plan view (external surface side) of the underpants-type disposable diaper in the spread state.

As described above, the elongation at the elastic limit and the stretching stress of the stretchable region 80 may be adjusted by the area of each of the sheet bond portions 40. Thus, as illustrated in FIG. 31, it is possible to provide a plurality of regions having different area rates of the sheet bond portions 40 in the stretchable region 80, and to change fitness according to a part. In a mode illustrated in FIG. 31, in the front body F, regions 81 each extending in an oblique direction along a base of the leg and edge portion regions 82 of the leg openings have respectively, when compared to other regions, higher area rates of the sheet bond portions 40, and thus have smaller stretching stresses, resulting in abilities to stretch flexibly. In addition, in the back body B, ilium facing regions 83 and the edge portion regions 82 of the leg openings have, when compared to other regions, high area rates of the sheet bond portions 40, and thus have small stretching stresses, resulting in abilities to stretch flexibly.

Non-Stretchable Region

Figure 27:
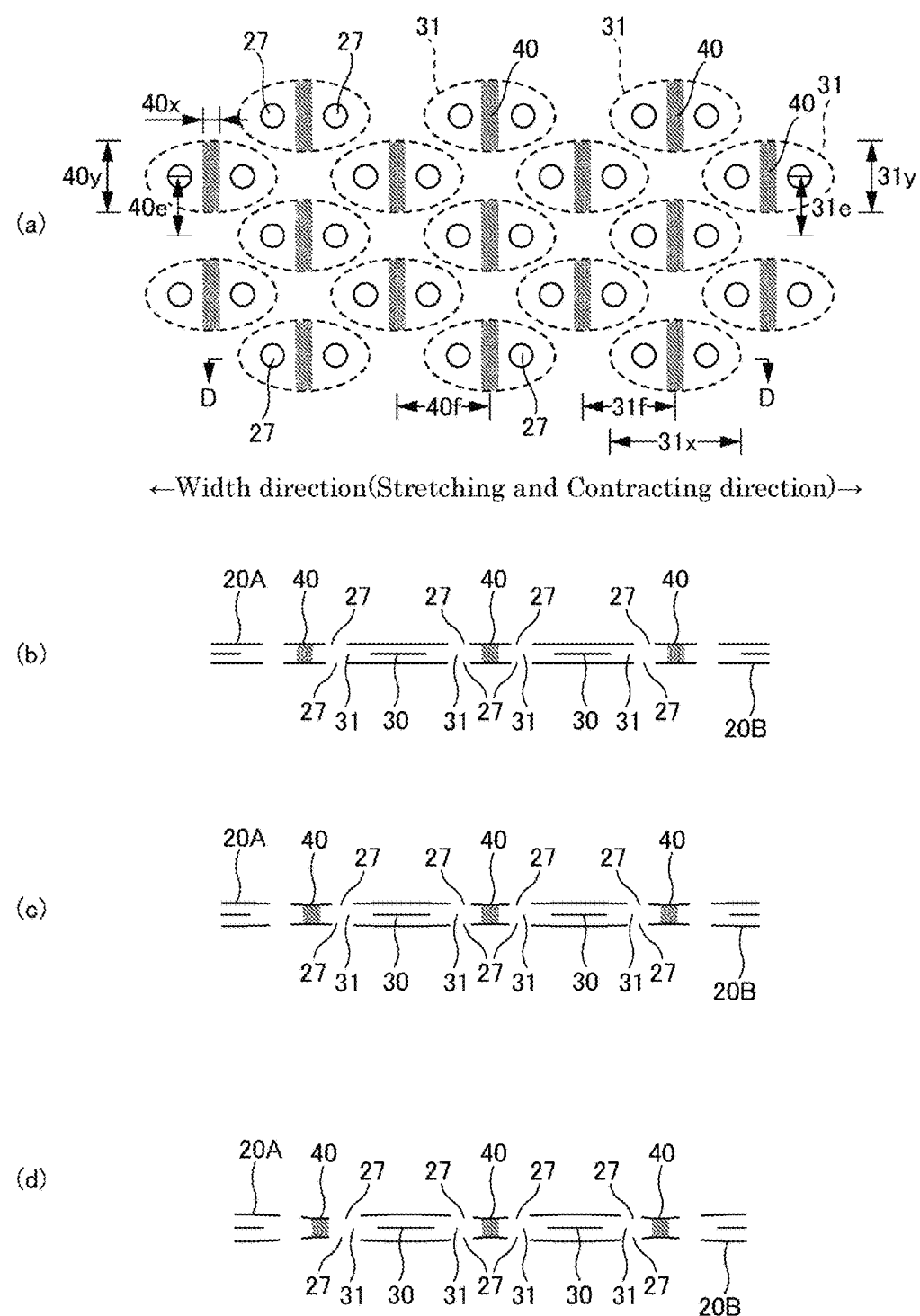
FIG. 27(a) is a plan view of a main part of a non-stretchable region.
FIG. 27(b) is a D-D cross-sectional view of FIG. 27(a)
FIG. 27(c) is a cross-sectional view in the worn state.
FIG. 27(d) is a cross-sectional view in the natural length state.

Meanwhile, the non-stretchable region 70 is configured, even through the elastic film 30 continues in the width direction, so as not to have a section in which the elastic film 30 linearly continues along the width direction, due to the presence of the through holes 31. Therefore, even though the elastic film stretchable structure 20X is configured as a whole to include both the stretchable region 80 and the non-stretchable region 70 by joining the first sheet layer 20A and the second sheet layer 20B via the through holes 31 of the elastic film 30 to form the large number of sheet bond portions 40 at intervals in the width direction and the front-back direction orthogonal thereto while the elastic film 30 is stretched in the width direction, in the non-stretchable region 70, the elastic film 30 does not linearly continue along the width direction as illustrated in FIG. 27. Thus, the contraction force of the elastic film 30 hardly acts on the first sheet layer 20A and the second sheet layer 20B, elasticity is almost lost, and the elongation at the elastic limit approaches 100%. Further, in the non-stretchable region 70, the first sheet layer 20A and the second sheet layer 20B are joined by the large number of sheet bond portions 40 arranged at intervals, and the sheet bond portions 40 are discontinuous. Thus, a decrease inflexibility is prevented. In other words, it is possible to form the stretchable region 80 and the non-stretchable region 70 depending on the presence or absence of a section in which the elastic film 30 does not linearly continue along the width direction. In addition, continuity of the elastic film 30 remains in the non-stretchable region 70. As understood from a reference sample photograph (sample in which a vent hole 27 is not formed) illustrated in FIG. 28, since an independent cut piece of the elastic film 30 is not left, and no wrinkle is formed, appearance is extremely excellent, and air permeability in the thickness direction by the through holes 31 is ensured. In the non-stretchable region 70, the elongation at elastic limit in the width direction is preferably 120% or less (preferably 110% or less, more preferably 100%).

Figure 28:
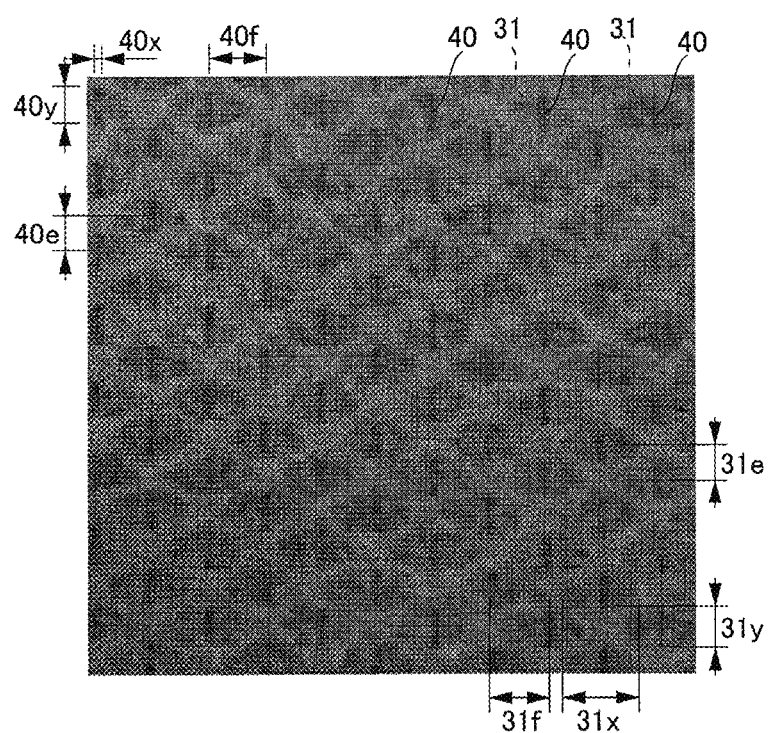
FIG. 28 is a photograph of the non-stretchable region of the reference sample.

An arrangement pattern of the through holes 31 in the elastic film 30 in the non-stretchable region 70 may be appropriately determined. However, when staggered arrangement is adopted as illustrated in FIG. 27 to FIG. 30, and a pattern in which a center interval 31$e$ of the through holes 31 in the front-back direction is shorter than the length 31$y$ of each of the through holes 31 in the front-back direction is adopted, linear continuity in the width direction may be almost completely eliminated while maintaining continuity of the elastic film 30, and appearance is preferable as illustrated in FIG. 28. In this case, it is more preferable that a center interval 31$f$ of the through holes 31 in the width direction is shorter than a length 31$x$ of each of the through holes 31 in the width direction.

In general, especially when stretching stress is in a range of 2.5 to 4.5 N/35 mm in stretching the elastic film 30 four times in the width direction, in a state in which the non-stretchable region 70 is stretched to the elastic limit in the width direction, the center interval 31$e$ of the through holes 31 in the front-back direction is preferably in a range of 0.3 to 2.7 mm, and the length 31$y$ of each of the through holes 31 in the front-back direction is preferably in a range of 0.5 to 3.0 mm, particularly in a range of 0.7 to 1.1 mm. In addition, the center interval 31$f$ of the through holes 31 in the width direction is preferably 3.5 to 5.5 times, particularly 3.5 to 4.5 times the length 31$y$ of the through holes 31 in the front-back direction, and the length 31$x$ of each of the through holes 31 in the width direction is preferably 1.0 to 4.0 times, particularly 1.5 to 3.0 times the center interval 31$f$ of the through holes 31 in the width direction. In a state in which the non-stretchable region 70 is stretched to an elastic limit in the width direction (in other words, in a state in which the first sheet layer 20A and the second sheet layer 20B are completely spread), the center interval 31$f$ of the through holes 31 in the width direction is equal to a center interval 40$f$ of the sheet bond portions 40 in the width direction, the center interval 31$e$ of the through holes 31 in the front-back direction is equal to a center interval 40$e$ of the sheet bond portions 40 in the front-back direction, and the length 31$y$ of each of the through holes 31 in the front-back direction is equal to the length 40$y$ of each of the sheet bond portions 40 in the front-back direction.

In a case in which the first sheet layer 20A is not and the second sheet layer 20B is not joined to the elastic film 30 in a portion other than between the first sheet layer 20A and the second sheet layer 20B in the sheet bond portions 40 in the non-stretchable region 70, and gaps, which are generated by the peripheral edge of each of the through holes 31 of the elastic film 30 and each of the sheet bond portions 40 separated from each other, are included at both sides of each of the sheet bond portions 40 in the width direction in the natural length state, air permeability is imparted at all times due to the gaps even if the material of the elastic film 30 is a non-porous film or a non-porous sheet, and thus the case is preferable. In the case of adopting a scheme of simultaneously forming the through holes 31 and the sheet bond portions 40 described above, this state is automatically obtained irrespective of a shape of the sheet bond portions 40.

The shape of each of the sheet bond portions 40 and the through holes 31 in the natural length state is not particularly restricted. However, it is desirable to have a small area from a viewpoint of flexibility, and it is desirable to have a shape which is long in the front-back direction to eliminate linear continuity in the width direction of the elastic film 30. Thus, it is preferable to adopt an ellipse which is long in the front-back direction, a rectangle (see FIG. 27), the rhombus (see FIG. 29($b$), the convex lens shape (see FIG. 29($a$)), and the concave lens shape (see FIG. 30($a$)). However, when corners are acute as in the rhombus, the elastic film 30 is easily fractured. In contrast, the convex lens shape is preferable since welding of the sheet bond portions 40 is stabilized, and the concave lens shape is preferable in that an area may be further reduced.

It is possible to appropriately determine the area rate of the sheet bond portions 40 and the area of each of the sheet bond portions 40 in the non-stretchable region. However, in general, ranges below are preferable since the area of each of the sheet bond portions 40 is small, the area rate of the sheet bond portions 40 is low, and thus the non-stretchable region 70 is not hardened.

Area of each of sheet bond portions 40: 0.10 to 0.75 mm$^2$ (particularly 0.10 to 0.35 mm$^2$)

Area rate of sheet bond portions 40: 4 to 13% (particularly 5 to 10%)

As described above, the elongation at the elastic limit of the non-stretchable region 70 may be changed by the arrangement pattern of the through holes 31, dimensions of each of the through holes 31, and the center interval of the through holes 31. Therefore, although not illustrated, it is possible to make the elongation at the elastic limit different between a plurality of positions in the stretchable region 80 or a plurality of non-stretchable regions 70. For example, in a preferable mode, the elongation at the elastic limit in the non-stretchable region 70 of the front body F is set to be larger than the elongation at the elastic limit in the non-stretchable region 70 of the back body B.

Even though the non-stretchable region 70 has a section that linearly continues along the width direction similarly to the stretchable region, since the area rate of the sheet bond portions in the non-stretchable region 70 is higher than that in the stretchable region, the elongation at the elastic limit is remarkably low in the non-stretchable region 70. Specifically, it is possible to adopt another mode for eliminating elasticity such as a mode in which the elongation at the elastic limit is 130% or less, a mode in which cutting is performed in the width direction at one position or a plurality of positions as in a conventional stretchable structure using a rubber thread, etc.

Vent Hole

Characteristically, as illustrated in FIG. 7, FIG. 9, FIG. 17 and FIG. 18, in the first sheet layer 20A and the second sheet layer 20B of the stretchable region 80, the vent hole 27 is formed by piercing to penetrate the sheet layer in a thickness direction in a portion other than the sheet bond portions 40. As a result, it is possible to improve air permeability in the thickness direction, without impairing a texture, due to the presence of the through holes 31 of the elastic film 30 and the vent hole 27 in at least one of the first sheet layer 20A and the second sheet layer 20B. The vent hole 27 may be formed in only either one of the first sheet layer 20A and the second sheet layer 20B. In addition, as illustrated in FIG. 11, FIG. 13, and FIG. 14, the vent hole 27 may be formed in the non-stretchable region 70 and the vent hole may be or may not be formed in the stretchable region 80.

The vent hole 27 may be formed by a punching process or a needle prick process. The vent hole 27 may be processed before the sheet bond portions 40 are formed, that is, in a single state of the first sheet layer 20A and the second sheet layer 20B, or may be processed in a state in which the first sheet layer 20A, the elastic film 30, and the second sheet layer 20B are stacked after the sheet bond portions 40 are formed. However, since the elastic film 30 is present after the sheet bond portions 40 are formed, it is desirable that the vent hole 27 is formed by piercing at a position overlapping the through holes 31 of the elastic film 30 as described below. The elastic film 30 may be pierced together with the first sheet layer 20A, the elastic film 30, and the second sheet layer 20B while they are stacked. However, in this case, stretching stress due to the piercing, an influence on the elongation at the elastic limit, cutting of the elastic film 30, etc. need to be taken into consideration.

A formation position of the vent hole 27 is not particularly restricted. However, the through holes 31 formed in the elastic film 30 are enlarged to both sides of the sheet bond portions 40 in the width direction when the stretchable region 80 is stretched at the time of use, and the through holes 31 are enlarged to both sides of the sheet bond portions 40 in the width direction even in the natural length state in the non-stretchable region 70. Thus, as in the illustrated mode, in any one of the stretchable region 80 and the non-stretchable region 70, at least one vent hole 27 is formed on each side of each of the sheet bond portions 40 in the stretching and contracting direction in terms of improving air permeability.

Figure 24:
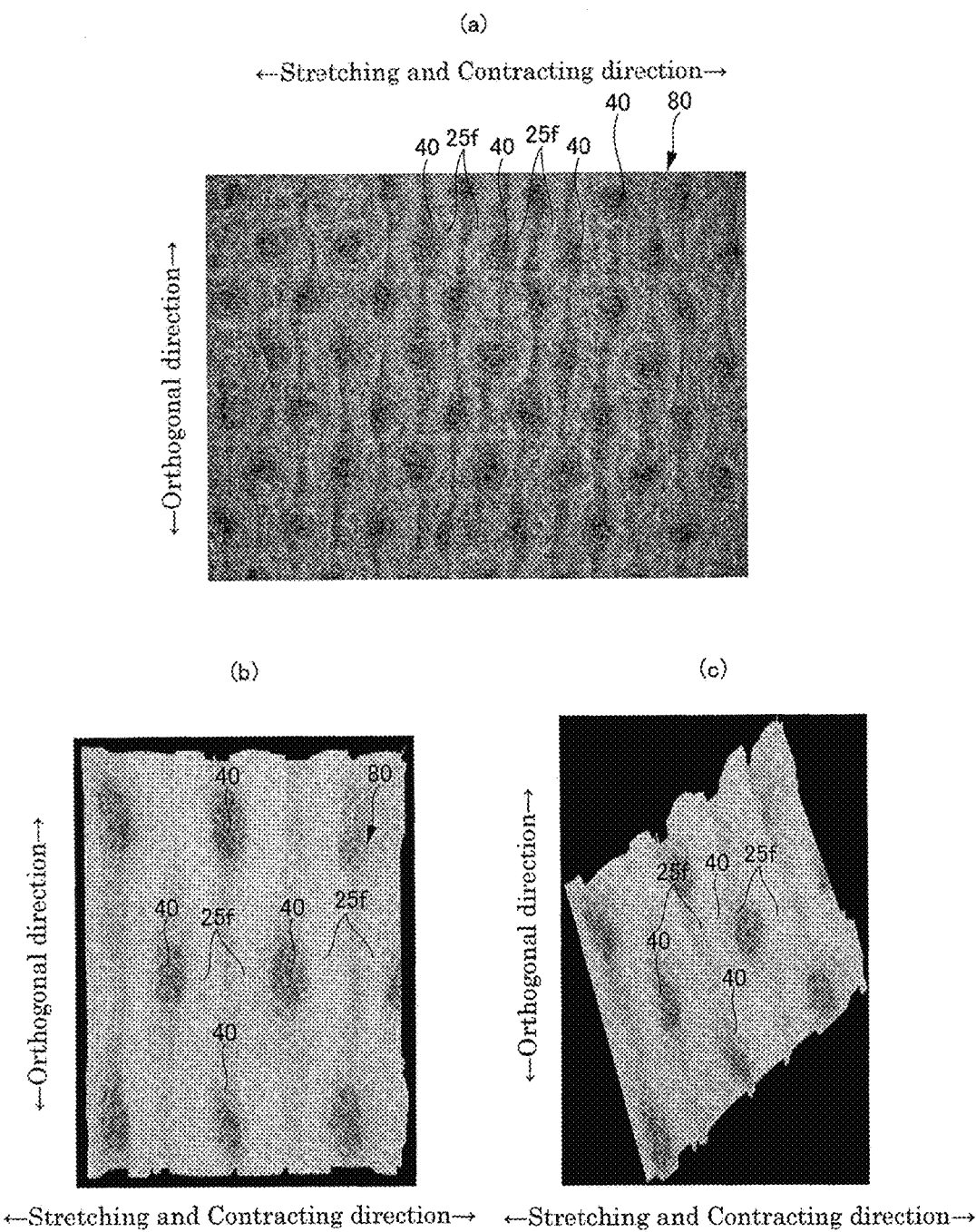
FIG. 24(a) is a microscope photograph from a plane direction.
FIG. 24(b) is a high-magnification microscope photograph from the plane direction.
FIG. 24(c) is a high-magnification microscope photograph from an oblique direction in a stretchable region of a reference sample.
Figure 25:
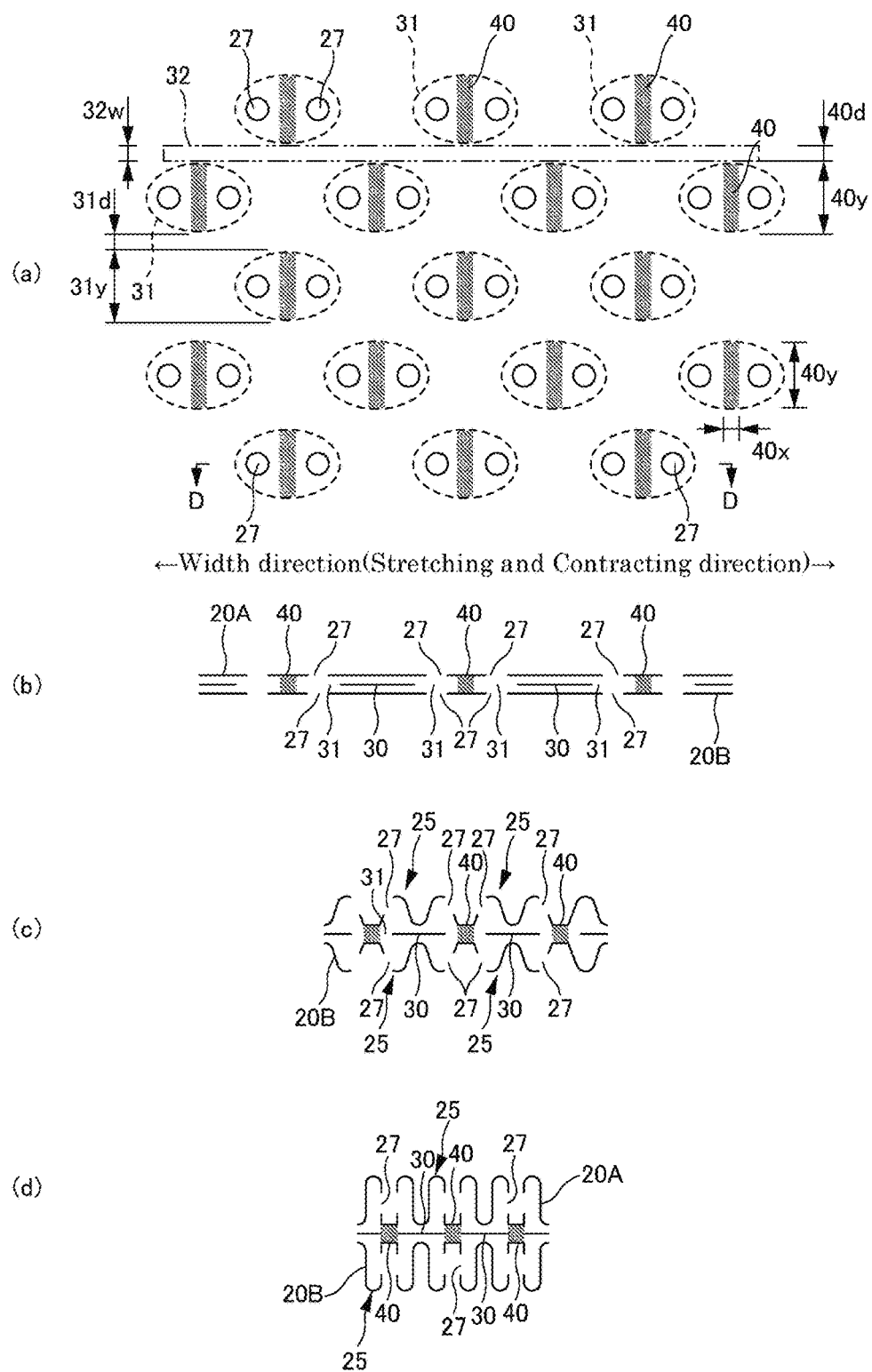
FIG. 25(a) is a plan view of a main part of a stretchable region.
FIG. 25(b) is a D-D cross-sectional view of FIG. 25(a)
FIG. 25(c) is a cross-sectional view in a worn state.
FIG. 25(d) is a cross-sectional view in a natural length state.
Figure 26:
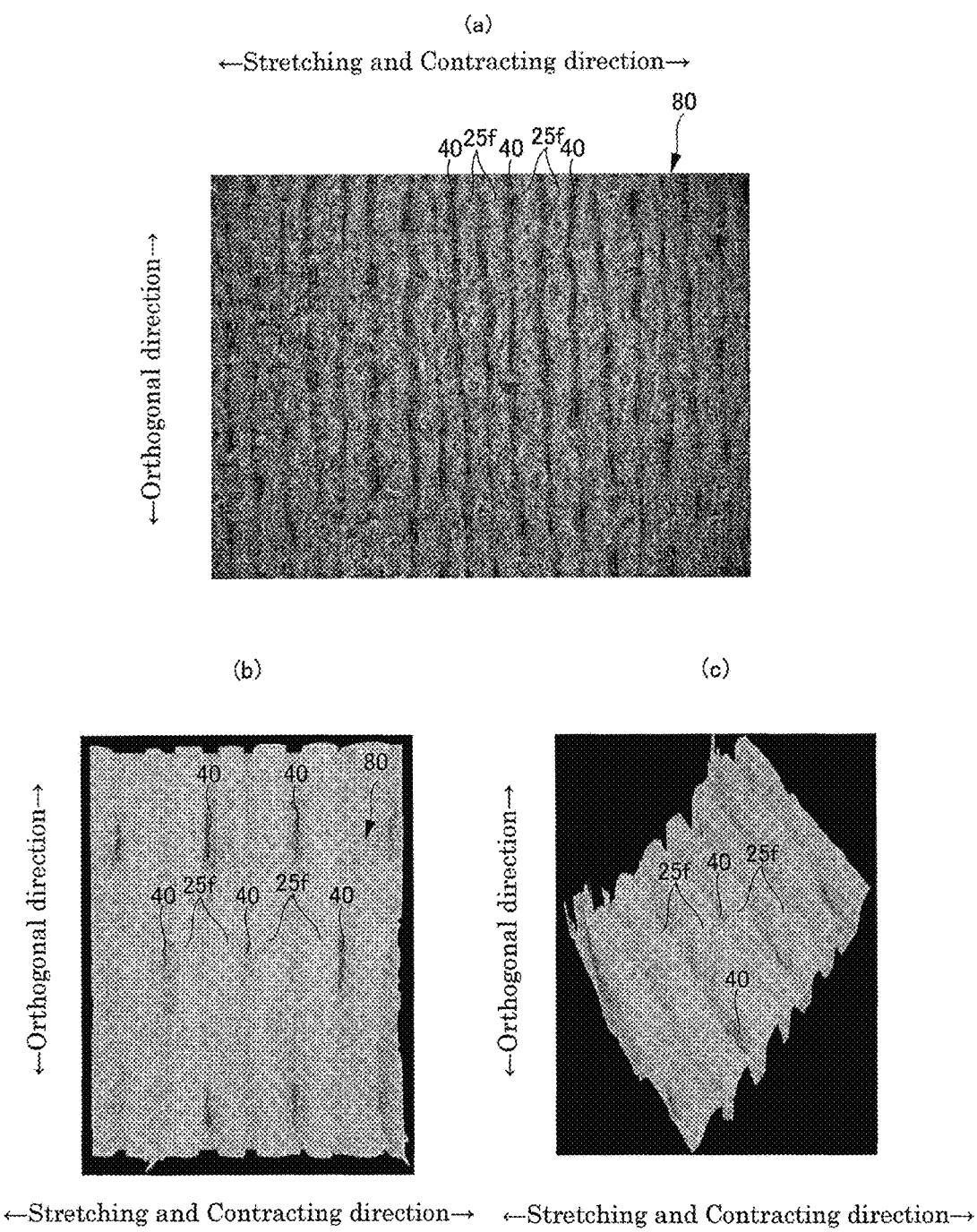
FIG. 26(a) is a microscope photograph from a plane direction.
FIG. 26(b) is a high-magnification microscope photograph from the plane direction.
FIG. 26(c) is a high-magnification microscope photograph from an oblique direction in the stretchable region of a reference sample.

In particular, in a preferable mode, in a state in which the stretchable region 80 is stretched, that is, in a state in which an elastic limit is included excluding the natural length state, the vent hole 27 is disposed with respect to the through holes 31 such that a part or a whole of the vent hole 27 overlaps each of the through holes 31, as illustrated in FIG. 23 and FIG. 24. When the stretchable region 80 is stretched at the time of use, since the through hole 31 formed in the elastic film 30 is enlarged in the width direction, in a case in which the vent hole 27 is disposed with respect to the through holes 31 such that a part or a whole of the vent hole 27 overlaps each of the enlarged through holes 31, air permeability via the through hole 31 is particularly improved. FIG. 23(*a*) and FIG. 25(*a*) illustrate overlapping states at the elastic limit, and overlap begins in a process of stretching to the elastic limit. Therefore, it is preferable to adopt a configuration in which the vent hole 27 of the first sheet layer 20A and the second sheet layer 20B overlaps each of the through holes 31 of the elastic film 30 in a stretch rate range of 150 to 200% on the assumption of the worn state.

Figure 29:
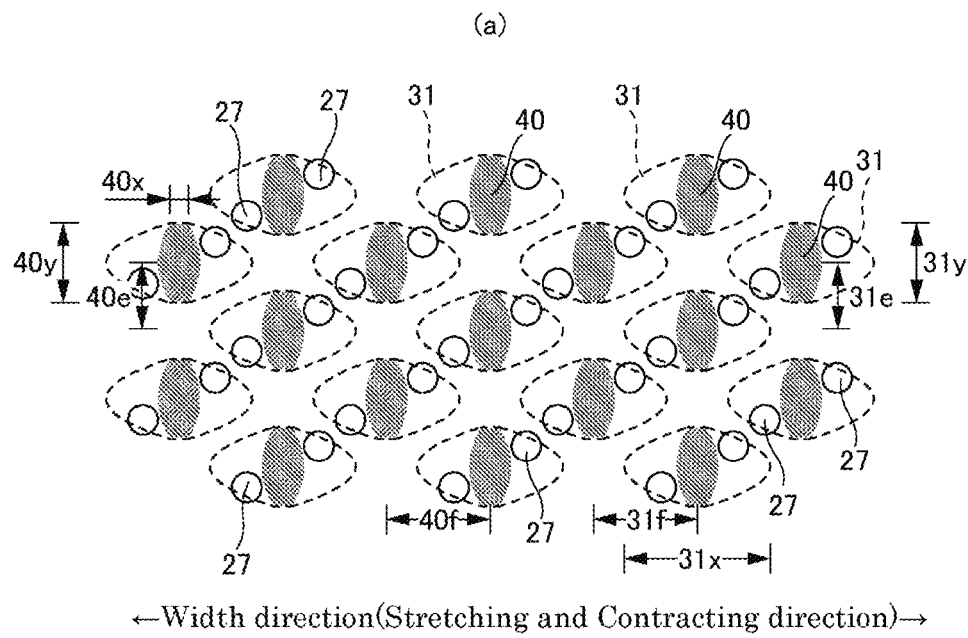
FIG. 29 is a plan view of a main part of the non-stretchable region.
Figure 29:
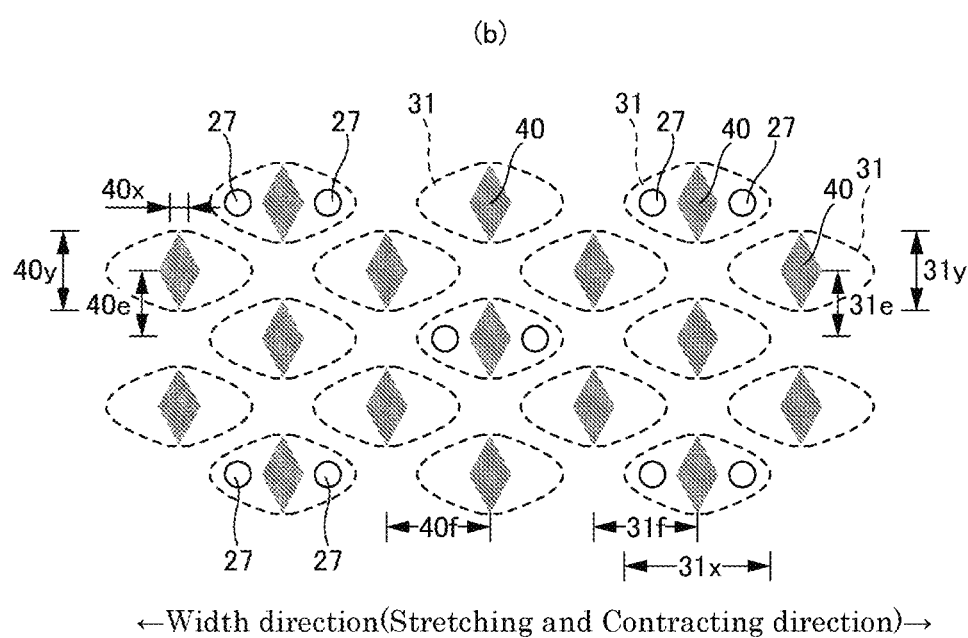
Figure 30:
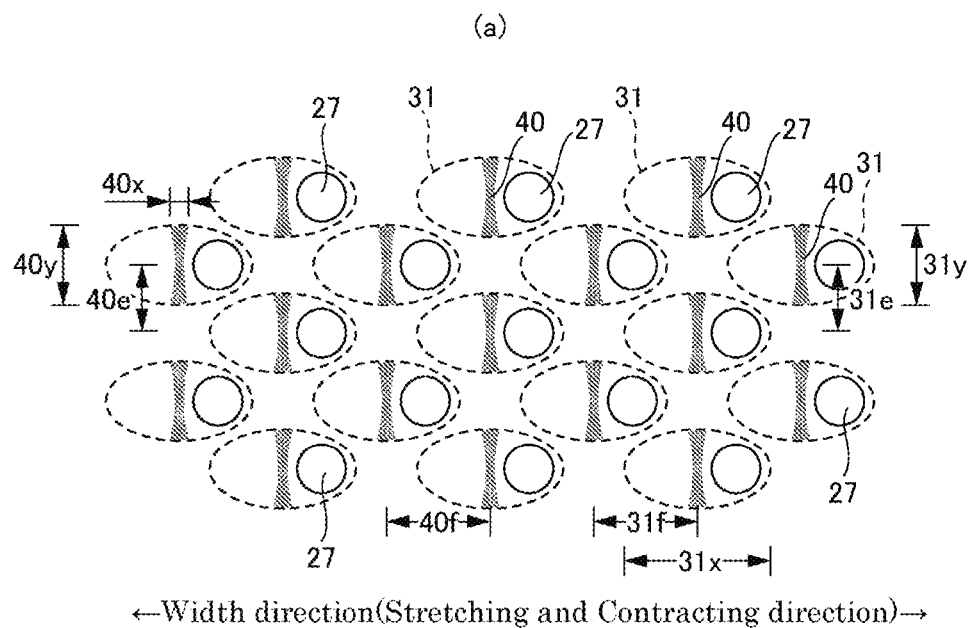
FIG. 30 is a plan view of a main part of the non-stretchable region.
Figure 30:
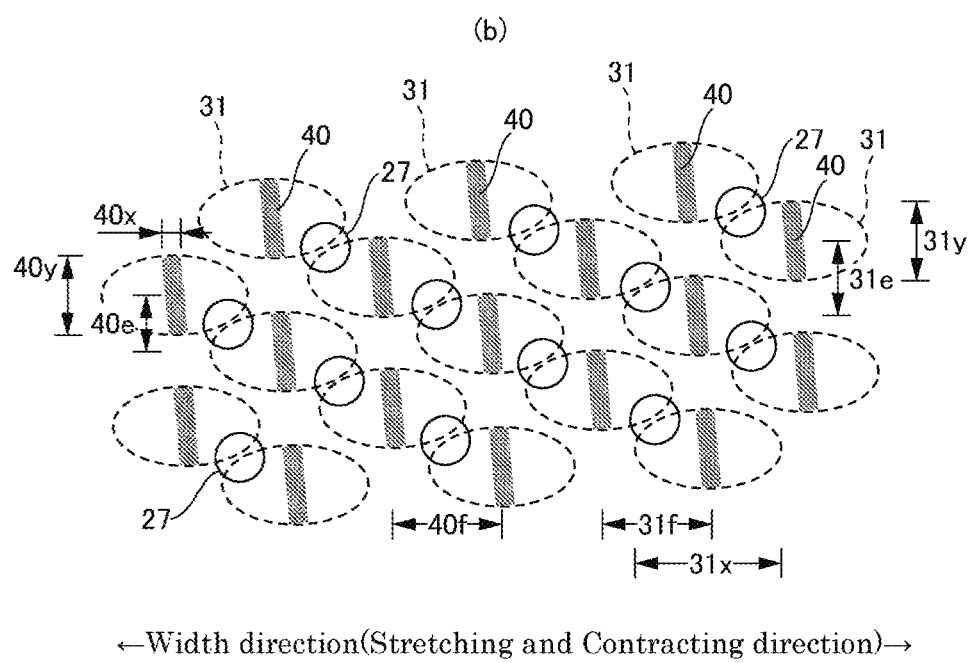

For a similar reason, when the vent hole 27 is formed in the non-stretchable region 70 as illustrated in FIG. 27, FIG. 29, and FIG. 30, it is preferable to dispose the vent hole 27 with respect to the through hole 31 such that a part or a whole of the vent hole 27 overlaps the through hole 31 in the natural length state of the non-stretchable region. In a preferable mode, one vent hole is preferable disposed to straddle and overlap a plurality of through holes as illustrated in FIG. 30(*b*). The mode illustrated in FIG. 30(*b*) relates to the non-stretchable region 70. However, the same mode may be adopted in the stretchable region 80.

In the stretchable region 80 and the non-stretchable region 70, when a part or a whole of the vent hole 27 is disposed to overlap the through hole 31 during use, there is a concern that a skin exposure may increase due to improvement of permeability, or leak prevention may deteriorate even though air permeability is improved. Therefore, to solve such problem, although not illustrated, it is preferable, independently of a state in which the stretchable region 80 is stretched or not, none of the vent hole 27 overlaps the through holes 31.

The first sheet layer 20A and the second sheet layer 20B are layers that cover the elastic film 30, and are members that require durability such as rub resistance. In addition, when the first sheet layer 20A is composed of a nonwoven fabric and the second sheet layer 20B is composed of a nonwoven fabric, the number of vent holes 27 may not be excessively increased since the material has air permeability. On the other hand, a considerable number of through holes 31 of the elastic film 30 are used to ensure air permeability and join uniformly the first sheet layer 20A and the second sheet layer 20B as one unit. Therefore, in a preferable mode, the number of vent holes 27 is set to be smaller than the number of through holes 31. The modes illustrated in FIG. 29(b) and FIG. 30(b) relate to the non-stretchable region 70. However, the same modes may be adopted in the stretchable region 80.

A shape of the vent hole 27 is not particularly restricted, and may be set to an arbitrary shape such as a perfect circle (illustrated mode), an ellipse, a polygon such as a triangle, a rectangle, a rhombus, etc., a star shape, a cloud shape, etc. A size of the vent hole 27 is not particularly restricted. However, when the size is excessively small or an excessively small number of vent holes 27 are present, an effect of improving air permeability becomes poor. When the size is excessively large or an excessively large number of vent holes 27 are present, a decrease in strength or deterioration in appearance of the first sheet layer 20A and the second sheet layer 20B is caused. Thus, in general, an area of the vent hole 27 is preferably set to about 0.34 to 3.5 mm$^2$, and an area rate of the vent holes 27 is preferably set to about 4.4 to 19.1%.

A planar array of the vent holes 27 may be appropriately determined. However, as illustrated in FIG. 23, FIG. 25, FIG. 27, FIG. 29, and FIG. 30, it is preferable to adopt a planar array in which the vent holes 27 are regularly repeated. Similarly to the arrangement mode of the sheet bond portions 40 illustrated in FIG. 19, in addition to the planar array in which the vent holes 27 are regularly repeated such as an oblique lattice shape or a hexagonal lattice shape (these shapes are also referred to as a staggered shape), a square lattice shape, a rectangular lattice shape, a parallel body lattice shape (a mode in which two groups are provided such that a large number of parallel oblique row groups intersect each other as illustrated in the figure), etc. (including a mode in which these shapes are inclined at an angle less than 90 degrees with respect to the width direction), it is possible to adopt a planar array in which a group of the vent holes 27 (arrangement of a group unit may be regular or irregular, and a pattern, a letter shape, etc. may be used) is regularly repeated.

Others

A part or a whole of the mode for solving the first problem may be applied to the mode for solving the second problem. On the contrary, a part or a whole of the mode for solving the second problem may be applied to the mode for solving the first problem.

Description of Terms in Specification

The terms used in the specification have the following meanings unless otherwise stated.

The "front body" and the "back body" refer to front and back portions using the center of the underpants-type disposable diaper in the front-back direction as a boundary. In addition, the crotch portion refers to a front-back direction range including the center of the underpants-type disposable diaper in the front-back direction, and refers to a front-back direction range of a portion having a narrower part when the absorber has the narrower part.

The "elongation at the elastic limit" refers to an elongation at an elastic limit in the stretching and contracting direction (in other words, a state in which the first sheet layer and the second sheet layer are completely spread), and expresses a length at the time of the elastic limit as a percentage when the natural length is set to 100%.

The "area rate" refers to a rate of a target portion to a unit area, and expresses the rate as a percentage by dividing a total area of the target portion (for example, the sheet bond portions 40, the openings of the through holes 31, and the vent hole) in a target region (for example, the stretchable region 80 and the non-stretchable region 70) by an area of the target region. Particularly, an area rate in a region having a stretchable structure (for example, an area rate of sheet bond portions) refers to an area rate in a state of being stretched in the stretching and contracting direction to the elastic limit. In a mode in which a plurality of target portions is provided at intervals, it is desirable to obtain the area rate by setting the target region to a size at which ten or more target portions are included.

The area of the opening of each of the through holes refers to a value obtained when the elastic film stretchable structure is in a natural length state, and refers to a minimum value in a case in which the area of the opening of each of the through holes is not uniform in the thickness direction such as a case in which the area is different between the front and the back of the elastic film.

The MD refers to a machine direction, that is, a line flow direction, and the CD refers to a horizontal direction orthogonal to the MD.

The "stretch rate" represents a value relative to the natural-length (100%)

The "Basis weight" is determined as follows: After the sample or test piece is preliminarily dried, it is allowed to stand in a testing chamber or machine under the standard condition (temperature: 20±5° C., relative humidity: 65% or less) until the constant mass. The preliminary drying represents that the sample or test piece reaches constant mass in an environment within a relative humidity of 10 to 25% and at a temperature not exceeding 50° C. The fiber of an official regain of 0.0% does not need preliminary drying. A cut sample with a size of 200 mm by 250 mm (±2 mm) is prepared from the test piece after the constant mass with a cutting template (200 mm by 250 mm, ±2 mm). The sample is weighed and the weight is multiplied by 20 into the weight per square meter. The resulting value is defined as basis weight.

The "thickness" of the absorber is measured using a thickness measurement apparatus of OZAKIMGF Co., Ltd. (PEACOCK, Dial Thickness Gauge Large Type, Model J-B (Range 0 to 35 mm) or Model K-4 (Range 0 to 50 mm)) by horizontally disposing a sample and the thickness measurement apparatus.

A "thickness" other than the above-described thickness is automatically determined with an automatic thickness gauge (KES-G5 handy compression measurement program) under the conditions of a load of 10 gf/cm$^2$ and a pressurization area of 2 cm$^2$.

The "tensile strength" and the "tensile elongation at break" are measured at an initial chuck interval of 50 mm and a speed of testing of 300 mm/min with a tensile tester (for example, AUTOGRAPHAGS-G100N available from SHIMADZU) in accordance with JISK7127:1999 "Plastics-Determination of tensile properties", except that the test piece is a rectangle with a width of 35 mm and a length of 80 mm.

The "stretching stress" indicates the tensile stress (N/35 mm) when the sample is stretched in an elastic region that is measured by a tensile test at an initial chuck interval (distance between marked lines) of 50 mm and a speed of testing of 300 mm/min in accordance with JISK7127:1999 "Plastic—Determination of tensile properties", and an extent of stretching may be appropriately determined depending on the test object. A test piece is preferably formed in a rectangular shape having a width of 35 mm and a length of 80 mm or more. If a test piece with a width of 35 mm cannot be prepared, the test piece with a maximum possible width is prepared and the observed value is converted into a value at a width of 35 mm. Even if a sufficiently large test piece cannot be prepared from a target region with a small area, small test pieces can also be used for comparison of the stretching stress. For example, AOUTGRAPHAGS-G100N manufactured by SHIMADZU may be used as a tensile tester.

The "spread state" refers to a flatly spread state without contraction or slack.

Unless otherwise specified, dimensions of each portion refer to dimensions in the spread state, not the natural length state.

In the absence of description about an environmental condition in a test or measurement, the test or measurement is performed in a test room or a device in a standard state (temperature 20±5° C., relative humidity 65% or less in a test location).

INDUSTRIAL APPLICABILITY

The invention may be generally used for an absorbent article having a stretchable structure such as a sanitary napkin, various disposable diapers such as a tape-type disposable diaper, an underpants-type disposable diaper, etc. in addition to the underpants-type disposable diaper in the above example, etc.

B . . . back body, F . . . front body, T . . . torso region, L . . . intermediate region, 10 . . . inner body, 11 . . . top sheet, 12 . . . liquid impervious sheet, 13 . . . absorber, 13N . . . narrower part, 14 . . . package sheet, 15 . . . gather nonwoven fabric, 16 . . . gather elastic member, 20 . . . outer body, 20A . . . first sheet layer, 20B . . . second sheet layer, 20C . . . folded part, 20X . . . elastic film stretchable structure, 21 . . . side seal portion, 23 . . . waist end portion region, 24 . . . waist portion elastic member, 25 . . . contraction wrinkle, 27 . . . vent hole, 29 . . . leg line, 30 . . . elastic film, 31 . . . through hole, 40 . . . sheet bond portion, 70 . . . non-stretchable region, 71 . . . indication, 80 . . . stretchable region, 81 . . . main stretchable section, 82 . . . buffer stretchable section.

The invention claimed is:

1. An absorbent article comprising
  a stretchable region stretchable at least in one direction, wherein
  the stretchable region is formed by stacking an elastic film between a first sheet layer composed of a nonwoven fabric and a second sheet layer composed of a nonwoven fabric, and in a state in which the elastic film is stretched in a stretching and contracting direction of the stretchable region, the first sheet layer and the second sheet layer are joined via through holes formed in the elastic film at a large number of sheet bond portions arranged at intervals in the stretching and contracting direction and a direction orthogonal thereto, and
  in the sheet bond portions, the first sheet layer and the second sheet layer are joined at least by a melted and solidified material of the elastic film between the first sheet layer and the second sheet layer,
  wherein fibers of the first sheet layer and the second sheet layer continuing from around the sheet bond portions are left in the sheet bond portions,
  the first sheet layer and the second sheet layer are joined by the melted and solidified material of the elastic film, which has infiltrated and solidified among the first sheet layer and the second sheet layer,
  a portion of the first sheet layer and the second sheet layer at the sheet bond portions are melted and a remaining portion of the first sheet layer and the second sheet layer are not melted.

2. The absorbent article according to claim 1, wherein
  an area of each of the sheet bond portions in the stretchable region is in a range of 0.14 to 3.5 mm$^2$,
  an area of an opening of each of the through holes in a natural length state is 1 to 1.5 times the area of each of the sheet bond portions, and
  an area rate of the sheet bond portions in the stretchable region is in a range of 1.8 to 22.5%.

3. The absorbent article according to claim 1, wherein the absorbent article is an underpants-type disposable diaper comprising:
  an outer body included in a front body and a back body; and
  an inner body comprising an absorber and fixed to an internal surface of the outer body,
  both side portions of the front body of the outer body are respectively joined to both side portions of the back body of the outer body to define side seal portions, and an annular torso region, a waist opening, and a pair of right and left leg openings are thereby formed, and
  the stretchable region is included in the outer body.

4. An absorbent article having an absorber that absorbs excrement, the absorbent article comprising
  an elastic film stretchable structure in which an elastic film is stacked between a first sheet layer and a second sheet layer, and the first sheet layer and the second sheet layer are joined via through holes penetrating the elastic film at a large number of sheet bond portions arranged at intervals, wherein
  a region having the elastic film stretchable structure includes a stretchable region stretchable in at least one direction,
  wherein the stretchable region is contracted in a stretching and contracting direction by a contraction force of the elastic film while it is possible that the stretchable region is stretched in the stretching and contracting direction, and
  vent holes are formed by piercing to penetrate the first sheet layer and/or the second sheet layer in a thickness direction at a portion other than the sheet bond portions.

5. The absorbent article according to claim 4, wherein in a state in which the stretchable region is stretched, the vent holes are disposed with respect to the through holes such that a part or a whole of each of the vent holes overlaps each of the through holes.

6. The absorbent article according to claim 4, wherein independently of a state in which the stretchable region is stretched or not, none of the vent holes overlaps the through holes.

7. The absorbent article according to claim 4, wherein the first sheet layer is a nonwoven fabric and the second sheet layer is a nonwoven fabric, and a number of the vent holes per unit area is smaller than a number of the through holes per unit area.

8. The absorbent article according to claim 4, wherein at least one vent hole is formed on each side of each of the sheet bond portions in the stretching and contracting direction.

9. The absorbent article according to claim 4, wherein an area of each of the vent holes is in a range of 0.34 to 3.5 mm$^2$, and an area rate of the vent holes is in a range of 4.4 to 19.1%.

10. The absorbent article according to claim 4, wherein
- a region having the elastic film stretchable structure includes a non-stretchable region provided at least at one side of the stretchable region in the stretching and contracting direction,
- the non-stretchable region is a region in which an elongation at an elastic limit in the stretching and contracting direction is 130% or less, and
- the vent holes are formed in the non-stretchable region and are or are not formed in the stretchable region.

11. The absorbent article according to claim 4, wherein the absorbent article is an underpants-type disposable diaper having
- an outer body included in a front body and a back body,
- an inner body that includes the absorber and is fixed to the outer body, wherein
- both side portions of the front body of the outer body are respectively joined to both side portions of the back body of the outer body to define side seal portions, and an annular torso region, a waist opening, and a pair of right and left leg openings are thereby formed, and
- the elastic film stretchable structure is included in the torso region of the outer body in at least one of the front body and the back body such that the stretching and contracting direction thereof corresponds to a width direction.

* * * * *